(12) United States Patent
Rahilly et al.

(10) Patent No.: US 10,956,864 B2
(45) Date of Patent: Mar. 23, 2021

(54) SECURE SMART CONTAINER ASSEMBLY, SYSTEMS, AND METHODS

(71) Applicant: CareFusion 303, Inc., San Diego, CA (US)

(72) Inventors: Michael Rahilly, Encinitas, CA (US); Brendan John Burgess, Poway, CA (US); Ramkumar Subramanian, San Diego, CA (US); Mustafa Yusufi, Escondido, CA (US); Monica Wyly, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 16/914,190

(22) Filed: Jun. 26, 2020

(65) Prior Publication Data

US 2020/0410433 A1 Dec. 31, 2020

Related U.S. Application Data

(60) Provisional application No. 62/867,841, filed on Jun. 27, 2019, provisional application No. 62/953,091, (Continued)

(51) Int. Cl.
*G08B 13/14* (2006.01)
*G06Q 10/08* (2012.01)
(Continued)

(52) U.S. Cl.
CPC ....... *G06Q 10/087* (2013.01); *B65D 21/0213* (2013.01); *B65D 43/22* (2013.01);
(Continued)

(58) Field of Classification Search
CPC .................................................. G08B 25/016
(Continued)

(56) References Cited

U.S. PATENT DOCUMENTS

| | | | |
|---|---|---|---|
| 2007/0109097 A1* | 5/2007 | Coutermarsh | E05B 81/52 340/5.73 |
| 2010/0326146 A1* | 12/2010 | Powers | E05B 83/02 70/159 |

(Continued)

FOREIGN PATENT DOCUMENTS

| WO | WO-2016268006 A1 | 10/2016 |
|---|---|---|
| WO | WO-2018102548 A1 | 6/2018 |

OTHER PUBLICATIONS

Invitation to Pay Additional Fees for Application No. PCT/US2020/040001, dated Sep. 21, 2020, 12 pages.
(Continued)

*Primary Examiner* — Tai T Nguyen
(74) *Attorney, Agent, or Firm* — Morgan, Lewis & Bockius LLP

(57) ABSTRACT

The disclosed systems and methods provide a smart container or bin. A container bin assembly includes a bin body, a latching mechanism, and controller. A method includes receiving, via a communication interface, an authenticated request to access the smart container, actuating an electromechanical latch to disengage a fastening hook, thereby initiating a mechanical movement of an access component to make an internal compartment accessible, outputting, via an audiovisual element, an alert to identify the container, confirming that the electromechanical latch has re-engaged with the fastening hook, thereby securing the internal compartment, determining a change in a local inventory, and updating the local inventory in a non-volatile data store according to the change.

19 Claims, 28 Drawing Sheets

Related U.S. Application Data filed on Dec. 23, 2019, provisional application No. 62/986,508, filed on Mar. 6, 2020.

(51) Int. Cl.
| | |
|---|---|
| *G16H 20/13* | (2018.01) |
| *B65D 21/02* | (2006.01) |
| *B65D 43/22* | (2006.01) |
| *B65D 43/26* | (2006.01) |
| *E05B 47/00* | (2006.01) |
| *G07C 9/00* | (2020.01) |

(52) U.S. Cl.
CPC ............. *B65D 43/26* (2013.01); *G16H 20/13* (2018.01); *B65D 2203/10* (2013.01); *B65D 2255/20* (2013.01); *E05B 47/00* (2013.01); *G07C 9/00* (2013.01)

(58) Field of Classification Search
USPC ...... 340/572.1, 572.2, 572.8, 5.6, 5.64, 540, 340/541, 425.5; 235/382, 385, 492
See application file for complete search history.

(56) References Cited

U.S. PATENT DOCUMENTS

| | | |
|---|---|---|
| 2013/0320820 A1 | 12/2013 | Rahilly |
| 2015/0366377 A1 | 12/2015 | Savage et al. |
| 2018/0308564 A1* | 10/2018 | Ross .................... G06F 16/955 |

OTHER PUBLICATIONS

International Search Report and Written Opinion for Application No. PCT/US2020/04001, dated Nov. 13, 2020, 19 pages.

\* cited by examiner

DISPLAY 365A

Content: Alcohol Wipes          Press Take button to subtract qty. ->

Quantity: 100                   Press Receive button to add qty. ->

Battery: 90%                    Network: OK

---

DISPLAY 365B

Management Mode                 Press Take to change menu item ->

->   Choose item              Short press Receive to confirm ->
     Set quantity             Long press Receive to exit ->
     Power management
     Review data logs

---

DISPLAY 365C

Restock Mode                    Press Take to cycle digits ->

Item description: Alcohol Wipes  Short press Receive to adjust value ->
               *            Long press Receive to exit ->
Quantity:      [1]    [0]    [0]

FIG. 3

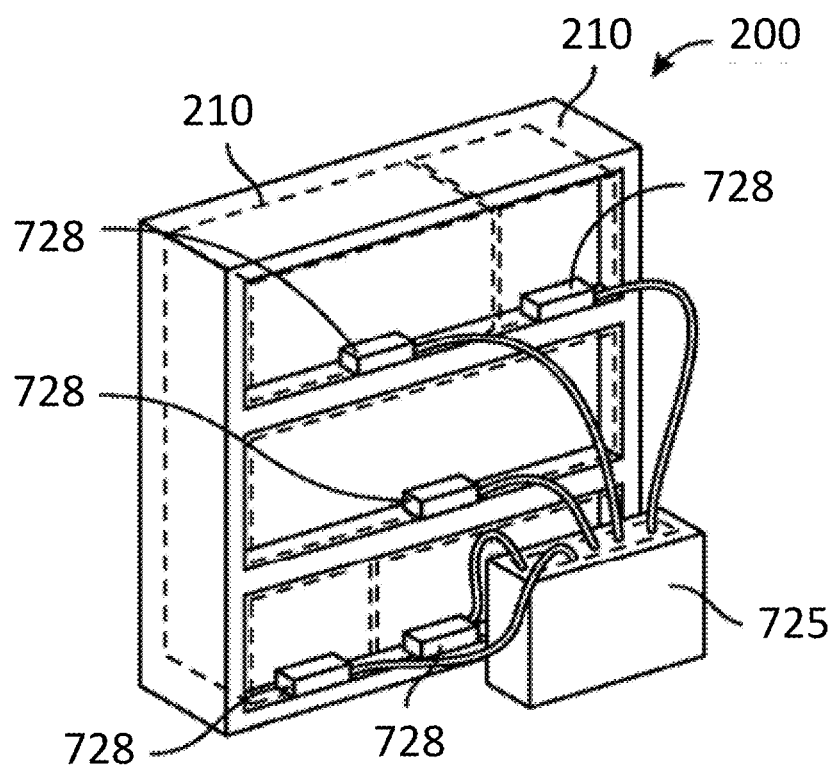
FIG. 13
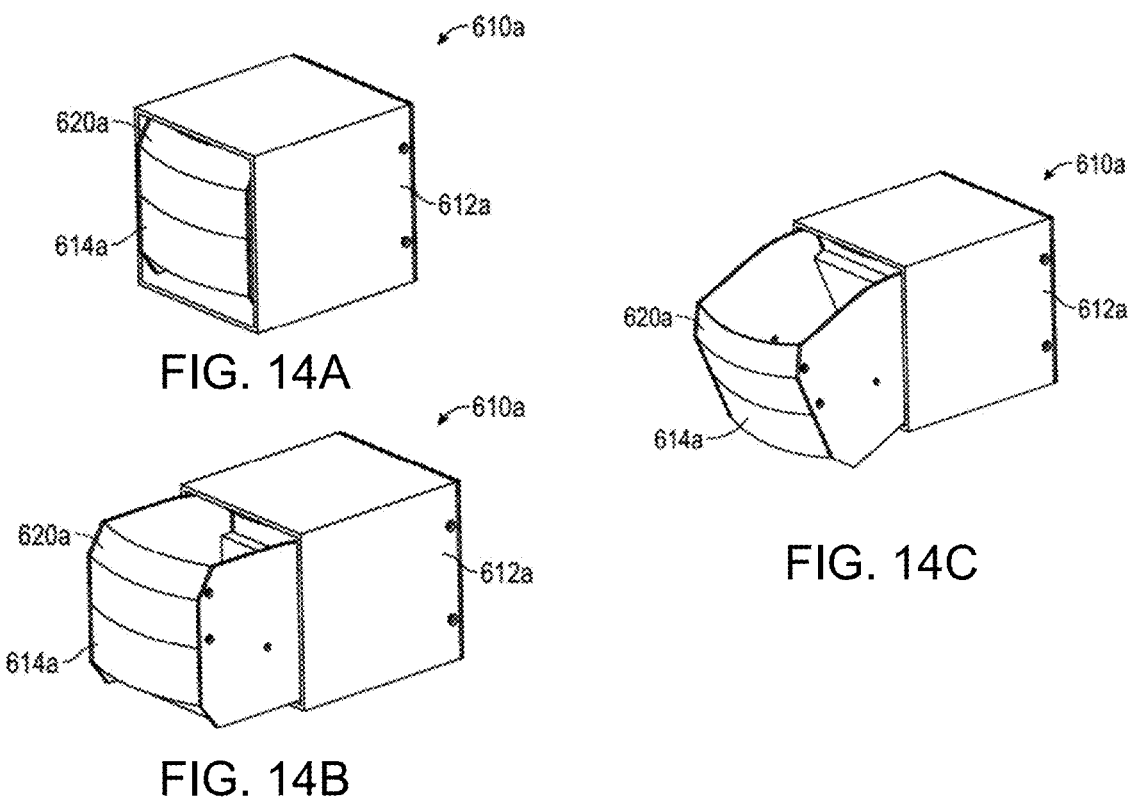
FIG. 14A
FIG. 14B
FIG. 14C

Badge access to locked medication storage
FIG. 19C
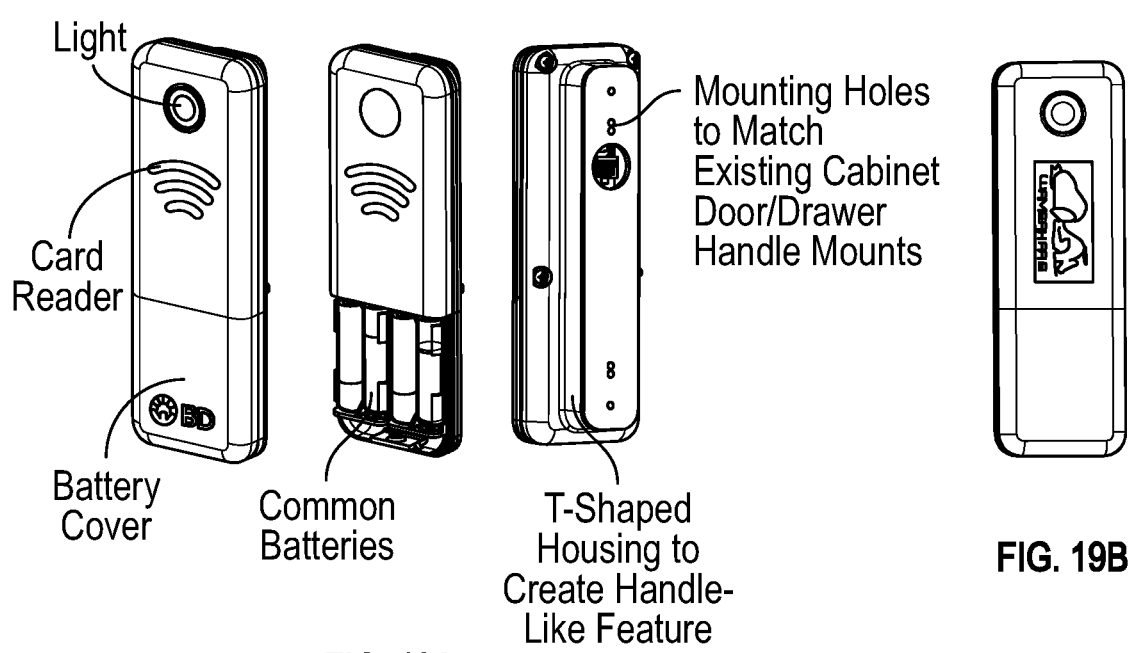
FIG. 19A
FIG. 19B

SECURE SMART CONTAINER ASSEMBLY, SYSTEMS, AND METHODS

CROSS REFERENCE TO RELATED APPLICATIONS

This application claims the benefit of priority as a nonprovisional application of U.S. Application Ser. No. 62/867,841, entitled "SECURE AND EFFICIENTLY DEPLOYABLE MEDICATION DISPENSING," filed on Jun. 27, 2019, and claims the benefit of priority as a nonprovisional of U.S. Application Ser. No. 62/953,091, entitled "SMART CONTAINER," filed on Dec. 23, 2019, and claims the benefit of priority as a nonprovisional application of U.S. Application Ser. No. 62/986,508, entitled "SECURE BIN ARRAY ASSEMBLY," filed on Mar. 6, 2020, the entirety of each of which is incorporated herein by reference.

TECHNICAL FIELD

The present disclosure generally relates to access control devices, and more specifically to methods and systems for secure medication storage.

BACKGROUND

To organize and dispense items in both acute and non-acute medical settings, the items are often stored in dispensing mechanisms or various bins. While bins may be readily procured and desirable in many situations, they lack smart functionality and management features. This poses several drawbacks of heightened concern for care facilities, such as doctor's offices, pharmacy clinics, outpatient clinics, institutional infirmaries (e.g., school nurse offices), hospitals, retail clinics, ambulatory clinics, or the like.

For example, without smart functionality and management features, inventory management must be carried out manually, which is prone to human error. It may also be difficult to maintain efficient levels of medications and other medical inventory, which results in procedural delays from understock and waste or spoilage from overstock. Further, it can be difficult to identify the location of a particular item or bin for restocking or dispensing, especially in a large care setting with many different items to track. Yet further, it may be difficult to safely transport sensitive items and verify whether a bin is intact, posing a security issue for controlled medications, high value medications, and other items susceptible to diversion. Accordingly, there is a need for improved systems and methods of item storage, particularly for medicine and other healthcare items used in care facilities.

SUMMARY

According to various aspects of the subject technology, a method for providing efficient space utilization, secure transport and storage, inventory management, tamper resistance, and other smart functionality for containers is provided. The method may include providing a smart container attachable to a stationary mounting frame. The method may also include receiving, via a communication interface, an authenticated request to access the smart container. The method may also include actuating an electromechanical latch to disengage a fastening hook, thereby initiating a mechanical movement of an access component to make an internal compartment accessible. The method may also include outputting, via an audiovisual element, an alert to identify the container. The method may also include confirming that the electromechanical latch has re-engaged with the fastening hook, thereby securing the internal compartment. The method may also include determining a change in a local inventory. The method may also include updating the local inventory in a non-volatile data store according to the change. Other aspects include corresponding systems, apparatuses, and computer program products for implementation of the computer-implemented method.

Bin assemblies are also described herein. According to various aspects of the subject technology, a bin assembly includes a bin housing adapted to receive bins of varying sizes and including a vertical mounting structure, a bin body, a latching mechanism, and a controller. The bin body defines a bin volume, wherein the bin body is movable relative to the bin housing to permit access to the bin volume in an open position and to prevent access to the bin volume in a closed position. The latching mechanism includes a latching member wherein the latching member engages the latching hook in a locked position to retain the bin body in the closed position and the latching member is spaced apart from the latching hook in a released position. The controller is configured to control movement of the latching member based at least in part on the wireless control signal.

According to various aspects of the subject technology, a bin assembly comprises a bin housing adapted to receive bins of varying sizes, the bin housing including a vertical mounting structure; a bin body comprising a latching hook and the bin body defining a bin volume, wherein the bin body is movable relative to the bin housing to permit access to the bin volume in an open position and to prevent access to the bin volume in a closed position; a latching mechanism coupled to the bin housing, the latching mechanism comprising a latching member, wherein the latching member engages the latching hook in a locked position to retain the bin body in the closed position and the latching member is spaced apart from the latching hook in a released position; and a controller configured to: receive a wireless control signal; and control movement of the latching member based at least in part on the wireless control signal.

Additionally or in the alternative, a bin array assembly, comprises: a plurality of bin assemblies, wherein each bin assembly of the plurality of bin assemblies comprises: a bin housing adapted to receive bins of varying sizes, the bin housing including a vertical mounting structure; and a bin body comprising a latching hook and the bin body defining a bin volume, wherein the bin body is movable relative to the bin housing to permit access to the bin volume in an open position and to prevent access to the bin volume in a closed position, wherein each of the bin assemblies of the plurality of bin assemblies is disposed horizontally adjacent or vertically adjacent to a neighboring bin assembly of the plurality of bin assemblies; a latching mechanism configured to engage the latching hook of a respective bin assembly of the plurality of bin assemblies in a locked position to retain the bin body of the respective bin assembly of the plurality of bin assemblies in the closed position and to disengage the latching hook of the respective bin assembly of the plurality of bin assemblies in a released position; and a controller configured to: receive a wireless control signal; and control movement of the latching member based at least in part on the wireless control signal.

According to various aspects of the subject technology, a method comprises: providing a bin assembly comprising a bin housing and a bin body movable relative to the bin housing, wherein the bin housing is adapted to receive bins of varying sizes; receiving a wireless control signal; latching the bin body to the bin housing in a locked position to retain the bin body in a closed position via a latching mechanism based at least in part on the wireless control signal; unlatching the bin body from the bin housing in a released position via the latching mechanism based at least in part on the wireless control signal; moving the bin body relative to the bin housing to an open position; and providing access to a bin volume defined within the bin body. Other aspects include corresponding systems, apparatuses, and computer program products for implementation of the method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIG. 3 depicts various example user interfaces of a smart container, according to various aspects of the subject technology.

FIG. 13 is a reverse perspective view of a bin array assembly for use with the medication management system of FIG. 6, in accordance with various aspects of the present disclosure.

FIG. 14A is a perspective view of a bin for use with the bin array assembly of FIG. 7A in a closed position, in accordance with various aspects of the present disclosure.

FIG. 14B is a perspective view of the bin of FIG. 14A with the bin in a partially open position, in accordance with various aspects of the present disclosure.

FIG. 14C is a perspective view of the bin of FIG. 14A with the bin in an open position, in accordance with various aspects of the present disclosure.

FIGS. 19A, 19B, and 19C depict a remote smart lock reader module configured to unlock a securable container, including to cabinet doors and/or cabinet drawers for controlled security, according to various aspects of the subject technology.

DESCRIPTION

Figure 1A:
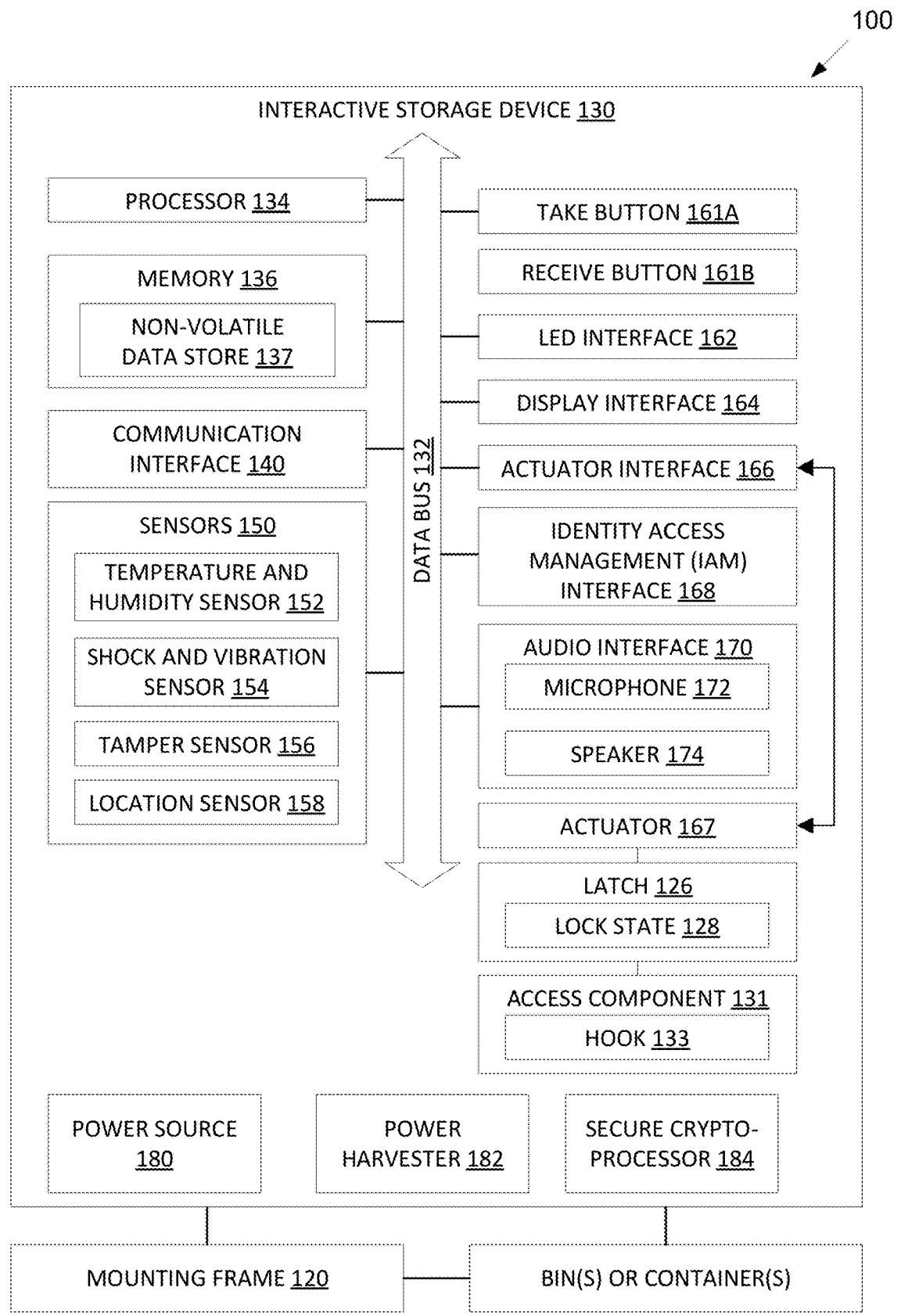
FIG. 1A depicts an example system including a smart container to provide efficient space utilization, secure transport and storage, inventory management, tamper resistance, and other smart functionality, according to various aspects of the subject technology.

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

Storage, transport, and dispensing of medicine and other healthcare items demand robust inventory management to prevent medicine spoilage, reduce overhead, and minimize costly diversion, theft, and other losses. Various systems may exist to address individual aspects of these demands. However, combining various disparate systems to address the multiple requirements of medicine transportation may be costly, unwieldy, and difficult or impossible to implement in practice.

The subject technology provides efficient space utilization, secure transport and storage, inventory management, tamper resistance, and other smart functionality via a smart container to address the numerous requirements of medicine and healthcare item dispensing in care facilities. A smart container, as described herein, can be provided with various different access components that can be secured using an electromechanical latch, such a hinged swing out lid or a sliding pop out drawer. Upon user authentication, the latch may be actuated to provide access to items for dispensing. Smart containers may attach to other containers to form stacks or arrays for efficient organization and space utilization. Further, smart containers can be used in both mobile and stationary contexts, enabling secure transport and storage of items. For example, smart containers may be attachable to and removable from stationary mounting frames, which may be positioned on countertops, on walls, within cabinets, within refrigerators, or within other locations. Tamper resistant features such as deformable materials, tamper sensors, and breakaway hooks may be provided to leave evidence for verifying container integrity and deterring theft and diversion.

A user may utilize a remote device such as a tablet, smartphone, desktop or laptop computer to request access to a particular smart container. In some implementations, the user may provide a credential such as a smart card or another device. When the request is authenticated, the smart container may identify itself to the user, for example by flashing a light emitting diode (LED) sounding a buzzer, opening spring-loaded lid, or releasing a spring-loaded drawer, or some combination thereof or equivalents thereof. The smart container may proceed to actuate an electromechanical latch that causes an access component to provide access to an internal compartment containing items for dispensing. Access may be provided based on certain criteria, such as the location of the user (e.g., distance, proximity, etc.) with respect to the smart container and the access permissions granted to the user (e.g., with regard to the contents of the smart container). According to various implementations, when access is provided, a hinged lid may swing out to reveal an internal compartment, or a drawer may slide out. Sensors or interfaces may be provided to enable automatic inventory management. Smart containers may communicate with each other to propagate inventory status, container location, environmental and activity event logs, and other sensor data, which can be used for inventory tracking, machine learning analytics, and proactive loss prevention.

Smart functionality generally refers to processing capabilities and, for the smart container, environment monitoring and access control processing capabilities. A smart device can have on-board memory or other storage capacity that can be written to and read from. The memory can contain one or more applications for implementing a particular function. The particular smart device may also contain an operating system and/or user interface. Some smart functionality may include wireless communications. For example, a smart device may include a transceiver for communicating through an electric field and/or magnetic field between the device and another entity such as a wireless terminal or information reader, or another smart container.

The smart container may include various interfaces and devices to support various smart functionality such as environmental sensing, tamper detection, infrastructure and mesh networking, near-field communications, positional tracking, and user interfaces with audiovisual elements for inventory management, alerts, and user guidance. In this manner, the smart container can interface and synchronize with a centralized back-end server to support inventory tracking, item condition tracking, and data collection for machine learning, as described in further detail in conjunction with FIGS. 2A and 2B below.

FIG. 1A depicts an example system 100 including interactive storage device 130 to provide efficient space utilization, secure transport and storage, inventory management, tamper resistance, and other smart functionality, according to various aspects of the subject technology. Interactive storage device 130 includes latch 126, access component 131, data bus 132, processor 134, memory 136, communication interface 140, sensors 150, button interface 160, LED interface 162, display interface 164, actuator interface 166, actuator 167, identity access management (IAM) interface 168, audio interface 170, power source 180, power harvester 182, and secure crypto-processor 184. According to various implementations, interactive storage device 130 may include or be implemented as an electronically securable container that includes or is associated with an access controller for operating an electronically securable container. For example, the access controller may be attached to the container (e.g., on the front of the container, adjacent a lid 131.) In this regard, access controller and the container may be referred to together as a single interactive storage device 130. According to various aspects, the access controller may be referred to separately, for example, as a smart bin controller or smart tote controller or smart card reader.

In some implementations, latch 126, hook 133, and access component 131 (or lid) may be included in a container portion 210, while buttons 161, LED interface 162, and display 165 may be implemented in the smart controller portion. Latch 126 includes lock state 128. Access component 131 includes hook 133. Memory 136 includes non-volatile data store 137. Sensors 150 include load sensor 151, temperature and humidity sensor 152, shock and vibration sensor 154, tamper sensor 156, and location sensor 158. Audio interface 170 includes microphone 172 and speaker 174. Interactive storage device 130 is attachable to and detachable from mounting frame 120. The components included in interactive storage device 130 are exemplary and other implementations may include a different configuration of components according to use case requirements, power consumption targets, care facility setting, and price point constraints.

Interactive storage device 130 may include processor 134, which may correspond to any type of general or specialized processor, controller, integrated circuit, application specific integrated circuit (ASIC), field programmable gate array (FPGA), system-on-chip, or similar device, and may include hardcoded circuit elements, firmware, software, or any combination thereof to implement one or more of the specific smart containering features describe herein. Processor 134 may communicate with other components of interactive storage device 130 via data bus 132, which may comprise one or more communication buses, such as parallel or serial buses.

Interactive storage device 130 may include memory 136, which may include volatile work memory as well as non-volatile data store 137 for long term data storage. For example, non-volatile data store 137 may comprise flash memory or other memory that retains data after power source 180 is unavailable. Non-volatile data store 137 may include several data logs that record, for example, user authentication events, periodic sensor data, and local inventory of interactive storage device 130.

Communication interface 140 may include one or more wireless radios to communicate with other devices and/or other smart containers. For example, communication interface 140 may include one or more radios, scanners, or other devices that are compliant with Bluetooth, Bluetooth Low Energy, Near Field Communication (NFC), Wi-Fi, contactless Smartcards, Radio-Frequency identification, 1-D and 2-D barcodes, and other protocols.

Sensors 150 may include one or more sensors to record, for example, environmental conditions and evidence related to attempts to divert or tamper with the contents of interactive storage device 130. For example, load sensor 151 may comprise a load cell that can measure the mass of items contained in interactive storage device 130, which can be used to estimate changes in item quantities. Temperature and humidity sensor 152 may record inside and/or outside ambient temperature and humidity. Shock and vibration sensor 154 may help to determine whether an attempt to divert has occurred, or whether the contents of interactive storage device 130 were damaged during transport and handling.

For example, measurements from the shock and vibration sensor 154 may be monitored in real time or periodically audited for shock or vibration measurements that correspond to a detection threshold. If a measurement or series of measurements correspond to the threshold, the interactive storage device 130 (or other monitoring device in communication therewith) may adjust the interactive storage device 130 or other element in the environment.

Tamper sensor 156 may determine whether case intrusion has occurred, for example if retaining screws, containers, covers, or other components of interactive storage device 130 have been opened, unsealed, drilled, deformed, or otherwise tampered. For example, mechanical switches, anti-tamper films, photodiodes with reflective materials, infrared proximity sensors, and other devices may be used. Location sensor 158 may include, for example, a global positioning system (GPS) radio to enable location history tracking. Alternatively or additionally, in some implementations, triangulation may be used to determine location, for example by using Wi-Fi or Bluetooth triangulation using known networks and/or hubs and/or beacons. In combination with secure crypto-processor 184, sensors 150 may securely record real-time sensor data to comply with National Institutes of Standards and Technology (NIST) requirements. Sensors 150 may include other sensors not shown, such as a light sensor to monitor the status of items sensitive to light exposure.

Location information generated by the location sensor 158 may be monitored in real time or periodically audited to identify deviations from expected location or route for the interactive storage device 130. If a measurement or series of measurements differ from the expected location(s), the interactive storage device 130 (or other monitoring device in communication therewith) may adjust the interactive storage device 130 or other element in the environment. Adjustments may include adjusting a power state of the controller or lock 126, transmitting a control message to the actuator interface 166 to adjust the lock state 128, activating an interface of the controller to provide a perceivable indicator of the detected state, or the like.

In some implementations, one or more of the sensors 150 may be used to identify when a user is near interactive storage device 130. For example, an infrared proximity sensor may be directed away from the container to detect an area in front of interactive storage device 130. When a user is detected within the area, interactive storage device 130 may adjust one or more functions such as entering a different power mode, activating wireless communications or a display, or enabling one or more of the button interfaces. In this way, interactive storage device 130 can preserve resources such as battery, memory, or network bandwidth. The detection may be based on a duration of time. By including time, the device may avoid waking or adjusting state for a clinician simply passing by who may only be within the area for a short period of time. Presence in the area for a duration of time longer than the threshold may indicate intent to interact with interactive storage device 130. In such instances, the presence within the area for at least the threshold period of time may cause the activation, power mode change, activation of a communication interface (e.g., wireless transceiver, Bluetooth radio), or other adjustment of interactive storage device 130. Further, in some implementations, proximity of an authorized user may automatically trigger a request to unlock and open a smart container.

Button interface 160 may enable user input and selections on a user interface. For example, display interface 164 may show a user interface directing the user to push specific buttons to update inventory, for example. In some implementations, the buttons may be labelled with their function, for example T or a minus sign for taking an item from the smart container, and R or a plus sign for receiving an item into the smart container. Alternatively or additionally, display interface 164 may provide a touchscreen panel to accept user input. In some implementations, user input may be received from a remote device, such as a tablet or smartphone, via communication interface 140.

Light emitting diode (LED) interface 162 may drive one or more multi-color LEDs, addressable RGB (ARGB) LEDs, or organic LEDs (OLEDs) for providing a quickly identifiable status indication. For example, LEDs may be driven at varied brightness, blinking patterns, and colors to indicate various states of interactive storage device 130. In one configuration, solid red LEDs may indicate that sensors 150 have recorded potentially unsafe environmental conditions for the contents of interactive storage device 130, such as temperature outside of a safety range for medicines, whereas solid green LEDs may indicate that sensors 150 have recorded environmental conditions within safe parameters. Blinking green LEDs may indicate that an authorized user has submitted valid credentials for unlocking latch 126 to access the contents of interactive storage device 130. Blinking red LEDs may indicate that tamper sensor 156 and/or shock and vibration sensor 154 have recorded an intrusion attempt, for example if a detected deformation, vibration or shock value exceeds a predetermined threshold. Blinking yellow LEDs may indicate that power source 180 has crossed a low battery threshold and needs replacement. Blinking white LEDs may visually identify interactive storage device 130 to the user, allowing the user to readily identify interactive storage device 130 associated with a requested item in a pharmacy, stock room, or other facility. In some embodiments, unique LED colors may be assigned on a per-user basis to enable multiple users to concurrently identify smart containers. Further, in some implementations, the LED colors and blinking patterns may be detected by a handheld scanner or another device to assist in inventory tracking and management.

Display interface 164 may drive a display to show various user interfaces enabling a user to query the inventory of interactive storage device 130, to update the local inventory of interactive storage device 130 by adding or removing items, to query the condition of the items, to display remaining battery life, and to perform other management and status query operations. The user interfaces may utilize text and graphics such as icons, animations, and other elements. In some implementations, these user interfaces may additionally or alternatively be presented on a remote device, such as a tablet or smartphone. Display interface 164 may drive an electronic ink (e-ink) display, a touchscreen liquid crystal display (LCD), an OLED, or another display type. The information may be presented on the display interface 164 in human readable form (e.g., letters, numbers, or images) or machine-readable form (e.g., barcode, quick read code, standardized scan code form, or custom scan code form).

Actuator interface 166 may trigger actuator 167 to actuate latch 126, thereby changing lock state 128 from open to closed and vice versa. For example, latch 126 may correspond to an electromechanical lock or an electromechanical latch. Actuator interface 166 may also query latch 126 to determine lock state 128. Triggering actuator 167 may also cause a movement of access component 131 to provide access to an internal compartment. For example, unlocking latch 126 may decouple hook 133, which in turn allows a spring to cause a movement of access component 131, as described further below in conjunction with FIG. 1F, FIG. 1H, and FIG. 1G. Hook 133 may correspond to a fixed or retractable hook that can couple to or decouple from latch 126. In some implementations, a manual lock may be provided to manually lock and unlock latch 126 without using actuator interface 166. In this case, any manual locking or unlocking action may be recorded within an access log in non-volatile data store 137. A manual lock may be useful to provide access to the contents of interactive storage device 130 during a malfunction or when power source 180 is exhausted and no replacement is readily available.

Identity access management (IAM) interface 168 may include one or more devices to enable a user to provide credentials for user authentication. For example, IAM interface 168 may include one or more biometric scanners, such as a fingerprint sensor, an iris scanner, an electrocardiogram (ECG) reader such as a smartwatch, and a depth camera for facial recognition. IAM interface 168 may also include smartcard readers or other devices to read a contactless smartcard or other unique identifier or token. In some implementations, IAM interface 168 may use communication interface 140 to utilize biometric scanners or readers present on a remote device, such as a tablet or smartphone. Accordingly, IAM interface 168 may receive user credentials which can be validated in conjunction with secure crypto-processor 184.

When multiple authentication methods are available in IAM interface 168, then a particular authentication method may be automatically selected for authentication. For example, the authentication methods may be sorted according to security strength, and the methods with the highest security strength may be preferred for use. In some implementations, the user may select the preferred method of authentication. Further, a super user or a user with elevated privileges may manually authenticate a user, for example if the user misplaces his credentials.

Audio interface 170 may include one or more audio devices, such as microphone 172 and speaker 174. Microphone 172 may enable voice commands to be used instead of button interface 160 or display interface 164. Speaker 174 may enable audio prompts, feedback, and alerts to be emitted. Speaker 174 may comprise a piezoelectric speaker, a dynamic speaker, or another type of speaker. For example, different tones may be emitted from the piezoelectric speaker to indicate different states or user prompts.

Power source 180 provides electrical power for the components of interactive storage device 130. Power source 180 may comprise a non-rechargeable battery, a rechargeable battery, a capacitor or super-capacitor, or another energy storage device. Power source 180 may be user accessible and replaceable. To supplement or recharge power source 180, power harvester 182 may be used to receive power from external sources. For example, power harvester 182 may receive wireless power through inductive coils or RF sources. Power harvester 182 may also receive power through mechanical action, such as via piezo transducers interfaced to buttons connected to button interface 160, or via electromagnetic induction induced by actuation movement of latch 126. Power harvester 182 may also receive power through direct wired connection, such as via universal serial bus (USB) charging cables, AC-DC chargers, or DC-DC chargers, which may be plugged into an external battery pack or wall mains voltage supply. In some implementations, power harvester 182 may receive power through mounting frame 120, which may function as a power docking station. In the event that power source 180 is depleted, lock state 128 may be maintained in its current state, whether closed or open, until power source 180 is replaced or a manual lock is engaged, when made available.

To extend the operating time of power source 180, various power management strategies may be utilized. For example, interactive storage device 130 may be placed in a low power or sleep state when no activity is anticipated. When activity such as user interactions, periodic network updates, or sensor logging is necessary, interactive storage device 130 may wake up to a normal operating mode, and return to the low power or sleep state once the activity is completed. The estimation of low activity may be based on network activity, user preferences, working schedules, or other factors. Interactive storage device 130 may also wake up in response to an activation word or phrase via microphone 172, a button press on button interface 160, or a touch input from display interface 164. In some implementations, sensors 150 may include occupancy sensors which may be used to determine estimated activity levels. In some implementations, microphone 172 may be used as an occupancy sensor. In some implementations, power management may be based on machine learning algorithms, as described in further detail below in FIG. 2A.

In some implementations, the power management strategies may include utilizing machine learning to generate a power profile. For example, each smart tote controller may log usage data in non-volatile data store 137, which can then be collected by a remote server and processed by one or more machine learning algorithms to determine a power management profile for optimized power consumption. For example, the power management profile may define daily time periods when user interactions are infrequent, and processor 134 may use this profile to transition processor 134 and other components to a low power idle or sleep mode during these daily time periods.

Secure crypto-processor 184 may correspond to a trusted platform module (TPM) chip that stores public and private encryption keys for encrypting and decrypting data. For example, the public keys may include public keys of key pairs generated by authorized users, allowing each user to submit credentials encrypted by a respective private key for decrypting by secure crypto-processor 184. Similarly, private keys specific to interactive storage device 130 can be used to encrypt data before transmitting, storing, and exposing the data (e.g., to the outside world). In this manner, data travelling through data bus 132 and stored in memory 136, including non-volatile data store 137, can be securely encrypted to protect against third party eavesdropping and modification. Encrypted data can also be more safely transmitted to the outside world, including over potentially insecure and untrusted networks.

In some implementations, the components of interactive storage device 130 and mounting frame 120 may be hardened against extreme temperatures. For example, the components of interactive storage device 130 and mounting frame 120 may be configured to be operable within a refrigerated environment. In this manner, interactive storage device 130 and mounting frame 120 may be stored in refrigerators, freezers, or other cold storage.

In some implementations, a remote device such as a tablet, smartphone, laptop, or other device may be used to interface with interactive storage device 130. For example, the remote device may include an optical scanner that can read 1D or 2D barcodes and/or LED flashing patterns to receive data from interactive storage device 130. The scanner may be used, for example, to identify interactive storage device 130 for loading medications into interactive storage device 130. For example, interactive storage device 130 may include an embedded unique identifier or serial number that can be transmitted using barcodes or LEDs. The remote device may contact a remote server, e.g. a pharmacy server, to determine, for example, a type and quantity of medications to be added to interactive storage device 130. Pharmacy and local inventories may also be automatically updated according to the expected change in contents of interactive storage device 130. In some implementations, the container may already be loaded with medications, and the user only needs to identify the correct container. For example, as discussed above, LED lights may blink on a specific smart container for identifying to the user. A similar process may be used for dispensing medications from interactive storage device 130.

The remote device may execute a local application downloaded from an application store, a corporate network, a website, or another distribution method. Alternatively, the remote device may execute a remote cloud-based application or a Software as a Service (SaaS) application. The application may allow communication with smart containers such as interactive storage device 130. For example, the application may utilize radios that support various protocols such as Bluetooth, Bluetooth Low Energy, Near Field Communication (NFC), Wi-Fi, contactless smartcards, Radio-Frequency identification, and others.

When the remote device is connected to a network, such as via a Wi-Fi or cellular connection, interactive storage device 130 may utilize the network to communicate and synchronize with a remote server, as described in further detail below in conjunction with FIG. 2A and FIG. 2B. Alternatively, when such a connection is not present, interactive storage device 130 may utilize mobile mesh networking to use other smart containers as nodes to connect to the remote server. Further, interactive storage device 130 may function as a wireless repeater to provide a network connection to other smart devices inside and outside of interactive storage device 130. In some implementations, a cellular modem may be included within interactive storage device 130 to provide a direct cellular connection to the remote server. However, to reduce implementation complexity and data network costs, it may be preferable to omit a cellular modem.

Figure 1B:
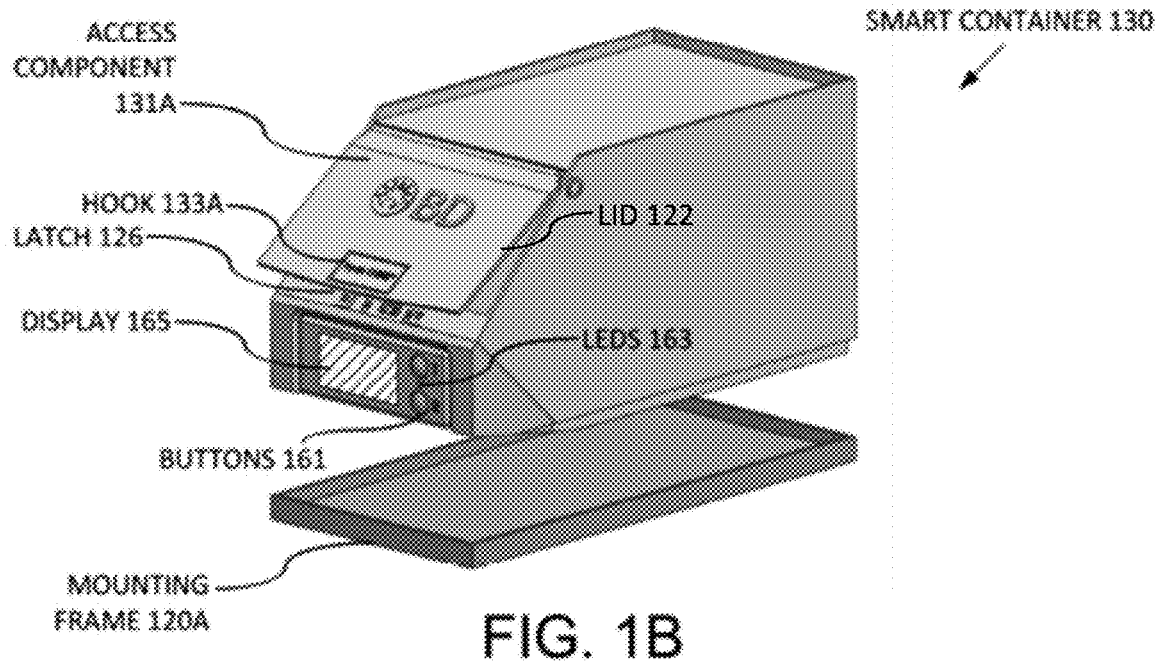
FIG. 1B depicts a perspective view of an example smart container with a hinged lid that is attachable to a stationary mounting frame, according to various aspects of the subject technology.

With a block diagram overview of system 100 now in place, it may be helpful to observe various perspective views of the components of system 100. FIG. 1B depicts a perspective view of interactive storage device 130 with a hinged lid, or access component 131A, according to various aspects of the subject technology. Interactive storage device 130 is attachable to mounting frame 120A. Interactive storage device 130 includes latch 126, access component 131A, hook 133A, buttons 161, LEDs 163, and display 165.

Referring to FIG. 1A, various interfaces may drive or control the components of interactive storage device 130. For example, button interface 160 may receive user inputs from buttons 161. LED interface 162 may drive LEDs 163 to indicate various states and alerts. Display interface 164 may drive display 165, which may display status messages and various user interfaces for managing interactive storage device 130 and the contents of interactive storage device 130. Actuator interface 166 may instruct actuator 167 to actuate latch 126, causing hook 133A to decouple from latch 126. For example, when hook 133A is decoupled from latch 126, access component 131A may automatically swing outward due to spring tension in a hinge causing a rotation along the hinge. A stopper feature such as a plastic stopper may be utilized to limit the angle of the outward movement.

The specific elements shown in interactive storage device 130 are exemplary and any configuration of elements may be utilized according to use case requirements.

Interactive storage device 130 may attach to mounting frame 120A, which may be placed on any surface such as a countertop, cabinet, desk or shelf. In some implementations, mounting frame 120A may be permanently attached to a surface, for example by screws or other fasteners. Interactive storage device 130 may also be detachable from mounting frame 120A to allow organization and transport of interactive storage device 130. In some implementations, interactive storage device 130 can be locked to mounting frame 120A to prevent unauthorized removal. For example, a locking latch may be located near the rear of mounting frame 120A that couples to a matching feature on interactive storage device 130. The locking latch may be controlled in a similar manner as latch 126, or may be manually controlled using a key or other access control.

Figure 1C:
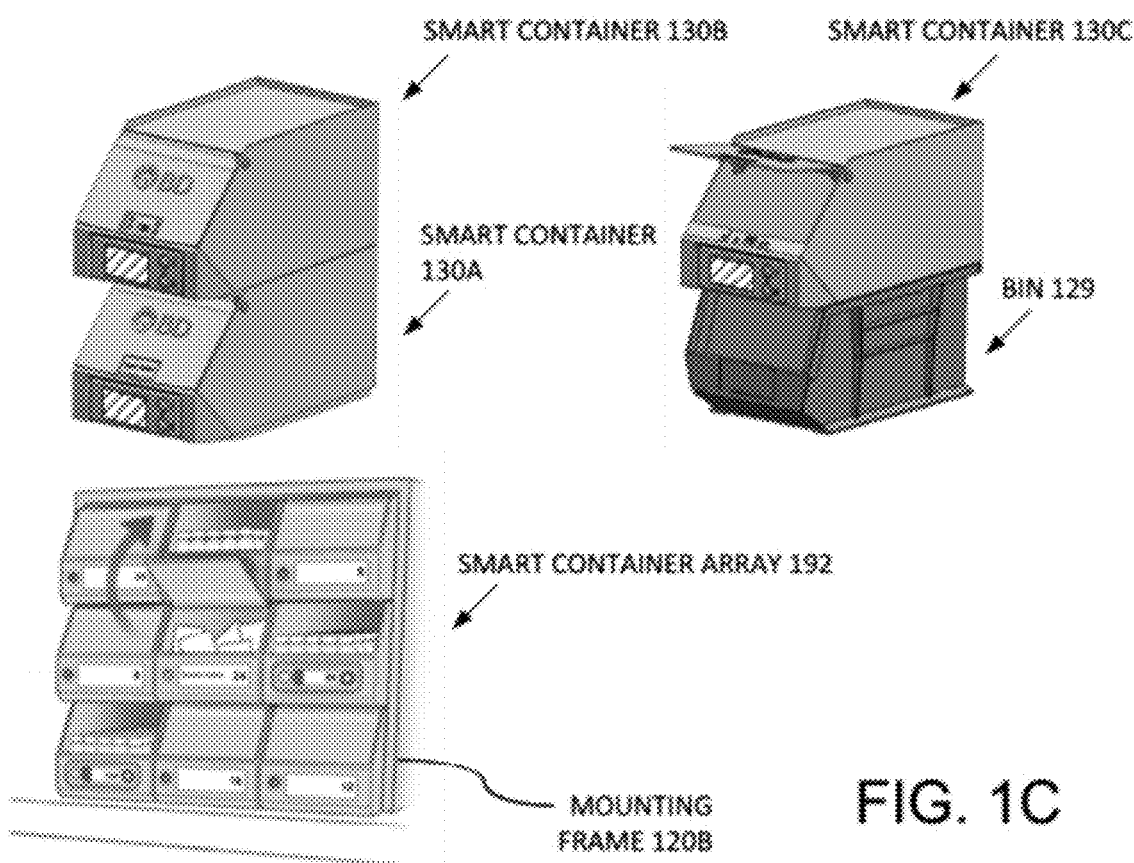
FIG. 1C depicts perspective views of example smart containers attached to other containers to form stacks or arrays, according to various aspects of the subject technology.

FIG. 1C depicts perspective views of smart containers attached to other containers to form stacks or arrays, according to various aspects of the subject technology. For example, as shown in FIG. 1C, interactive storage device 130B may stack on top of interactive storage device 130A, and may lock together using similar features as described above in conjunction with mounting frame 120A. Smart containers may also be configured to stack with existing off-the-shelf containers without smart functionality. For example, interactive storage device 130C may stack on top of bin 129. In some implementations, multiple smart containers may interlock into an array, such as smart container array 192. Smart container array 192 may further attach to mounting frame 120B to provide secure and space efficient item dispensing. For example, mounting frame 120B may be mounted to a wall or inside a cabinet. In some implementations, mounting frame 120B may swing out on a hinge or rail to provide facilitated access to the backside of smart container array 192. Mounting frame 120B may function as a docking station to provide power, network connectivity, and other resources for each smart container within smart container array 192. In this manner, the battery and other components within each smart container can be conserved for use during transportation and power outages.

While the smart containers shown in FIG. 1C may be shown as approximately uniform in size, other implementations may allow for smart containers of various sizes to be arranged in stacks and arrays in a similar fashion. For example, smart containers may scale to larger sizes that are multiples in width and height of a standard smart container, and these larger smart containers may interlock with different sized containers. For example, a double width container may support stacking of two standard width containers on top.

Figure 1D:
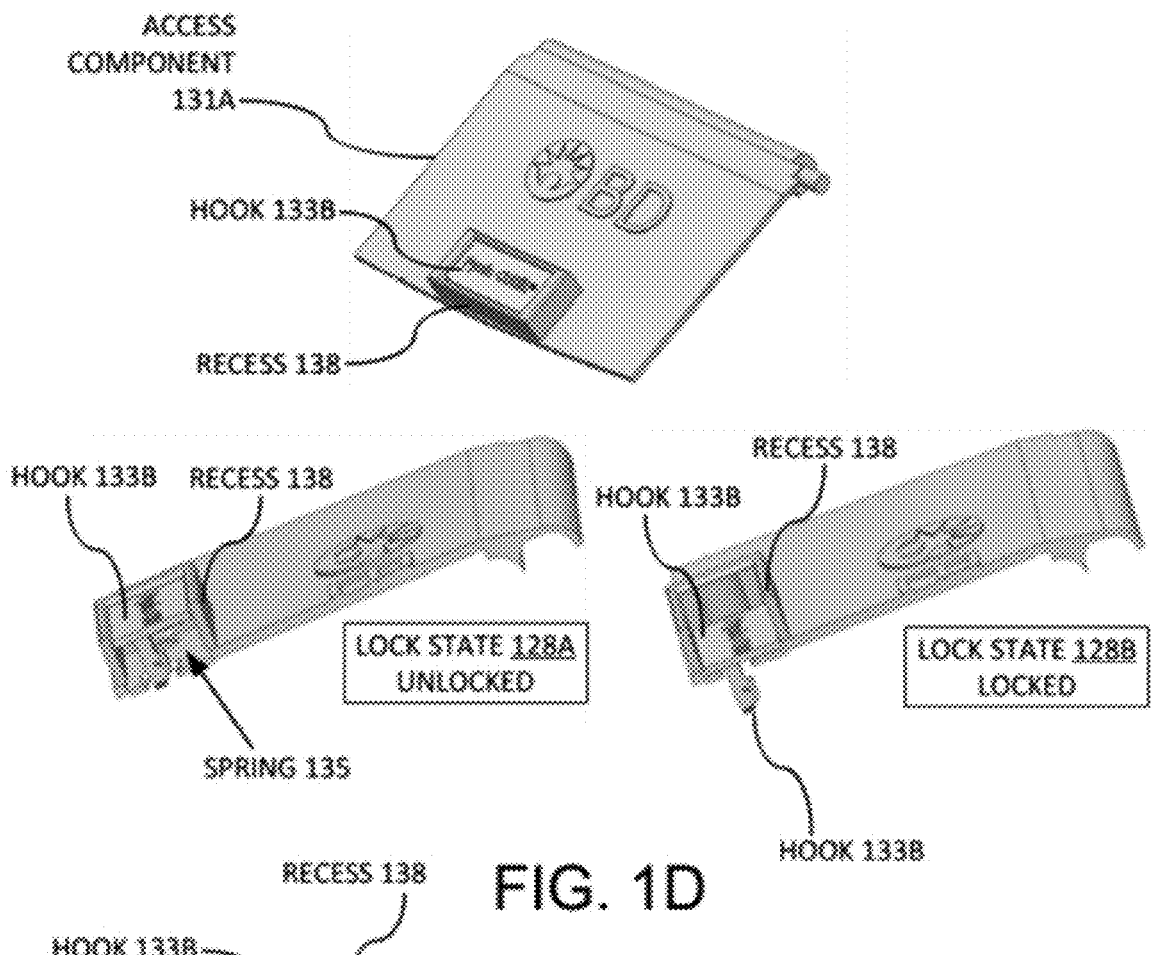
FIG. 1D depicts perspective and cut-away views of an example hinged lid with a spring loaded retractable fastening hook, according to various aspects of the subject technology.

FIG. 1D depicts perspective and cut-away views of a hinged lid, or access component 131A, with a spring loaded retractable fastening hook, or hook 133B, according to various aspects of the subject technology. Access component 131A includes a recess 138, allowing hook 133B to retract into recess 138 via spring 135 when hook 133B is disengaged from latch 126 (not shown in FIG. 1D), corresponding to lock state 128A in an unlocked state. The user may close a smart container by pushing onto hook 133B to engage with latch 126, corresponding to lock state 128B in a locked state. Spring 135 may therefore transition from an uncompressed state to a compressed state. Providing a retractable fastening hook advantageously allows the bottom or inner surface of access component 131A to be substantially flat without protrusions. Thus, users can more easily add or remove items without the risk of items or hands snagging onto hook 133B.

While access component 131A is shown to be opaque, some implementations may include a window portion that is translucent or transparent to allow a user to recognize the contents of a smart container at a glance. The window may be translucent to protect sensitive data, such as medication labels, from being casually read by an unauthorized user. In some implementations, display 165 may continuously display a textual or graphical depiction of the contents, as well as an estimated quantity, to further assist in user recognition of contents at a glance. In some implementations, the window may be include a variable transparency window such as a transparent light emitting diode (LED) window. The transparency may be controlled by a processor included in the interactive storage device 130B or communicatively coupled to the interactive storage device 130B. The transparency may be adjusted based on time of day (e.g., during hours when the room is being used, the window permits viewing but outside those hours, the window reduces transparency), detection of a condition near the interactive storage device 130B (e.g., a clinician authorized to put or take item from the interactive storage device 130B is detected within a threshold distance of the interactive storage device 130B; ambient light level to adjust glare or visibility into the interactive storage device 130B; or access state for another container near the interactive storage device 130B since a workflow including accessing one container may typically be followed by accessing the related container), or to communicate a status or location of the interactive storage device 130B (e.g., blink to guide a clinician to the container; change color or other graphic presentation to indicate need for servicing (e.g., latch malfunction, network failure, cleaning needed, inventory low), adjust graphic presentation to indicate other operational status of the smart container (e.g., battery low, network connection status, latch released, latch engaged, etc.). Such a window may be used to present or display other information or graphical interfaces such as those described in this application.

Figure 1E:
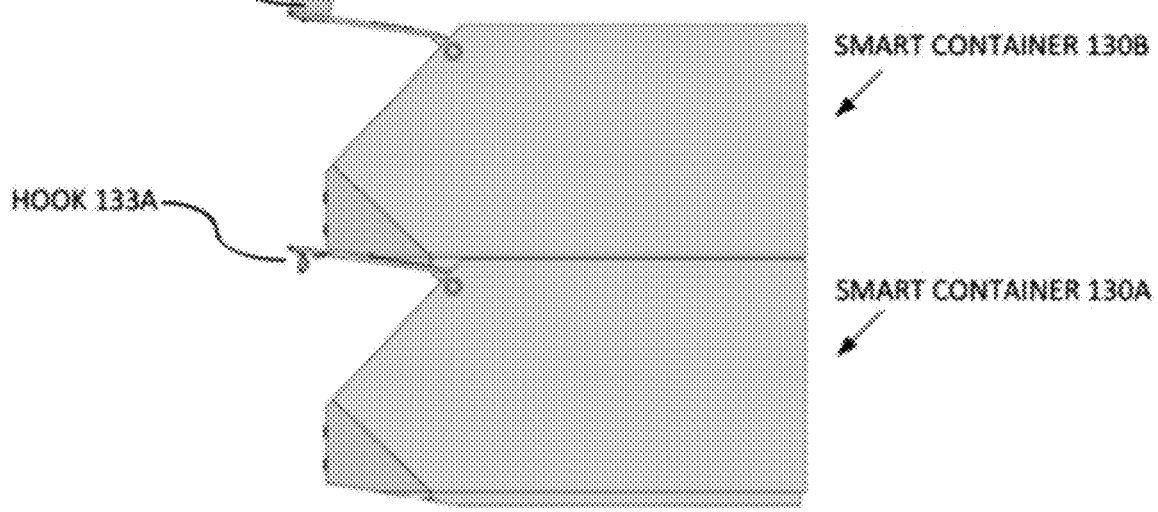
FIG. 1E depicts side views of example smart containers using retractable and non-retractable fastening hooks, according to various aspects of the subject technology.

FIG. 1E depicts side views of interactive storage device 130A using a non-retractable fastening hook, or hook 133A, and interactive storage device 130B using a retractable fastening hook, or hook 133B, according to various aspects of the subject technology. As shown in FIG. 1E, interactive storage device 130B provides unobstructed access to the internal compartment of interactive storage device 130B by retracting hook 133B into recess 138. On the other hand, interactive storage device 130A utilizes fewer parts, thereby reducing manufacturing and maintenance costs. Further, closing operations may be simplified as the user may push anywhere on access component 131A rather than specifically pushing hook 133B into latch 126. Accordingly, retractable or non-retractable fastening hooks may be utilized depending on specific use case requirements.

Figure 1F:
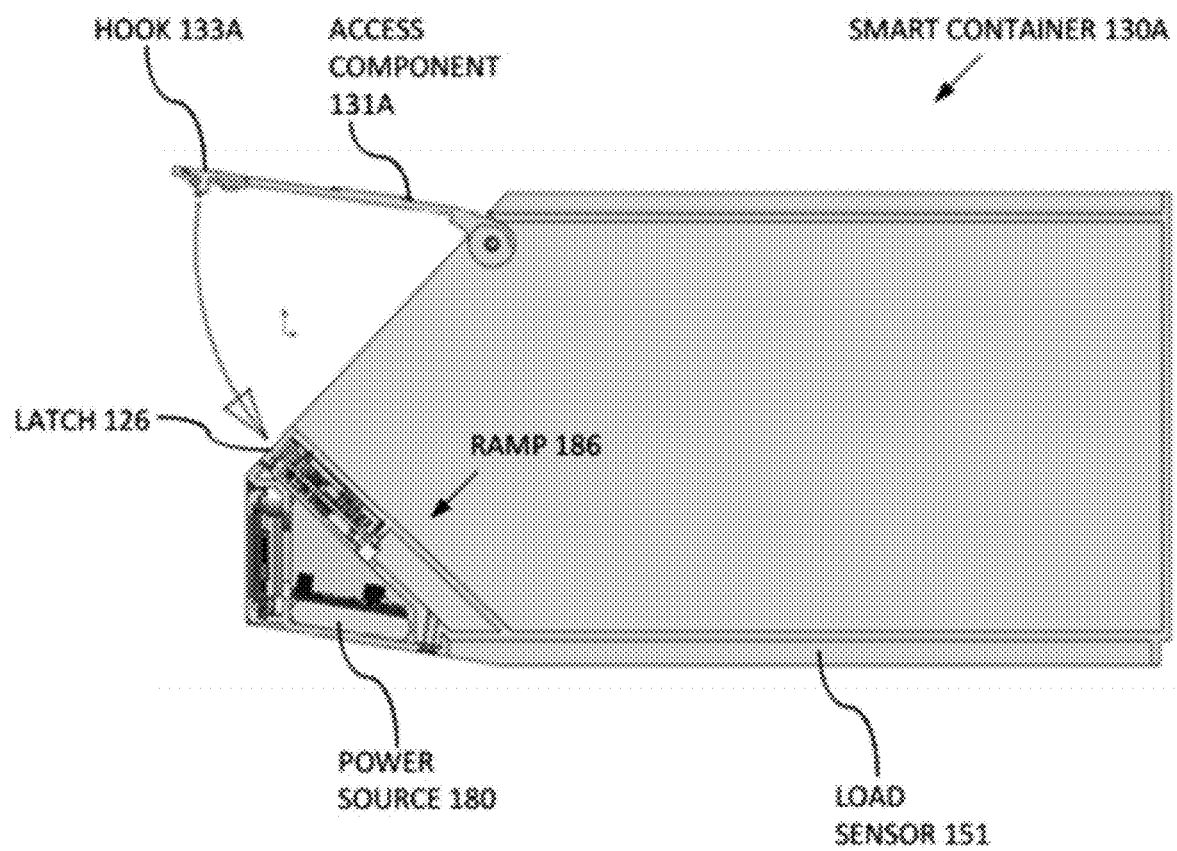
FIG. 1F depicts a cross sectional view of an example smart container, according to various aspects of the subject technology.

FIG. 1F depicts a cross sectional view of interactive storage device 130A, according to various aspects of the subject technology. The cross sectional view of interactive storage device 130A may be taken from a plane intersecting the center of interactive storage device 130A, wherein the plane may be parallel to the sides of the interactive storage device 130A. Interactive storage device 130 includes latch 126, access component 131A, load sensor 151, power source 180, and ramp 186. Access component 131A includes hook 133A. In some implementations, power source 180 may be accessible from outside, such as via a battery door compartment, to allow easy replacement of power source 180. In some implementations, a supplemental power source may be provided, such as a coin cell battery or super capacitor, for example to continuously power a real-time clock or other elements of interactive storage device 130A while power source 180 is exhausted or being replaced.

As shown in FIG. 1F, a load sensor 151 may be provided to measure the mass of items stored within the internal compartment of interactive storage device 130A. This can be used, for example, to estimate a quantity of items stored in interactive storage device 130A. Further, a sloped ramp, or ramp 186, may be provided for ease of item retrieval and storage. As described above, access component 131A may automatically swing out via a spring loaded hinge after hook 133A disengages from latch 126. To close interactive storage device 130A, the user may push down on access component 131A, as indicated by the arrow, such that hook 133A engages with latch 126. Portions of hook 133A may be configured to break away or dislodge into latch 126 when a user attempts to forcibly decouple hook 133A from latch 126. This provides evidence of an attempted diversion and further renders latch 126 inoperable. The intrusion attempt may also be recorded and transmitted to a backend server, allowing institutions to proactively monitor and prevent diversion.

Figure 1G:
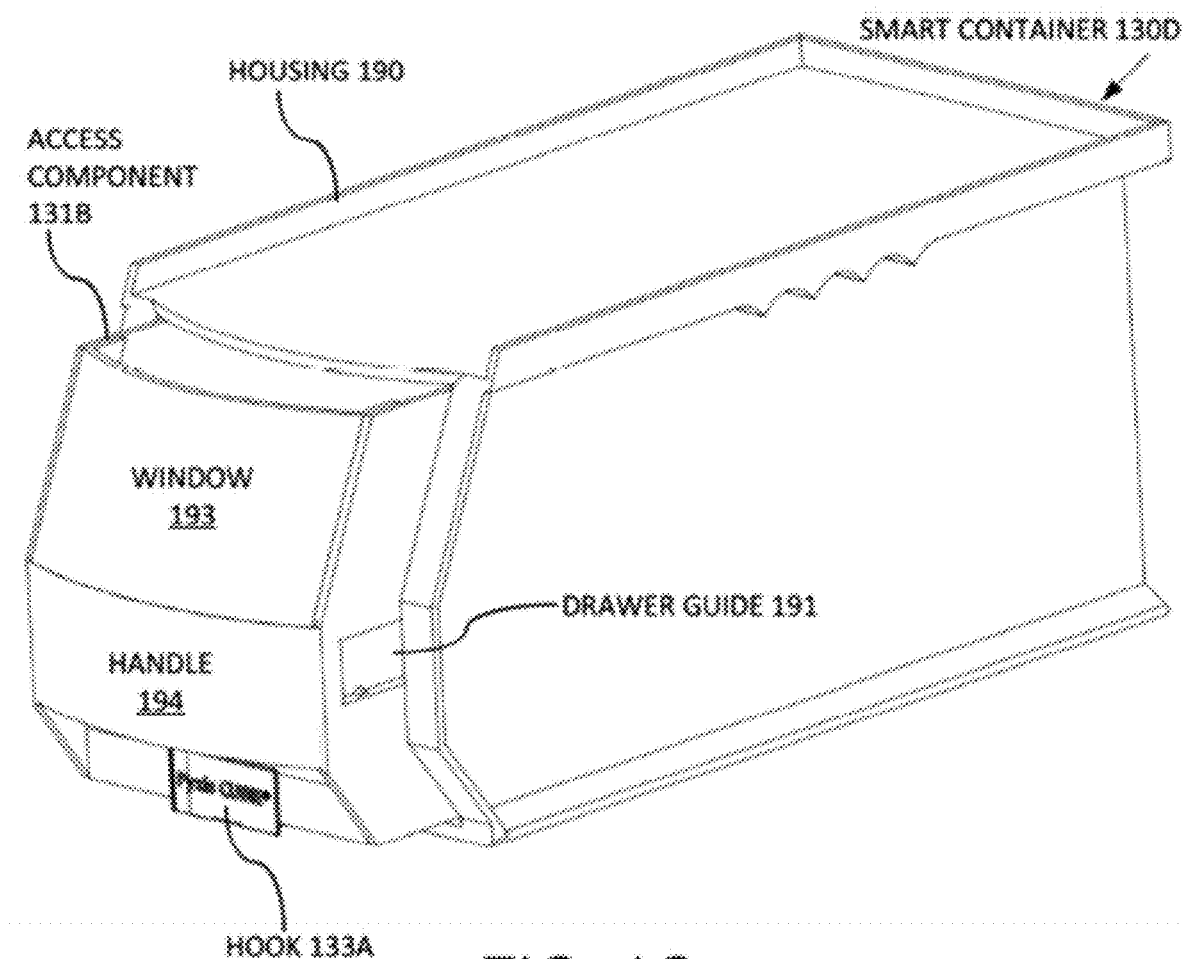
FIG. 1G depicts a perspective view of an example smart container with a sliding drawer, according to various aspects of the subject technology.

FIG. 1G depicts a perspective view of interactive storage device 130D with a sliding drawer, or access component 131B, according to various aspects of the subject technology. Interactive storage device 130D includes housing 190 and access component 131B. Access component 131B includes hook 133A, drawer guide 191, window 193, and handle 194.

In FIG. 1G, hook 133A may be decoupled from a corresponding latch, thereby providing access to the internal compartment of access component 131B. For example, the user may hold onto handle 194 to pull out access component 131B from housing 190. Drawer guide 191 may be placed on one or more sides of access component 131B to guide the movement of access component 131B within housing 190. Matching rails may be positioned within the interior of housing 190. Alternatively or additionally, rails may be included within drawer guide 191. Window 193 may be transparent or translucent to provide a view of the contents inside.

Figure 1H:
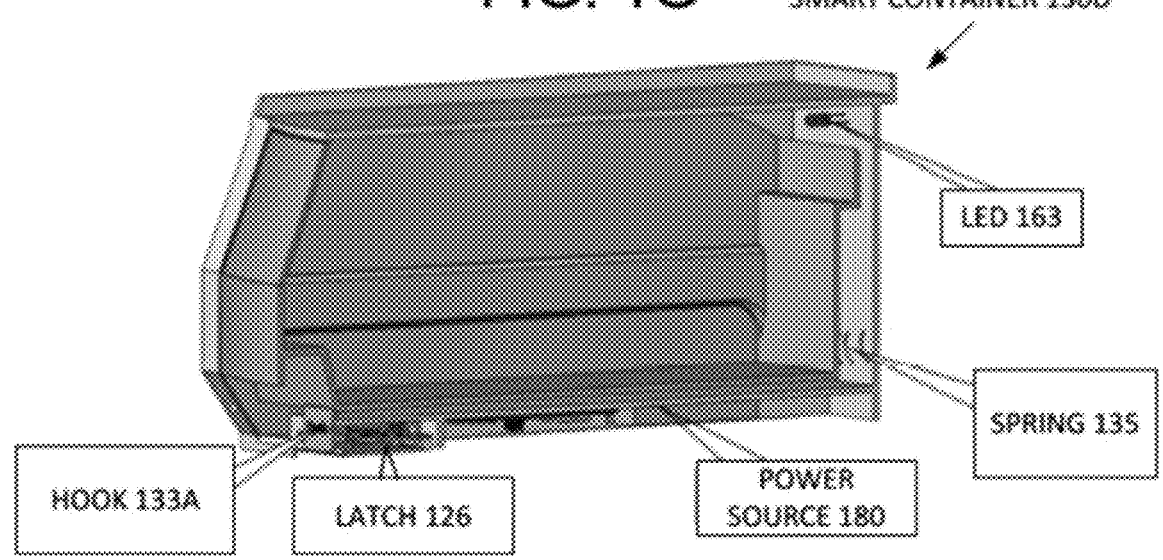
FIG. 1H depicts a cut away view of the smart container from FIG. 1G, according to various aspects of the subject technology.

FIG. 1H depicts a cut away view of interactive storage device 130D from FIG. 1G, according to various aspects of the subject technology. Interactive storage device 130D includes latch 126, hook 133A, spring 135, LED 163, and power source 180.

In FIG. 1H, hook 133A may be coupled to latch 126, thereby securing the internal compartment of access component 131B. Spring 135 may be provided to enable access component 131B to slide out automatically when hook 133A is decoupled from latch 126. In some embodiments, a motor or other device may be used to finely control the movement of access component 131B. For example, access component 131B can be moved to expose a specific depth of the internal compartment. This enables the internal compartment to be divided into multiple regions storing different types of items. LED 163 may provide status or identification to the user, and may be coupled to a light pipe or other device to allow LED 163 to be visible from window 193.

Figure 1I:
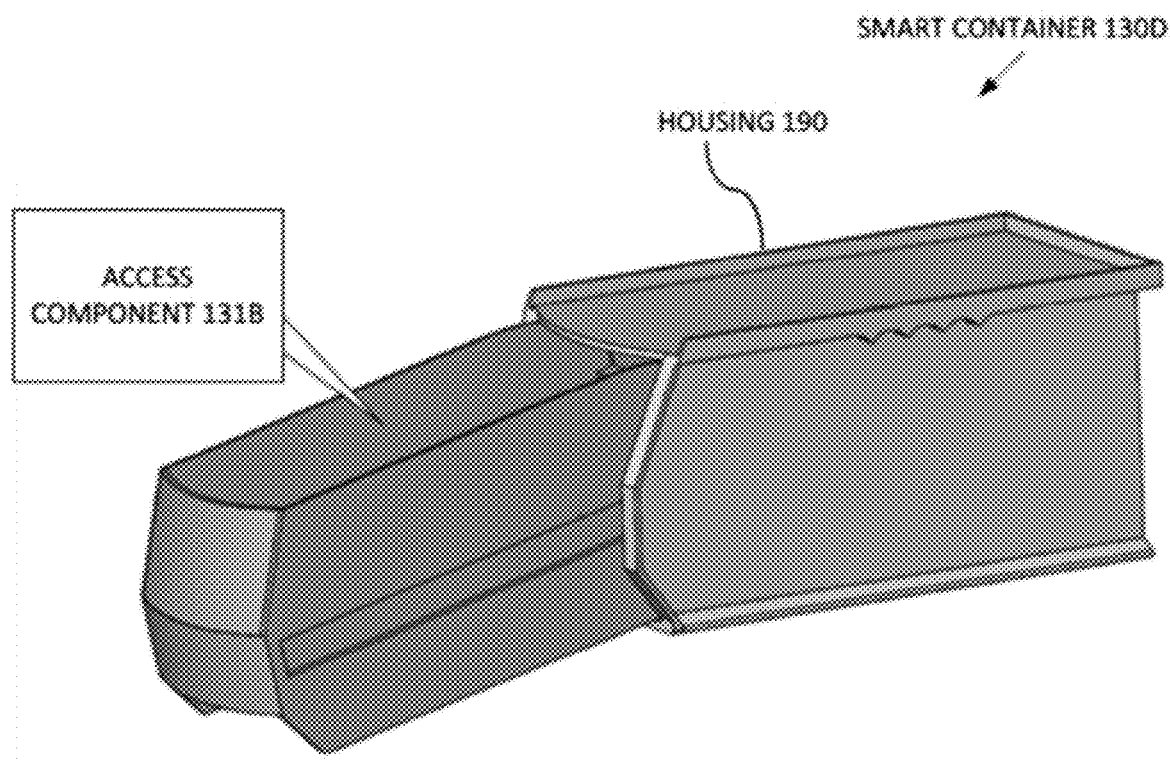
FIG. 1I depicts a perspective view of the smart container from FIG. 1G with a sliding drawer at a maximum extension, according to various aspects of the subject technology.

FIG. 1I depicts a perspective view of interactive storage device 130D from FIG. 1G with access component 131B at a maximum extension, according to various aspects of the subject technology. Housing 190 may include an internal stopper feature to stop access component 131B at a maximum extension, thereby preventing unintentional detachment of access component 131B from housing 190. The stopper may be configured to allow access component 131B to tilt downwards when at maximum extension, allowing the user to more easily view the entirety of the internal compartment.

With an overview of the smart container now in place, it may be helpful to observe the operation of multiple smart containers in an example networked environment. FIG. 2A depicts system 200 using smart containers 230A through 230G in networks 218 and 219 to provide automatic inventory management of items with inventory tracking 215, item condition tracking 216, and machine learning 217, according to various aspects of the subject technology. FIG. 2A includes care facility 210, server 214, network 218, and mobile mesh network 219. Care facility 210 includes patient room 211, supply room 212, smart container 230C, and smart container 230D. Patient room 211 includes smart container 230A, smart container 230B, and hub 290A. Supply room 212 includes smart container 230E, smart container 230F, smart container 230G, and hub 290B. Server 214 includes inventory tracking 215, item condition tracking 216, and machine learning 217. With respect to FIGS. 2A and 2B, each smart container 230A-230G may correspond to interactive storage device 130 or 130A-130D from FIG. 1A-1H.

Server 214 may use inventory tracking 215 to track an inventory of each uniquely identifiable smart container. Server 214 may connect to smart containers 230A-230G via network 218 and hubs 290A and 290B. Hubs 290A and 290B may be connected to an infrastructure network of care facility 210 having access to a public network, such as network 218, which may comprise the Internet. In some implementations, a cellular router, hub, gateway, modem, or another network device may be provided at hubs 290A and 290B or in each individual smart container 230A-230G to provide a connection to network 218. In this manner, the smart containers can be immediately deployed without requiring potentially costly and time consuming integration into existing information technology (IT) infrastructure at care facility 210.

A user may use a remote device, such as a tablet or smartphone, to request identification of a container storing a particular item, such as medication or medical supplies. The smart container may then identify itself to the user by outputting to an audiovisual element, such as by a blinking LED, emitting a sound, or a combination. The type of output may change depending on detected proximity to the remote device, for example by using beeps when the remote device/user is far away, and blinking LEDs when the remote device/user is nearby. For example, the user might use the remote device to request identification of alcohol wipes. The remote device may contact server 214, which in turn may query inventory tracking 215 to find a container containing alcohol wipes that is closest to the user. For example, the position of the user may be detected using GPS, or triangulated based on the proximity of hub 290B to the remote device. Inventory tracking 215 may identify alcohol wipes as being within smart containers 230D and 230G, and may therefore identify smart container 230G as being associated with the closest container to the user. As a result, server 214 may instruct smart container 230G to enter into an alert or identification mode, wherein a LED flashes white to guide the user to the container that contains alcohol wipes. In some implementations, the LED color may be specific to the user, as described above, to allow easy identification of multiple concurrent identifications.

As shown in system 200, each smart container 230A-230G may connect to network 218 using one of hub 290A or 290B, which may have an infrastructure or cellular connection to network 218. Since smart containers 230A-230G may be movable from one room to another, smart containers 230A-230G may potentially lose connection to hubs 290A and 290B. For example, smart containers 230C and 230D may be located too far away to connect to hub 290A or 290B. In this case, smart containers 230A-230G may provide mobile mesh network 219, wherein each smart container 230A-230G may function as a mesh node hop to facilitate a connection to hub 290A and 290B. When a route to server 214 is not immediately available, then a smart container may operate in an offline mode wherein inventory management is handled locally until a synchronization can occur with server 214 when a connection route is available.

In some implementations, each smart container may also track the location and inventory of other nodes in a local cache. In this manner, smart containers 230A-230G may query mobile mesh network 219 for the location of an item, instead of relying on server 214. Thus, each node in mobile mesh network 219 may periodically broadcast and propagate their own position and inventory to all other nodes, allowing a local cache of node locations and inventory to be stored by each node. In this manner, each node can quickly determine, from the local cache, the closest node where the requested item is possibly present. Since the local cache may be potentially out of date, a node may verify whether the requested item is actually still present by using mobile mesh network 219 to send a query to the closest node. The node may respond to the query with an indication of whether the item is present in the local inventory, and a location of the node. Once the closest node is determined, then a location of the closest node may be displayed on a map, e.g. on display 165 or on a display of a remote device. If the requested item is not present, then the node may respond by providing the last authorized user and access time, if available.

In this manner, devices connected to mobile mesh network 219 may cooperatively determine that the requested item is contained within a particular smart container. Thus, in some implementations, identification requests may propagate through mobile mesh network 219 to reach the correct node without the assistance of server 214, and information requests may similarly propagate to the correct node and forward a response to the original requesting node. In other implementations, server 214 may instruct the identified smart container to enter into an alert or identification mode, wherein a LED flashes white or a user-specific color to guide the user to the smart container. The remote device may also display a map to guide the user to the smart container. Further, any smart devices between the user and the destination may be directed to illuminate a path.

At server 214, inventory tracking 215, item condition tracking 216, and machine learning 217 may be queried and updated according to status information provided by each smart container. For example, inventory tracking 215, item condition tracking 216, and machine learning 217 may track the location, quantity, and condition of various medicines and healthcare items inside smart containers 230A-230G. Inventory tracking 215 may be updated to reflect items added or removed from containers. Item condition tracking 216 may be updated according to changing environmental conditions experienced by each smart container. Machine learning 217 may record device interactions and usage data for each smart container 230A-230G. Referring to FIG. 1A, the information stored in server 214 may be synchronized from data logs retrieved from non-volatile data store 137.

At least a portion of the smart container usage data may be processed by one or more machine learning algorithms to determine a power management profile that can be pushed back to smart containers 230A-230G for optimized power consumption. For example, the power management profile may define daily time periods when user interactions are infrequent. Smart containers 230A-230G may use this profile to transition the processor and other components to a low power idle or sleep mode during these daily time periods.

Each smart container may also support real-time status reporting when a network connection route is available. For example, a client may query server 214 for the status of a specific smart container. Assuming that server 214 can establish a network route to communicate with the requested smart container, the smart container may be queried for the requested status, such as environmental condition, location history, or local inventory status, and the smart container may respond by sending an encrypted message containing the requested status.

After arrival at a destination such as patient room 211, the smart containers 230A and 230B may be organized onto shelves, e.g. by attaching to a matching mounting frame as described above, and remain largely stationary until a restock is necessary. Since the smart containers 230A and 230B have a built in display 165 as shown in FIG. 1B, the display may continuously show both an item description and a quantity of items contained in an associated container. Referring to FIG. 1A, by using a low power display technology such as e-ink for display interface 164, battery life of power source 180 may be extended. Accordingly, a user can quickly identify the contents of each container at a glance without actually opening the container and looking closely at the contents. Additionally or alternatively, transparent or translucent windows may allow quick identification of items and remaining quantity. Thus, the stock level and battery level of each bin may be readily perceived and blinking LEDs or other audiovisual alerts may further bring attention to low stock, low battery levels, or item condition deterioration, allowing remedial action to be carried out early before problems arise. Accordingly, items can be kept well stocked and functional for smooth operation of care facility 210.

When multiple bins are stacked or arranged together or behind each other, then the multiple bins may be leveraged to help identify a target container. For example, as discussed above, the user may request the location of a particular item to be identified. Once a target container having the particular item is identified, multiple smart containers may be used to provide a visible path to the target container with the requested item. For example, containers in the same stack, the same array, or along a path to the target container may use a different light blinking pattern or color to distinguish themselves from the target container.

Figure 2A:
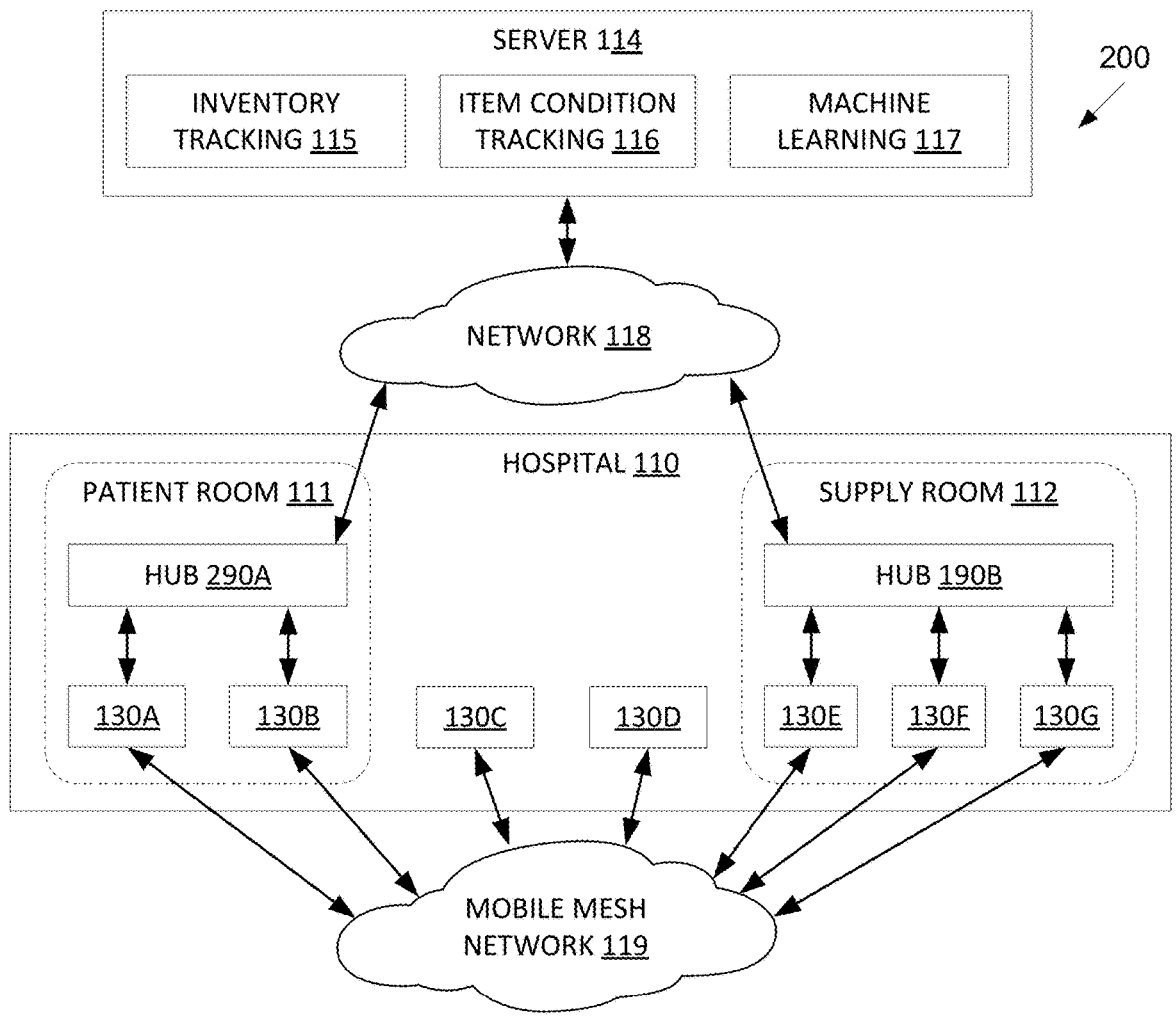
FIG. 2A depicts an example system including smart containers in an example network to provide efficient space utilization, secure transport and storage, inventory management, tamper resistance, and other smart functionality, according to various aspects of the subject technology.
Figure 2B:
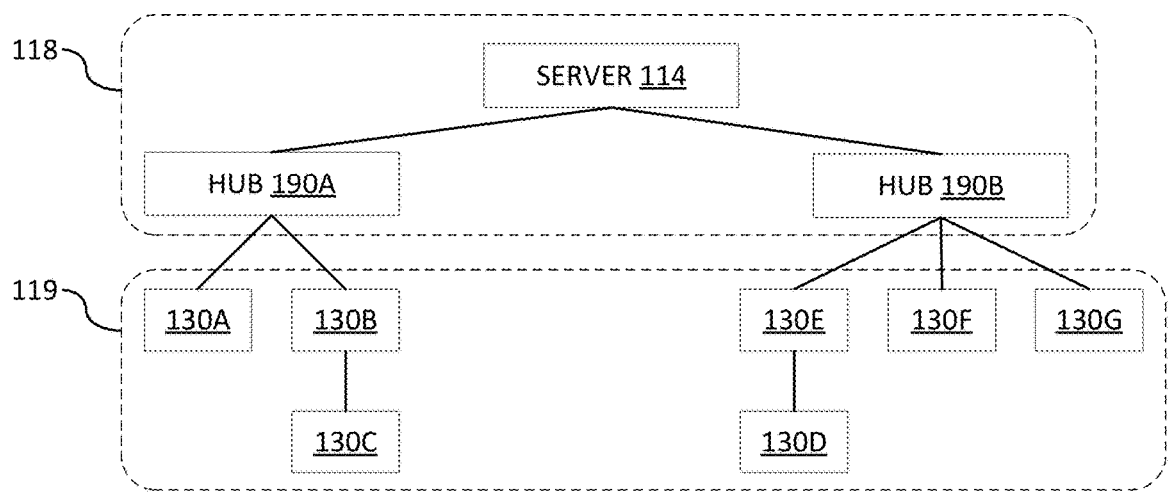
FIG. 2B depicts an example network topology diagram of the smart containers from FIG. 2A, according to various aspects of the subject technology.

FIG. 2B depicts an example network topology diagram of smart containers 290A-290G from FIG. 2A, according to various aspects of the subject technology. Network 218 may correspond to a public network such as the Internet, and server 214 may be connected to hub 290A and 290B. Mobile mesh network 219 may correspond to an ad-hoc mobile mesh network, wherein each individual node, or smart containers 230A-230G may physically move and disconnect and reconnect with each other according to radio reception to form a mesh network. Smart containers 230A-230B may connect directly to hub 290A, whereas smart container 230C may connect to hub 290A using smart container 230B as an intermediary node. Similarly, smart containers 230E-230G may connect directly to hub 290B, whereas smart container 230D may connect to hub 290B using smart container 230E as an intermediary node. Thus, nodes can act as master nodes (e.g. server 214), slave nodes (e.g. smart containers 230A, 230C, 230D, 230F, and 230G), or hybrid master/slave nodes (e.g. smart containers 230B, 230E and hub 290A, 290B).

FIG. 3 depicts various example user interfaces of a smart container, according to various aspects of the subject technology. With respect to FIG. 3, display 365A, display 365B, and display 365C may correspond to display 165 from FIGS. 1A and 1B. In some implementations, display 365A-365C may be shown on a remote device, such as a tablet, smartphone, laptop, or desktop computer.

Display 365A shows a status screen, which may be shown by default when no user interaction is taking place. As shown in display 365A, the status screen may include several informational fields, such as a description of item contents, a quantity, a battery level, a network status, and user interface instructions for using buttons 161 of FIG. 1B. Referring to FIG. 1A, the description and quantity may be updated according to a local inventory stored in non-volatile data store 137. The battery level may be updated according to estimated charge detected for power source 180. Network status may be updated according to the availability of connectable networks via communication interface 140. The user interface instructions may change depending on the user interface context. While display 365A-365C illustrate text representations, it should be understood that graphical representations such as icons, bars, charts, animations, and other elements may be shown.

As discussed above, in some implementations the smart container may be hardened to withstand refrigerated or freezing temperatures. In this case, as shown in display 365B, a temperature reading may also be provided. When the temperature reading exceeds a safe temperature range for the contents, a warning message or alert may be provided.

In some embodiments, a load cell or other sensor may be used to automatically estimate the quantity of items contained in each smart container. In this case, user interface elements to adjust item quantities, such as buttons 161, may be simplified or omitted. Accordingly, the status screen may also be correspondingly simplified to show essential information in large font, such as item description and quantity, as shown in display 365C. In this manner, contents within smart containers may be readily discerned from a distance and at a glance.

Figure 4:
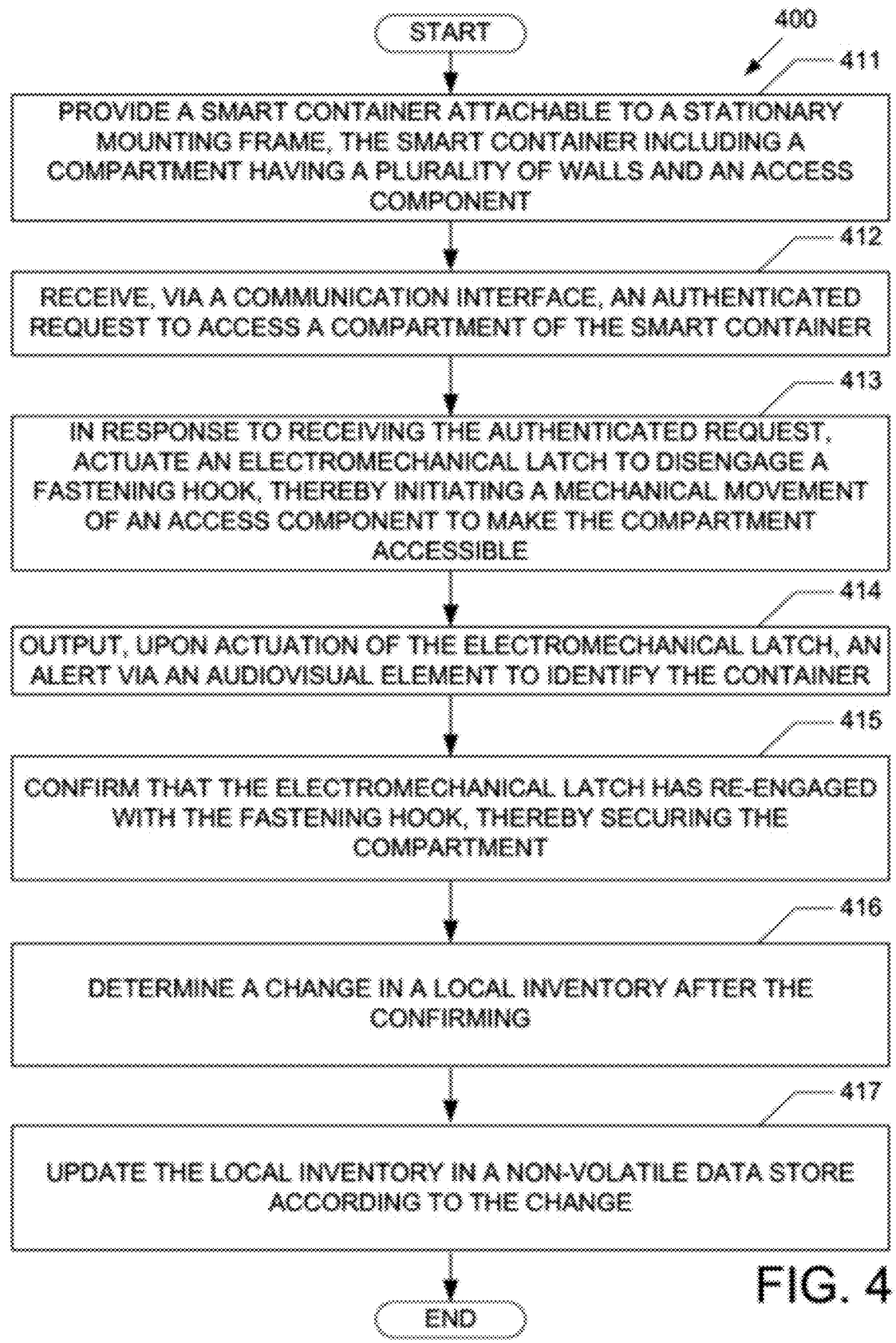
FIG. 4 depicts an example process for using a smart container to provide efficient space utilization, secure transport and storage, inventory management, tamper resistance, and other smart functionality, according to various aspects of the subject technology.

FIG. 4 depicts an example process 400 for using a smart container to provide efficient space utilization, secure transport and storage, inventory management, tamper resistance, and other smart functionality, according to various aspects of the subject technology. For explanatory purposes, the various blocks of example process 400 are described herein with reference to FIGS. 1A-3, and the components and/or processes described herein. The one or more of the blocks of process 400 may be implemented, for example, by a computing device, including a processor and other components utilized by the device. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, a smart container is provided that is attachable to a mounting frame, the smart container including a compartment having a plurality of walls and an access component (411). Referring to FIG. 1B, this may correspond to providing interactive storage device 130 that is attachable to mounting frame 120A, wherein interactive storage device 130 includes a compartment having a plurality of walls (e.g. on six sides) and access component 131A. As discussed above, interactive storage device 130 may also be attachable to other containers of various sizes to form stacks and arrays, such as smart container array 192 attachable to mounting frame 120B.

Process 400 may continue with receiving, via a communication interface, an authenticated request to access the compartment of the smart container (412). Referring to FIG. 1A and FIG. 2A, this may correspond to processor 134 receiving, via communication interface 140, an authenticated request for accessing interactive storage device 130. As discussed above, IAM interface 168 may utilize communication interface 140 to receive and authenticate a user credential, such as a unique identifier, a biometric identifier, or some other token, which may be received from a remote device, a smartcard, or some other device.

Processor 134 may validate or authenticate the user credential. For example, referring to FIG. 1A, processor 134 may utilize secure crypto-processor 184 to verify that the user credential is valid against an encrypted authorized user database. Alternatively, referring to FIG. 2A, processor 134 may utilize communication interface 140 to verify the user credential against server 214. In some implementations, the validation may further depend on temperature status or other logged data from sensors 150. For example, if the temperature exceeds a safe threshold range, then user access may be restricted to users with higher privilege levels. In this manner, potentially unsafe or spoiled medications may be kept safely locked until appropriate personnel can review the contents of the container.

In response to receiving the authenticated request, processor 134 may continue to actuate an electromechanical latch to disengage a fastening hook, thereby initiating a mechanical movement of an access component to make the compartment accessible (413). For example, referring to FIG. 1A and FIG. 1F, processor 134 may utilize actuator interface 166 to trigger actuator 167 to open latch 126. Once lock state 128 is set to open, then latch 126 may disengage from hook 133A, thereby causing access component 131A to swing outwards by rotating along the hinge. Access to the compartment of interactive storage device 130A is thereby provided. Similarly, referring to FIG. 1A, FIG. 1G and FIG. 1H, once lock state 128 is set to open, then latch 126 may disengage from hook 133A, thereby causing access component 131B to move outwards from housing 190 due to the stored energy in spring 135. Alternatively, a motor may be used to move access component 131B. Access to the compartment of access component 131B is thereby provided.

Upon actuation of the electromechanical latch, processor 134 may continue to output, via an audiovisual element, an alert to identify the container (414). For example, referring to FIG. 1A and FIG. 1B, processor 134 may use LED interface 162 and/or audio interface 170 to output flashing lights via LEDs 163 or audible tones via a piezoelectric or dynamic speaker. As discussed above, the colors, intensity, and flashing patterns of LEDs 163 may be adjusted according to the user associated with the access request.

Processor 134 may continue to confirm that the electromechanical latch has re-engaged with the fastening hook, thereby securing the compartment (415). For example, referring to FIG. 1F, the user may push down on access component 131A until hook 133A re-engages with latch 126. Similarly, referring to FIG. 1G and FIG. 1H, the user may push in access component 131B until hook 133A re-engages with latch 126. Referring to FIG. 1A, processor 134 may use actuator interface 166 to query actuator 167 and verify that lock state 128 of latch 126 now corresponds to a locked state.

After confirming, processor 134 may continue to determine a change in a local inventory (416). For example, referring to FIG. 1B, a user may utilize buttons 161 to adjust the quantity of items in the local inventory. In some implementations, items may include RFID tags, which may be detected using sensors 150. In some implementations, processor 134 may be communicatively coupled with a sensor that provides a measurement for use in determining the change in local inventory. For example, load sensor 151 may be provided. Based on the expected inventory, a theoretical weight may be generated and compared with the actual measured weight. If the theoretical weight after the expected inventory change corresponds to the actual weight, then the determination may be confirmed. If the determination is not confirmed, processor 134 may generate an alert message. The alert message may be displayed via display 165 or transmitted for presentation via another device.

Further, after determining the change in the local inventory, processor 134 may send, via communication interface 140, a stock notification to server 214 when a quantity of the local inventory is below a predetermined threshold level. For example, the predetermined threshold level may be set to 30% or 50% of a fully stocked container. In this manner, preparations for restocking may be made well in advance of stock depletion.

Processor 134 may continue to update the local inventory in a non-volatile data store according to the change (417). For example, based on the determined change, the local inventory stored in non-volatile data store 137 may be updated with correspondingly increased or decreased quantities.

In some implementations, processor 134 may continue to synchronize the local inventory with a remote server via a communication interface. For example, referring to FIG. 1A and FIG. 2A, processor 134 may synchronize the local inventory stored in non-volatile data store 137 with inventory tracking 215 stored on server 214 via communication interface 140. As discussed above, the local inventory may be received from smart devices within interactive storage device 130 that connect to a wireless repeater network provided by communication interface 140. In some cases, this synchronization may be deferred until a stable network route to server 214 is available. As discussed above, the smart container may form mobile mesh network 219 with other smart containers to improve network availability. The current location of the smart container may also be conveyed to server 214 based on triangulation using hubs or other location tracking methods.

In this manner, inventory tracking 215 can be automatically updated with the current location and inventory for each smart container, enabling detailed insight for medical supply restocking, loss prevention, and other management tasks. Similarly, item condition tracking 216 may be updated to track environmental conditions (e.g. whether safe temperature ranges are maintained) and item quality, and machine learning 217 may be updated with smart container usage statistics to provide training data for power management profile generation.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
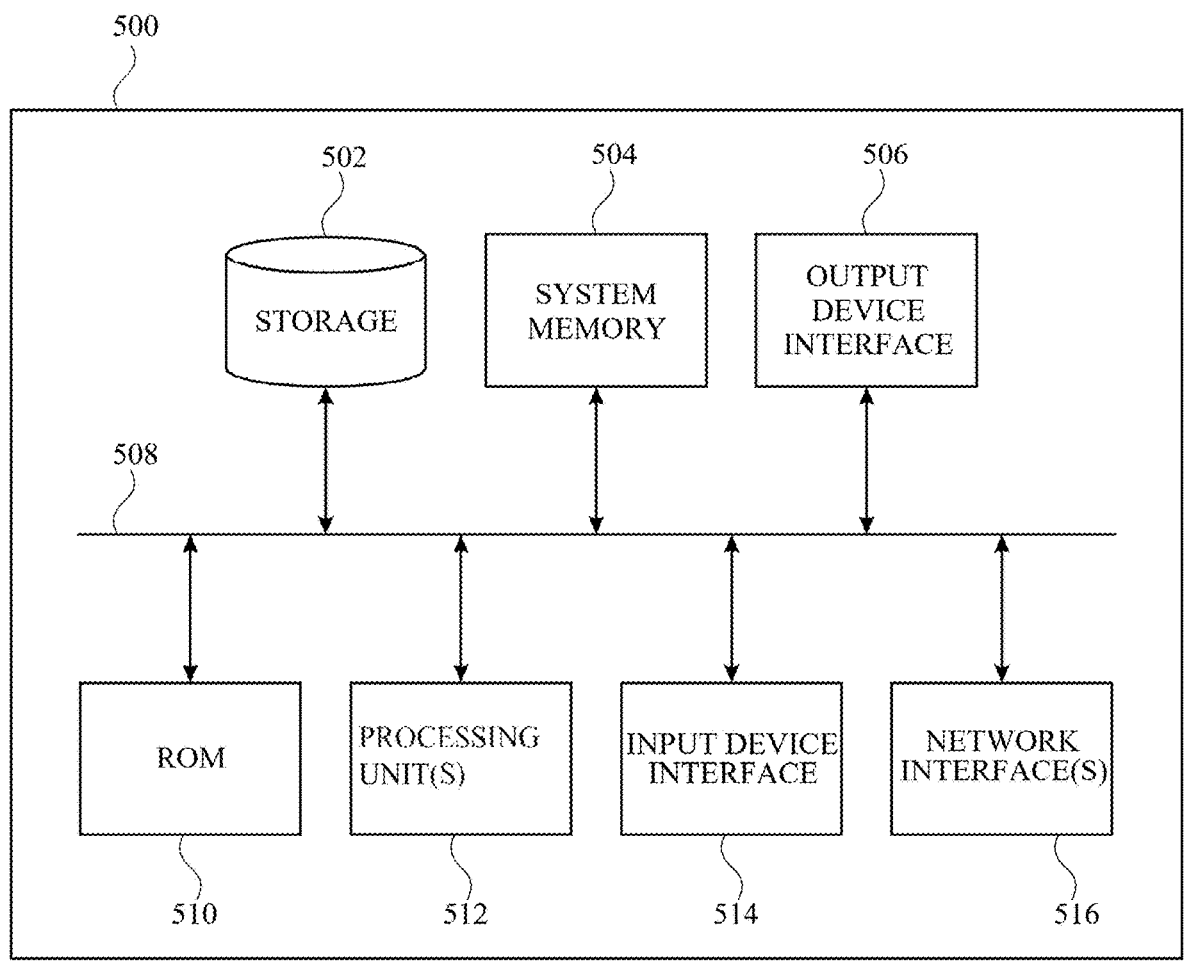
FIG. 5 is a conceptual diagram illustrating an example electronic system for providing a smart container for efficient space utilization, secure transport and storage, inventory management, tamper resistance, and other smart functionality, according to various aspects of the subject technology.

FIG. 5 is a conceptual diagram illustrating an example electronic system 500 for providing a smart container for efficient space utilization, secure transport and storage, inventory management, tamper resistance, and other smart functionality, according to various aspects of the subject technology. Electronic system 500 may be a computing device for execution of software associated with one or more portions or steps of process 400, or components and processes provided by FIGS. 1A-4. Electronic system 500 may be representative, in combination with the disclosure regarding FIGS. 1A-4, of the interactive storage device 130 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Some implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

As will be described further, the disclosed system 100, may include a bin assembly which incorporates a latching mechanism that can lock and unlock bins for secure storage. The latching member can engage and disengage a latching hook of the bin body to control access to the bin volume. An access controller can control when a bin is locked or unlocked based on one or more of user authentication, detected environmental condition, or control message from another device. By controlling access to the bin volume, inventory, such as medication, can be stored securely. The description of bin assembly, below, is understood as only an example of usage and does not limit the scope of the claims. Various aspects of the disclosed bin assemblies may be used in any application where it is desirable to securely store inventory.

Therefore, in accordance with the present disclosure, it is advantageous to provide a medication storage device as described herein that allows for space efficient and secure storage of regulated products, such as medication. The disclosed medication storage device provides a plurality of bins that permits configurable and secure storage of regulated products.

Secure Modular Bin Array

Another aspect of the disclosure relates to a slimline smart bin array system enables safe and secured medication management solution with a focus on optimizing the existing user space and resources ("slimline bin" or "slimline"). According to various implementations, the disclosed system includes configurable smart bins (different sizes), wireless connectivity, and an enclosure to hold the array of bins securely on a wall. The system and method may also include a plurality of user interfaces, along with actuator that unlocks the slimline bin with a secured authorization from a server. The system and method may further implement a machine learning (ML) inference and data analytics to optimize power consumption on the slimline bin based on its awareness of spatial context.

Figure 6:
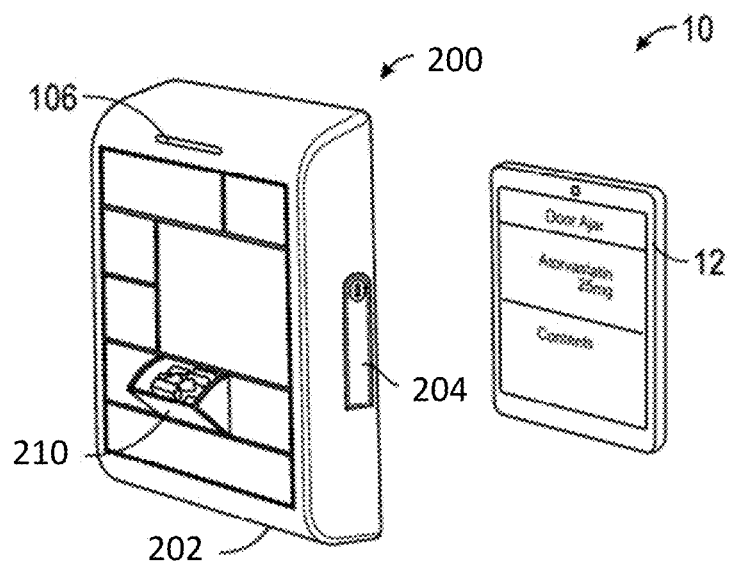
FIG. 6 is a perspective view of a medication management system, in accordance with various aspects of the present disclosure.

FIG. 6 is a perspective view of a medication management system 10, in accordance with various aspects of the present disclosure. With reference to FIG. 6, the medication management system 10 provides secure item storage and retrieval. As illustrated, the medication management system 10 includes a bin array assembly 200 with a plurality of connected bins 210 (e.g., bin 120 of FIG. 1A). As described herein, the bin array assembly 200 can include multiple bins 210 of different sizes.

In the depicted example, the bins 210 can secure store items such as medication or other regulated products. The bins 210 can be locked to prevent access. In some embodiments, selected bins 210 can be unlocked or otherwise released upon authentication of a user.

Optionally, the bins 210 can include a display, such as an e-ink display. The display can display information about the contents of a respective bin 210. In some embodiments, the bin 210 can present, via the display or other output device associated with the bin 210, a barcode to provide information to a clinician or other personnel. Information can include the medication name, dosage, and/or expiration date. In some embodiments, the display can illustrate the tracking status of an associated medication, displaying information such as "loading dock" or "in transit." The display for a bin or for an array of bins may be controlled by a microcontroller included in housing. The display may be controlled by a bin-specific microcontroller. In some implementations, the control may be achieved using a control message from a remote server such as an inventory management server.

In some embodiments, the bin array assembly 200 can include a status indicator 106. The status indicator 106 can display a plurality of colors at various intensities and flash patterns to provide a status of the medication management system 10. As can be appreciated, the status indicator 106 can provide different visual indicators based on an identified user and workflow. For example, (i) during a medication loading workflow, the status indicator 106 can provide guidance to the user, (ii) if medication within a bin 210 is expired, the status indicator 106 can flash red, (iii) during a medication audit, the status indicator 106 can provide identifying information, and (iv) if the battery level of the medication management system 10 is low, the status indicator 106 can provide a low battery signal. In some embodiments, the status indicator 106 includes one or more LED's driven by a FET based drive circuitry.

Optionally the medication management system 10 can include microphone interface circuitry to allow a user to interface with the medication management system 10 with "wakeup" words or voice prompts. In some embodiments, the medication management system 10 includes a piezo electric buzzer to provide audio feedback to the user.

In some embodiments, the components of the medication management system 10 can communicate with other components of the medication management system 10 or other systems. For example, the bins 210 can communicate with each other and the bin array assembly 200 can communicate with other bin array assemblies 200 to share inventory information, etc. In the depicted example, the bin array assembly 200 can wirelessly communicate with a control panel 12. The control panel 12 can be used to select or identify medication within the medication management system 10. The control panel 12 can identify a bin 210 containing a desired medication, as well as information regarding the medication. Optionally, the control panel 12 can be used for authentication purposes.

As illustrated, the bin array assembly 200 can be mounted to a wall surface to save space. In the depicted example, the bins 210 are interconnected and mounted to the wall via mounting frame 202. The mounting frame 202 can be vertically affixed to the wall and can receive the interconnected bins 210 forming the bin array assembly 200. The bin array assembly 200 can be locked or latched to the mounting frame 202 with a mounting mechanism 204. The mounting mechanism 204 can be a mechanical or electro-mechanical latch to engage with a portion of the bin array assembly 200. For example, the mounting mechanism 204 can includes one or more latching members or bars (not shown) that extend from the mounting frame 202 to releasably engage against the bin array assembly 200. In some embodiments, the mounting mechanism 104 includes one or more latching members or bars (not shown) that extend from the bin array assembly 200 to releasably engage against the mounting frame 202. By removing the bin array assembly 200, a user can have access to the rear of the bin array assembly 200. Optionally, a user can manually release bins 210 using a manual release mechanism disposed at the rear of the bin array assembly 200.

In some embodiments, the bin array assembly 200 can be mounted for counter top applications As can be appreciated, the medication management system 10 can be located in any suitable environment such as a medication room, a caregiver station, and/or a patient's bedside. In some embodiments, the medication management system 10 can withstand, and can be used in a refrigerated environment.

Figure 7A:
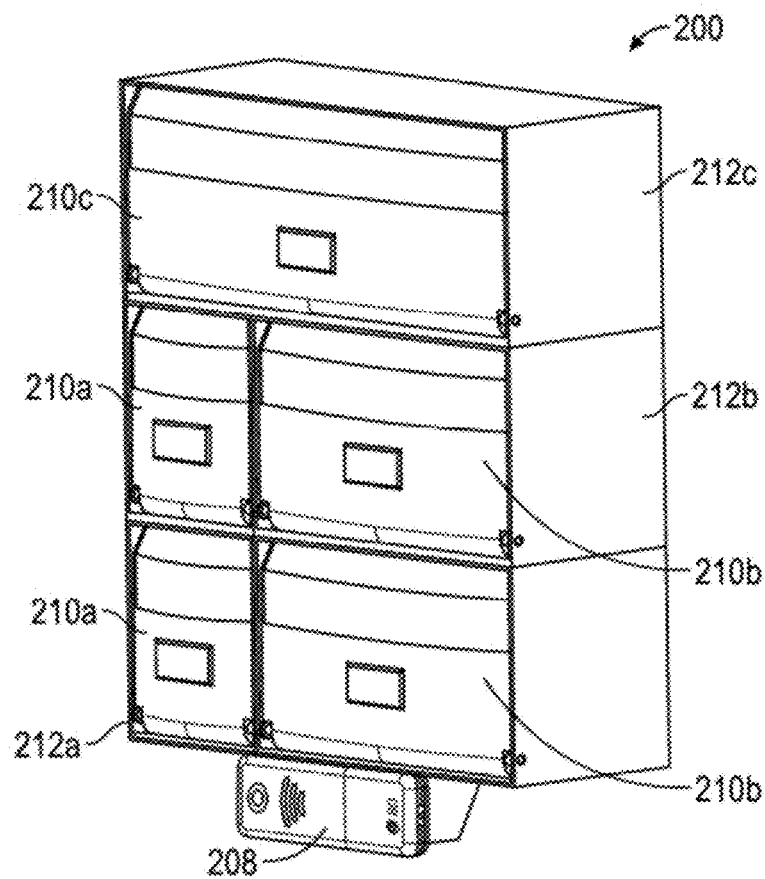
FIG. 7A is a perspective view of a bin array assembly for use with the medication management system of FIG. 6, in accordance with various aspects of the present disclosure.
Figure 7B:
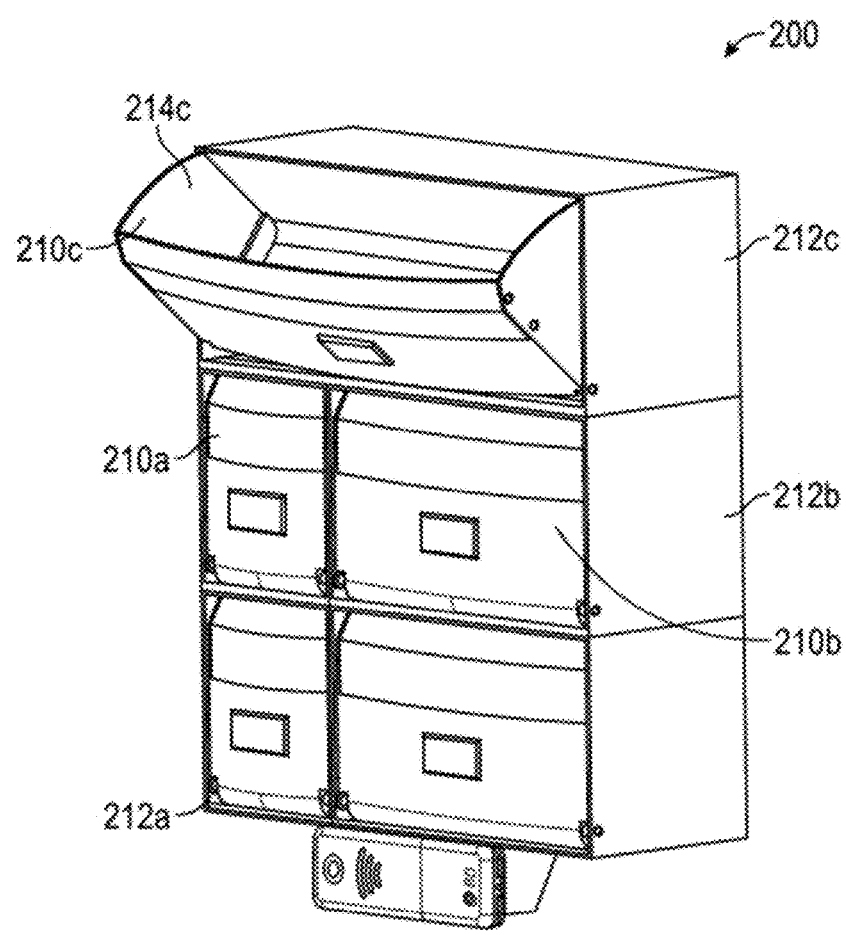
FIG. 7B is a perspective view of a bin array assembly of FIG. 7A with a bin in an open position, in accordance with various aspects of the present disclosure.

FIG. 7A is a perspective view of a bin array assembly 200 for use with the medication management system 10 of FIG. 6, in accordance with various aspects of the present disclosure. FIG. 7B is a perspective view of a bin array assembly 200 of FIG. 7A with a bin 210c in an open position, in accordance with various aspects of the present disclosure. With reference to FIGS. 7A and 7B, the bin array assembly 200 is a modular assembly of bins 210a, 210b, and 210c that allow configurable storage of medication and other items. As shown in FIG. 7B, a selected bin body 214c can be opened to expose the volume of the bin body 214c and access or replace items therein.

In the depicted example, the bins 210a, 210b, and 210c can be connected to each other in a modular manner to form the bin array assembly 200. The arrangement of bins 210a, 210b, 210c can form a generally rectangular shape or any other shape or pattern. In some embodiments, the respective bin housings 212a, 212b, 212c of the bins 210a, 210b, 210c have features or fasteners extending therethrough that allow the interconnection of the bins 210a, 210b, and 210c. Optionally, the bin housings 212a, 212b, 212c can have connection features on each of the sides, top and bottom, of the bins 210a, 210b, 210c.

In some embodiments, as described herein, the connection features of the bin housings 212a, 212b, 212c can be disposed towards the rear of the bin housings 212a, 212b, 212c. Further, hardware to control the operation (locking and unlocking) of the bins 210a, 210b, 210c can be disposed toward the rear of the bins 210a, 210b, 210c.

In the depicted example, an authentication device, such as a smartcard reader 208 can be used to direct and control access to the bins 210a, 210b, 210c by locking or unlocking an appropriate bin. In some embodiments, bins 210a, 210b, 210c of the bin array assembly 200 can be accessed using a personal computer, a tablet computer, a smartphone, a barcode reader, and/or a biometric reader.

During operation, the authentication device can provide a plurality of user authentication methods (biometric, smartcard, password, barcode, ECG based wearable device, mobile phone, etc.), allowing the user to select one or more of the authentication methods. The selection may be a user specific configuration, site specific configuration (e.g., all users at a given site will be authenticated according to the selected method(s)), or system-wide configuration (e.g., all users of the system will be authenticated according to the selected method(s)). The authentication device can utilize any suitable personal area network (PAN) protocols, such as 802.15.4, Bluetooth Low Energy, or other short-range compatible wireless communication protocol, to communicate with remote devices. In some embodiments, the use of PAN protocols can avoid integration with existing networks, simplifying installation.

Optionally, remote authentication methods can be implemented to allow a super user to grant remote authorization (e.g. if a user loses their badge or smart phone). In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computing or networked device, and the internet or including email transmissions and information recorded on websites and the like.

The user's authenticated identity can be transmitted to a server to request authorization to access a particular medication or item stored in a respective bin 210a, 210b, 210c. Upon receiving authentication, the bin 210a, 210b, 210c can be identified and/or unlocked for access. In some embodiments, authentication can proceed in an offline mode, allowing the user to proceed without network connectivity. In some embodiments, the authentication device can provide an audible signal (for example from a piezo beeper) to indicate registration of user actions.

Optionally, sensors can be utilized within the bins 210a, 210b, 210c to identify the quantity of the contents within each bin 210a, 210b, 210c. In some embodiments, beacons can be used for real time and/or offline asset tracking. Further sensors can be utilized for tamper detection of the bin array assembly 200.

Sensors included in a bin may include one or more sensors to record, for example, environmental conditions and evidence related to attempts to divert or tamper with the contents of the bin. For example, a load sensor may comprise a load cell that can measure the mass of items contained in the bin, which can be used to estimate changes in item quantities. A temperature and humidity sensor may record inside and/or outside ambient temperature and humidity. A shock and vibration sensor may help to identify unauthorized access attempts to the bin using force. A tamper sensor may determine whether intrusion has occurred or if the bin has been removed from a fixture, for example if retaining screws, containers, covers, or other components of bin have been opened, unsealed, drilled, deformed, or otherwise tampered. For example, mechanical switches, anti-tamper films, photodiodes with reflective materials, infrared proximity sensors, and other devices may be used. A location sensor may include, for example, a global positioning system (GPS) radio to enable location history tracking. Alternatively or additionally, in some implementations, triangulation may be used to determine location, for example by using Wi-Fi or Bluetooth triangulation using known networks and/or hubs.

Figure 8:
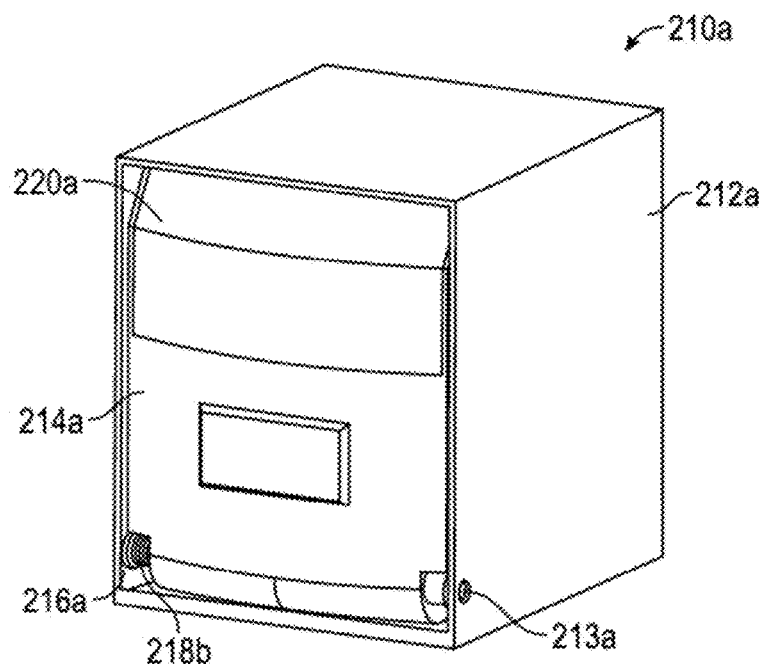
FIG. 8 is a perspective view of a bin for use with the bin array assembly of FIG. 7A, in accordance with various aspects of the present disclosure.

FIG. 8 is a perspective view of a bin 210a for use with the bin array assembly 200 of FIG. 2A, in accordance with various aspects of the present disclosure. As can be appreciated, the bin 210a is an example of a representative bin that can be used with the bin array assembly 200. As can be appreciated, the bin array assembly 200 can utilize similar bins that are of single width (FIG. 14), double width (FIG. 15A), and/or triple width (FIG. 15B). The housing 212a can include mounting features along the outer surface of the housing 212a that engage with or otherwise interface with similar or mating features on neighboring bins 210a.

Figure 10A:
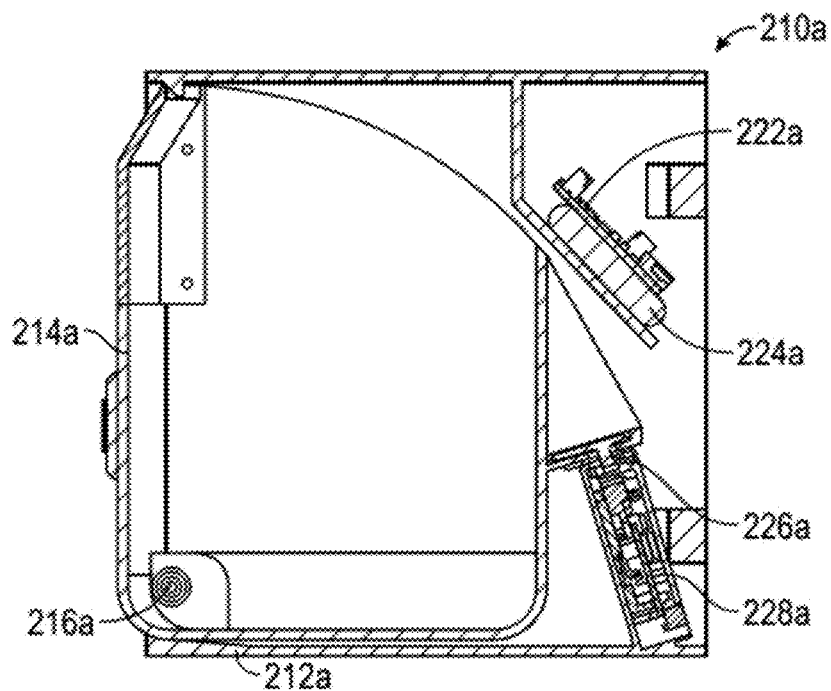
FIG. 10A is a cross-sectional elevation view of the bin of FIG. 8 in a closed position, in accordance with various aspects of the present disclosure.
Figure 10B:
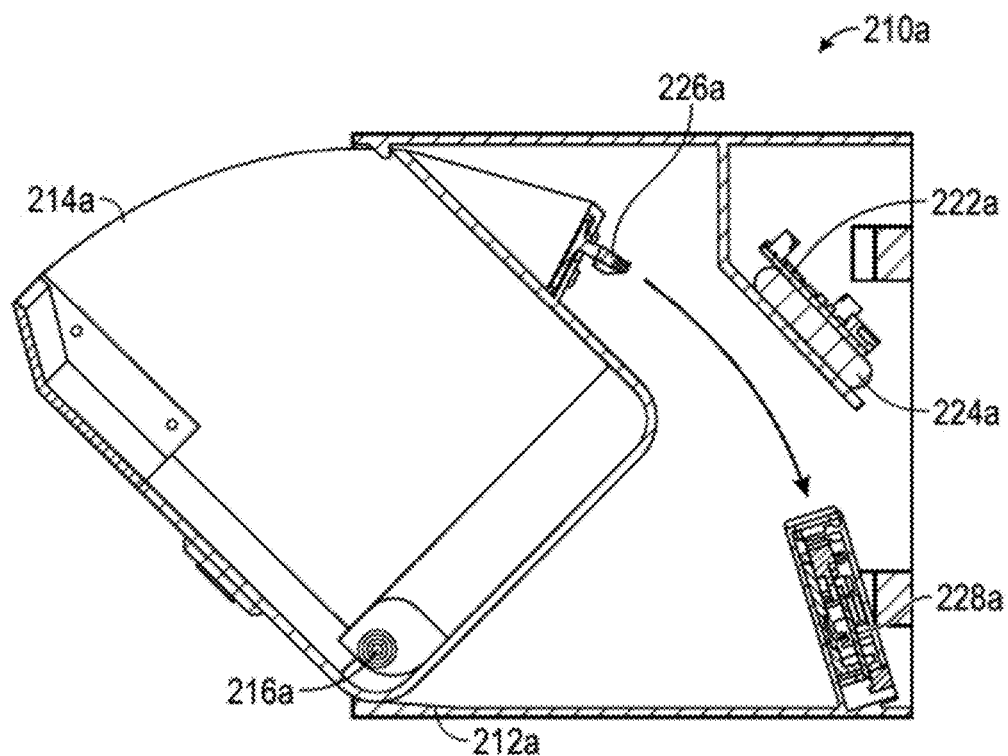
FIG. 10B is a cross-sectional elevation view of the bin of FIG. 8 in an open position, in accordance with various aspects of the present disclosure.

In the depicted example, the bin body 214a is movable relative to the housing 212a. During operation, the bin body 214a can be moved between a closed position (FIG. 10A) and an open position (FIG. 10B). In the closed position, access to the volume defined by the bin body 214a is prevented by the housing 212. In the open position, the bin body 214a is moved away from the housing 212a permitting access to the volume defined by the bin body 214a.

As illustrated, the bin body 214a can pivot or tilt relative to the housing 212a to allow the user to access to medication. In some embodiments, the bin body 214 is connected to the housing 212a by a pivot pin 216a extending from the bin body 214a. The pivot pin 216a can extend through a through hole 213a formed through the housing 212a. In some embodiments, the pivot pin 216a and the through hole 213a can be disposed near the front portion of the bin 210a, allowing the bin body 214a to pivot or rotate forward to allow access within the bin body 214a.

Optionally, the bin body 214a can be biased toward an open position or a closed position by a biasing member or spring 218a. In some embodiments, the spring 218a can bias the bin body 214a forward relative to the housing 212a to the open position. The spring 218a can be a rotational spring that is disposed around the pivot pin 216a. As described herein, upon unlatching or unlocking the bin 210a, the spring 218a can rotate the bin body 214a to an open position to visually indicate the bin 210a to be accessed. The bin 210a can further include a rotational stop to prevent the bin body 214a from over rotating.

In some embodiments, the bin body 214a can include a window 220a. The window 220a can allow a user to identify the contents of the bin body 214a prior to accessing the bin volume. In some embodiments, the window 220a can be clear. Optionally, the window 220a can be translucent, allowing a user to identify that the bin body 214a contains items, but obscuring details of the items.

In some embodiments, the bin 210a can include tracking or identifying features such as bar codes. The bin 210a can further include tamper evident features.

Figure 9:
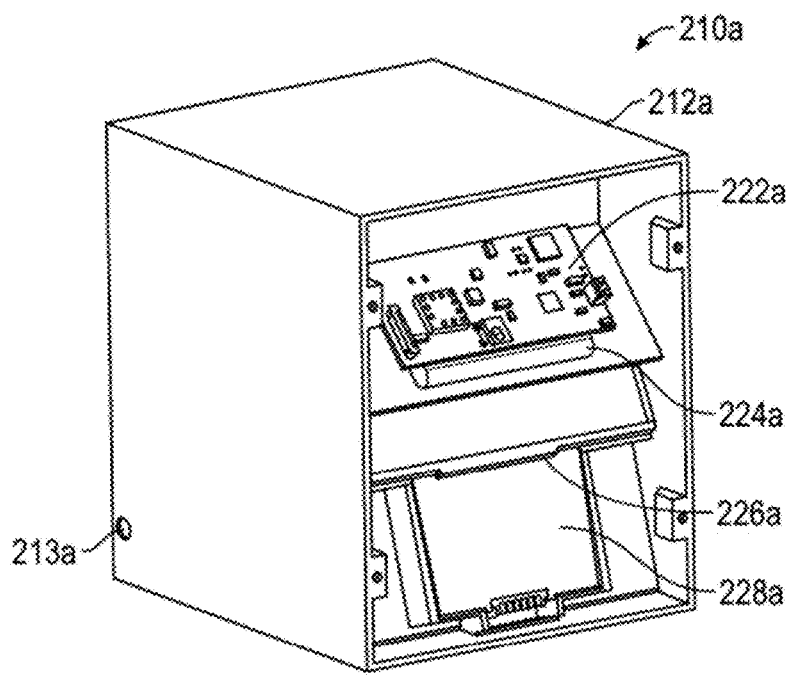
FIG. 9 is a reverse perspective view of the bin of FIG. 8, in accordance with various aspects of the present disclosure.

In some implementations, FIG. 9 is a reverse perspective view of the bin 210a of FIG. 8, in accordance with various aspects of the present disclosure. FIG. 10A is a cross-sectional elevation view of the bin 210a of FIG. 8 in a closed position, in accordance with various aspects of the present disclosure. FIG. 10B is a cross-sectional elevation view of the bin 210a of FIG. 8 in an open position, in accordance with various aspects of the present disclosure. With reference to FIGS. 9, 10A, and 10B, the bin 210a includes a latching mechanism to control access to the bin 210a.

In the depicted example, an electromechanical (EM) latch 228a can latch or unlatch the bin body 214a, locking or unlocking the bin 210a for access. The EM latch 228a can be mounted to the housing 212a. As illustrated, the EM latch 228a can be mounted to a rear portion of the housing 212a. In some embodiments, the EM latch 228a can engage with a portion of the bin body 214a to prevent movement of the bin body 214a (locking the bin 210a, as shown in FIG. 10A) and protecting the contents within the bin body 214a.

In some embodiments, the bin body 214a includes a latch hook 226a extending from the bin body 214a. The latch hook 226a can be received into the EM latch 228a. Optionally, the latch hook 226a can be engaged by a latching member within the EM latch 228a to lock the bin 210a.

With reference to FIG. 10B, to release or unlock the bin 210a, the EM latch 228a can release the engaged portion of the bin body 214a to allow the bin body 214a to move (unlocking the bin 210a). Optionally, the latch hook 226a can be disengaged from the latching member within the EM latch 228a. In some embodiments, the operation of the EM latch 228a, including the movement of the latching member can be electromechanically actuated.

Upon releasing or unlocking the bin 210a, the bin body 214a can be rotated or tipped outward to allow retrieval of the contents within the bin 210a. The opening of the bin body 214a at the maximum opening angle allows the user unobstructed access to the contents. Optionally, the bin body 214a can be biased toward an open position upon release of the EM latch 228a. After accessing the contents of the bin 210a, the bin body 214a can be rotated or pivoted back toward a closed position. As the bin body 214a is moved back to a closed position, a portion of the bin body 214a, such as the latch hook 226a can interface and engage with the EM latch 228a, relocking the bin 210a.

In the depicted example, the operation of the EM latch 228a is controlled by a controller 222a. During operation, the controller 222a can drive the actuators within the EM latch 228a and determine the current state of the EM latch 228a and the bin 210a. In some embodiments, the controller 222a can have on-board memory to digitally store information regarding the bin 210a contents and/or location information.

Optionally, the controller 222a can be operatively coupled with sensors to determine the status of the bin 210a and/or contents within the bin 210a. For example, the bin 210a can include a sensor to determine the open/closed state of the bin body 214a. In some embodiments, the bin 210a can include tamper detection sensors that utilize optical or electromagnetic sensors. Optionally, the status or quantity of the contents within the bin 210a can be determined with load cells, photodiodes, acoustical sensors, and/or RF sensors.

In some embodiments, the EM latch 228a and/or the controller 222a can be battery 224a operated or otherwise powered by a power source. Power sources can include distributed power sources, such as rechargeable batteries, super capacitors, or wireless power transmitters/receivers, or centralized power sources, such as centralized high capacity batteries, an external power supply, power over Ethernet, and/or wireless power transmitters/receivers. As can be appreciated, centralized power sources can be interfaced to the bin array assembly 200 with a docking type or wired physical connector to redistribute power to the bins 210a. Wireless power transfer can include near field (such as NFC, Qi, Resonant and inductive) or far field (such as WiFi, UHF). Wireless charging schemes can be multiplexed as only one bin 210a is accessed at a given time within the assembly 200. In some embodiments, guided lights or mechanical features are used to dock the bins 210a for wireless charging.

Optionally, power conservation methods can be used, such as placing devices in low power states and waking up periodically to enable radio communications and check in with a gateway or hub for updates or transactions. Environmental sensors, key word activation, and/or user actions, along with usage factors can be used to wake a device up form sleep mode. Further, devices can utilize energy harvesting. Energy harvesting can include harvesting from actuator action and/or wireless energy from RF sources.

In some embodiments, the electronics of the bin 210a are modular and associated with each bin. In some embodiments, the electronics of the bin 210a are centralized.

Optionally, the bin 210a can include tamper resistant features or interlocks. For example, the bin 210a can have overlapping features that prevent an unauthorized user from accessing the contents of an adjacent bin after gaining access to one bin. Portions of the bin 210a may deform to indicate evidence of tampering. For example, the latch hook 226a may be configured to break inside the EM latch 228a if excessive force is applied, rendering the bin 210a unusable.

Figure 11:
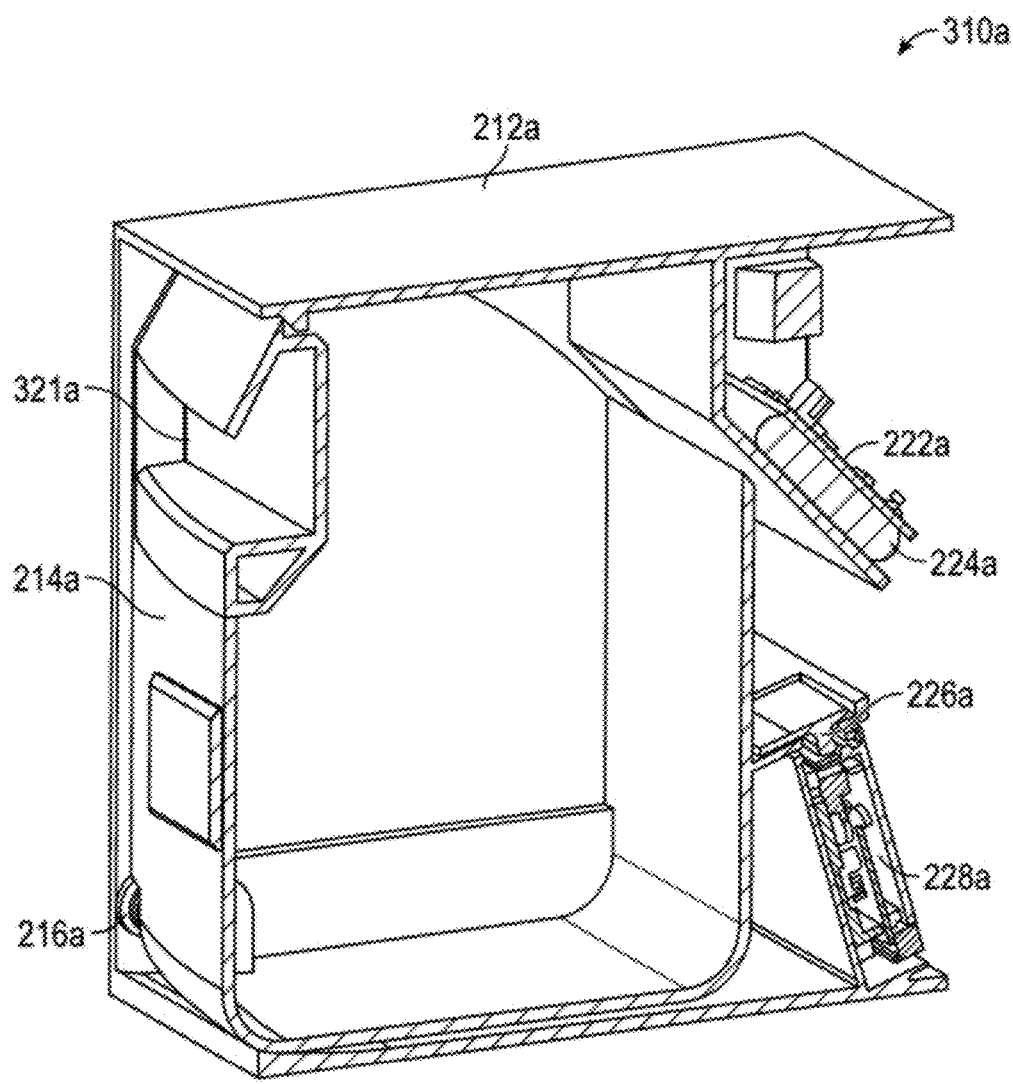
FIG. 11 is a cross-sectional perspective view of a bin for use with the bin array assembly of FIG. 7A, in accordance with various aspects of the present disclosure.

FIG. 11 is a cross-sectional perspective view of a bin 310a for use with the bin array assembly 200 of FIG. 7A, in accordance with various aspects of the present disclosure. In the depicted example, the bin 310a includes features that are similar to the features of bin 210a. Therefore similar features are referred to with similar reference numerals.

As illustrated, the bin 310a includes a handle 321a. The handle 321a can be formed as a recessed area in the bin body 214a. As can be appreciated, the bin 310a can be used without a biasing spring because the user can use the handle 321a to rotate or pivot the bin body 214a away from the housing 212a.

Optionally, the bin 310a can include one or more visual indicators to indicate the bin 310a to the user. The visual indicator can be an LED to visually indicate the location of the contents and the bin 310a.

Figure 12A:
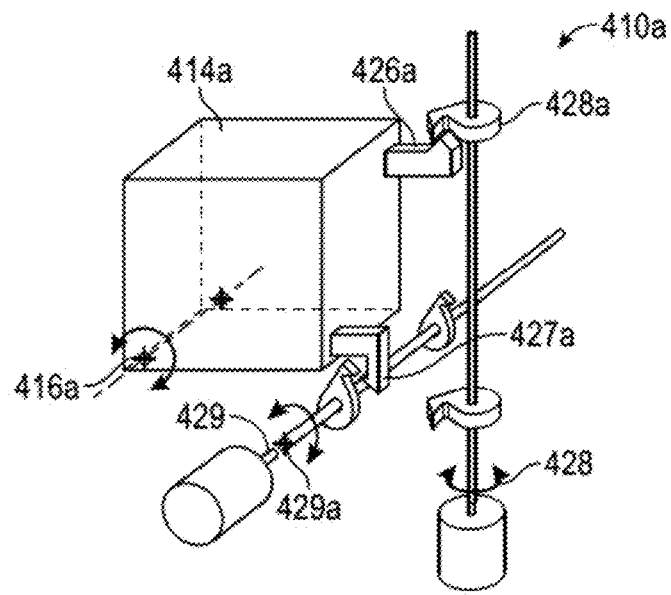
FIG. 12A is a reverse perspective view of a bin for use with the bin array assembly of FIG. 7A, in accordance with various aspects of the present disclosure.
Figure 12B:
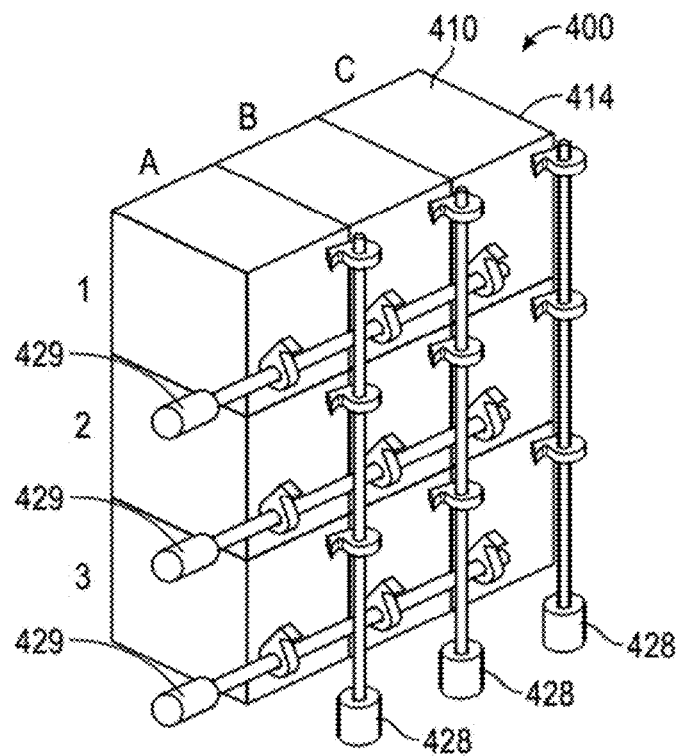
FIG. 12B is a reverse perspective view of a bin array assembly for use with the medication management system of FIG. 1, in accordance with various aspects of the present disclosure.

FIG. 12A is a reverse perspective view of a bin 410a for use with the bin array assembly of FIG. 7A, in accordance with various aspects of the present disclosure. FIG. 12B is a reverse perspective view of a bin array assembly 400 for use with the medication management system 10 of FIG. 1A and FIG. 6, in accordance with various aspects of the present disclosure. In the depicted example, the bin array assembly 400 includes features that are similar to the features of the bin array assembly 200 and the bin 410a includes features that are similar to the features of bin 210a. Therefore similar features are referred to with similar reference numerals.

In the depicted example, the bin array assembly 400 can utilize common latching mechanisms 428 and 429 to latch or unlatch a plurality of bins 410, while allowing individual locking or unlocking of each bin 410. In some embodiments, the common latching mechanisms 428, 429 are mounted to a common portion of the bin array assembly 400.

As illustrated, each bin 410 is redundantly locked by a vertical common latching mechanism 428 and a horizontal common latching mechanism 429. As described herein, a bin 410 can be retained or locked in a closed position, when one or both of the vertical common latching mechanism 428 and the horizontal common latching mechanism 429 are engaged with the respective bin body 414.

To unlock a selected bin 410, the corresponding vertical common latching mechanism 428 and the corresponding horizontal common latching mechanism 429 must be disengaged to allow the bin 410 to be unlocked and/or opened by the user. As can be appreciated, other bins 410 that are horizontally aligned with the bin 410 to be opened are still locked by other vertical common latching mechanism 428 while other bins 410 that are vertically aligned with the bin 410 to be opened are still locked by other horizontal common latching mechanisms 429.

With reference to FIG. 12A, for example, the bin body 414a can include a vertical latch hook 426a and a horizontal latch hook 427a both extending from the bin body 414a. The vertical latch hook 426a can engage with a mating latching portion of the vertical common latching mechanism 428 to lock the bin 410a. Similarly, the horizontal latch hook 427a can engage with a mating latching portion of the horizontal common latching mechanism 429 to lock the bin 410a. As can be appreciated, the locking action provided by the common latching mechanisms 428 and 429 is redundant, meaning that bin 410a remains locked if at least one of the common latching mechanisms 428 or 429 is engaged or locked with the bin body 414a.

To release or unlock the bin 410a, the common latching mechanisms 428 and 429 can be disengaged from the bin body 414a to allow the bin body 414a to move (unlocking the bin 410a). In the depicted example, the vertical common latching mechanism 428 can be rotated to disengage from the vertical latch hook 426a. Further, the horizontal common latching mechanism 429 can be rotated to disengage the horizontal latch hook 427a. As can be appreciated, both common latching mechanism 428 and 429 must be disengaged from the vertical latch hook 426a and the horizontal latch hook 427a to unlock the bin 410a. After the bin body 414a is moved back to a closed position, at least one of the common latching mechanisms 428, 429 can be rotated to engage with a respective vertical latch hook 426a and/or the horizontal latch hook 427a.

Advantageously, the use of the common latching mechanisms 428 and 429 allows for independent locking or unlocking of the bins 410 with reduced components.

FIG. 13 is a reverse perspective view of a bin array assembly 200, 310a for use with the medication management system 10 of FIG. 6, in accordance with various aspects of the present disclosure. In the depicted example, bin array assembly may include one or more latches 728. The individual latches 528 of each respective bin 510 are commonly controlled by a central or common latch controller module 725.

The latch controller module 725 can connect to the individual latches 728 via connector ports. The latch controller module 725 can cooperatively control the latching or unlatching of each bin 210 to allow for centralized control of the bins 210 (e.g., only allowing the opening of one bin 210 at a time).

In implementations according to FIG. 13, one or more of the following features may be included: (1) The bin frame 200 contains the storage bin locking mechanism. (2) The bin subassembly frame 200 does not contain a latch. (3) The bin frame includes a latch controller module. The latch controller module has a connector ports to accommodate up to nine latches 126. The latch control module contains electronic hardware to operate up to nine latches independently. (4) Each latch 126 is positioned and mounted to the frame as needed to control its mating bin. (5) Each storage bin has at least one hook that interfaces with a corresponding latch. (6) Each latch is connected to the latch control module.

Additionally or in the alternative, bin assembly 200 may include a passive near field communication (NFC) antennae 528 for each bin 210 within assembly 200. Likewise, each bin may be configured with a passive NFC tag on a side or rear of the bin that, when the bin is loaded within the bin housing 212 of assembly 200, comes into communicable contact with a respective antennae 728. Control module 725 may be operably connected to a bus the within the bin housing via cabling or by wireless means, and the bus may be operably connected to each latch 126 and/or each NFC antennae. While control module 725 is depicted as a separate device from bin assembly 200, it is understood that control module 725 may be part or integral with bin assembly 200, or may be part of or integral with a smart device 130 associated with or linked to assembly 200. It is also understood that depicted diagram for antennae 728 may also be representative of a respective latch 126 or latch actuator.

Each bin may be associated with a unique identifier, which is stored by its respective NFC tag. The identifiers may be mapped to a particular bin specification (e.g., volume, height, etc.) and particular contents currently stored within the bin. For example, server 114 may keep track of the contents of each bin in a database. When a bin 210 is opened, control module 725, receiving the indication from the NFC tag via antennae 728, may send a signal to server 114 indicating that the module was opened, and may send a close signal with the status of the bin changes from open to closed.

Control module 725 may also send the bin location within the assembly together with the identifier of the bin. This way, if a clinician reconfigures the bins, server 114 will update the new configuration in memory. The stored configuration can then be used to provide an alert to the clinician should the clinician move a bin to an undesirable location, or rearrange the bin assembly in a manner not consistent with a healthcare organization's policy or predetermined rules. When an access controller is associated or integrated with control module 725, the bins may be remotely managed using a single interface. If the clinician using an IOT inventory tracker or other smart remote device to open a bin corresponding to a medicine, the server 114 may perform a check to determine which bin holds the requested medicine (e.g., by querying the control module 725), before opening the bin. If the clinician attempts to open the wrong bin, or attempts to place a bin in the wrong assembly location, the control module (via the assembly or smart device 130) may provide an audible and/or visual alert. Control module 725 may also lock a bin from being opened or being inserted into a bin location.

According to some implementations, control module 725 may provide power to the various components of an associated bin assembly 200, including to each bin 210 with the assembly. Power may be daisy chained from control module 725 to one bin location to another, and so on. Control module 725 also includes a central processing system or processor, such as that described with respect to FIG. 5. With reference to FIG. 12, control module 725 may act as a master hub, and operate all bins as slaves in a master/slave configuration. Such configuration may be by way of wired cables or by wireless connection (e.g., BLUETOOTH) between the control module and each bin.

FIG. 14A is a perspective view of a bin 610a for use with the bin array assembly 200 of FIG. 7A in a closed position, in accordance with various aspects of the present disclosure. In the depicted example, the bin 610a includes features that are similar to the features of bin 210a. Therefore similar features are referred to with similar reference numerals. In the depicted example, the bin 610a can include a handle portion 620a to allow a user to open or close the bin body 614a.

FIG. 14B is a perspective view of the bin 610a of FIG. 14A with the bin 610a in a partially open position, in accordance with various aspects of the present disclosure. As illustrated, the bin body 614a can slide or translate relative (e.g. similar to a drawer) to the bin housing 612a for access into the bin volume to allow the user to access medication. The bin body 614a can slide until reaching a travel or slide stop feature.

Optionally, the bin body 614a can be spring loaded, such that the bin body 614a moves outward upon unlocking or latch release, indicating the location of a desired item. In some embodiments, the bin 610a can include a visual indicator, such as an LED to indicate the desired items location.

FIG. 14C is a perspective view of the bin 610 of FIG. 14A with the bin 610a in an open position, in accordance with various aspects of the present disclosure. In the depicted example, the bin body 614a can pivot downwards after extending away from the bin housing 612a. In some embodiments, the rear portion of the bin body 614 includes a pivot pin that allows the bin body 614a to slide outward, and then rotate downward at the end its travel. Advantageously, by rotating or pivoting the bin body 614a downward, access to the items within the bin volume can be improved. In some embodiments, the bin body 614a can be removed from the bin housing 612a to allow for items to be loaded or removed from the bin body 614a or for items within the bin body 614a to be counted.

Optionally, if a bin body 614a is removed from the bin housing 612a and not returned within a predetermined period of time, an alarm may trigger indicating a potential tamper/theft event.

Figure 15A:
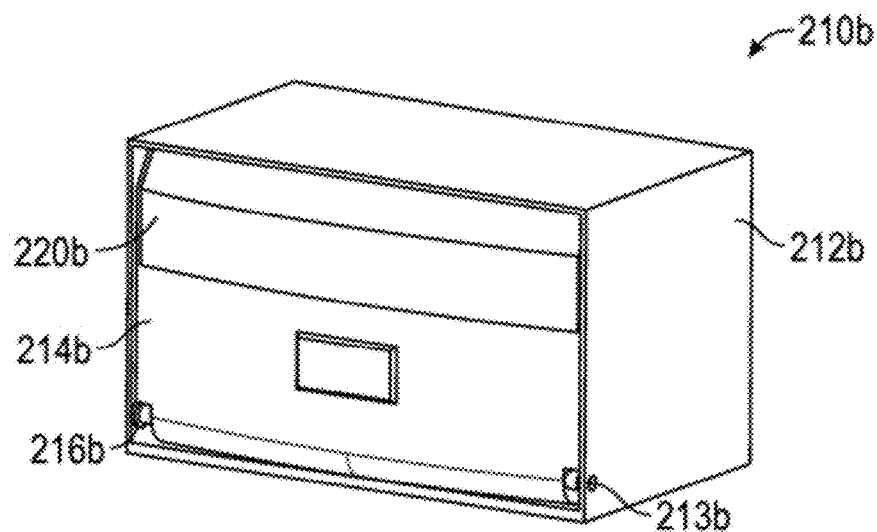
FIG. 15A is a perspective view of a bin for use with the bin array assembly of FIG. 7A in a closed position, in accordance with various aspects of the present disclosure.
Figure 15B:
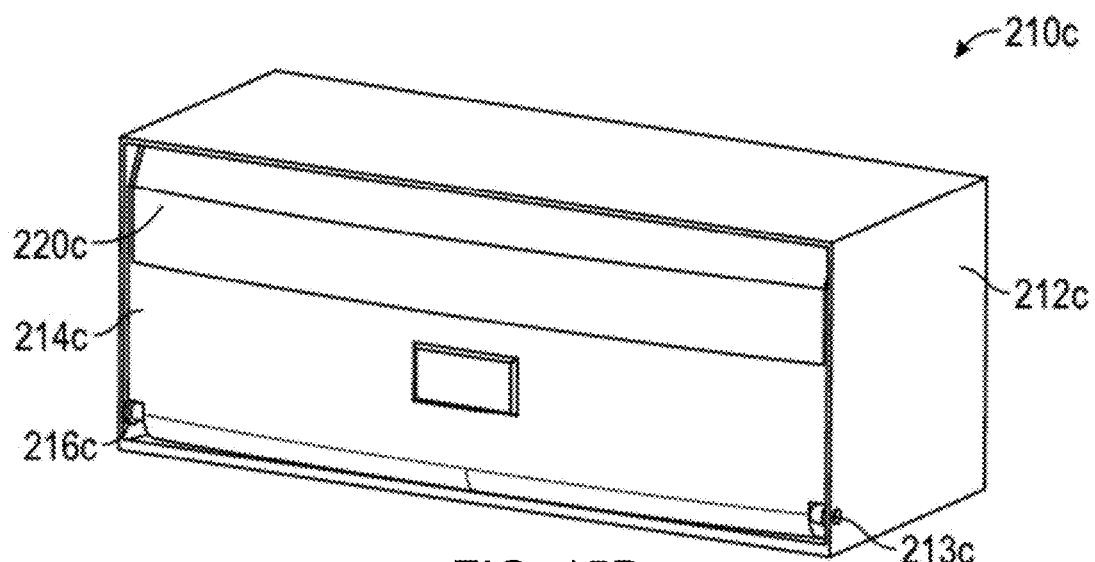
FIG. 15B is a perspective view of a bin for use with the bin array assembly of FIG. 7A in a closed position, in accordance with various aspects of the present disclosure.

FIG. 15A is a perspective view of a bin 210b for use with the bin array assembly 200 of FIG. 7A in a closed position, in accordance with various aspects of the present disclosure. FIG. 15B is a perspective view of a bin 210c for use with the bin array assembly 200 of FIG. 7A in a closed position, in accordance with various aspects of the present disclosure. In the depicted example, the bin 210b and bin 210c each include features that are similar to the features of bin 210a. Therefore similar features are referred to with similar reference numerals. As described herein, the bins 210b and 210c include similar features but may be of varying widths. In some embodiments, the bin 210b and bin 210c can be wider than the width of the bin 210a. The bin 210b can be approximately twice the width of bin 210a. The bin 210c can be approximately three times with width of the bin 210a.

Figure 16A:
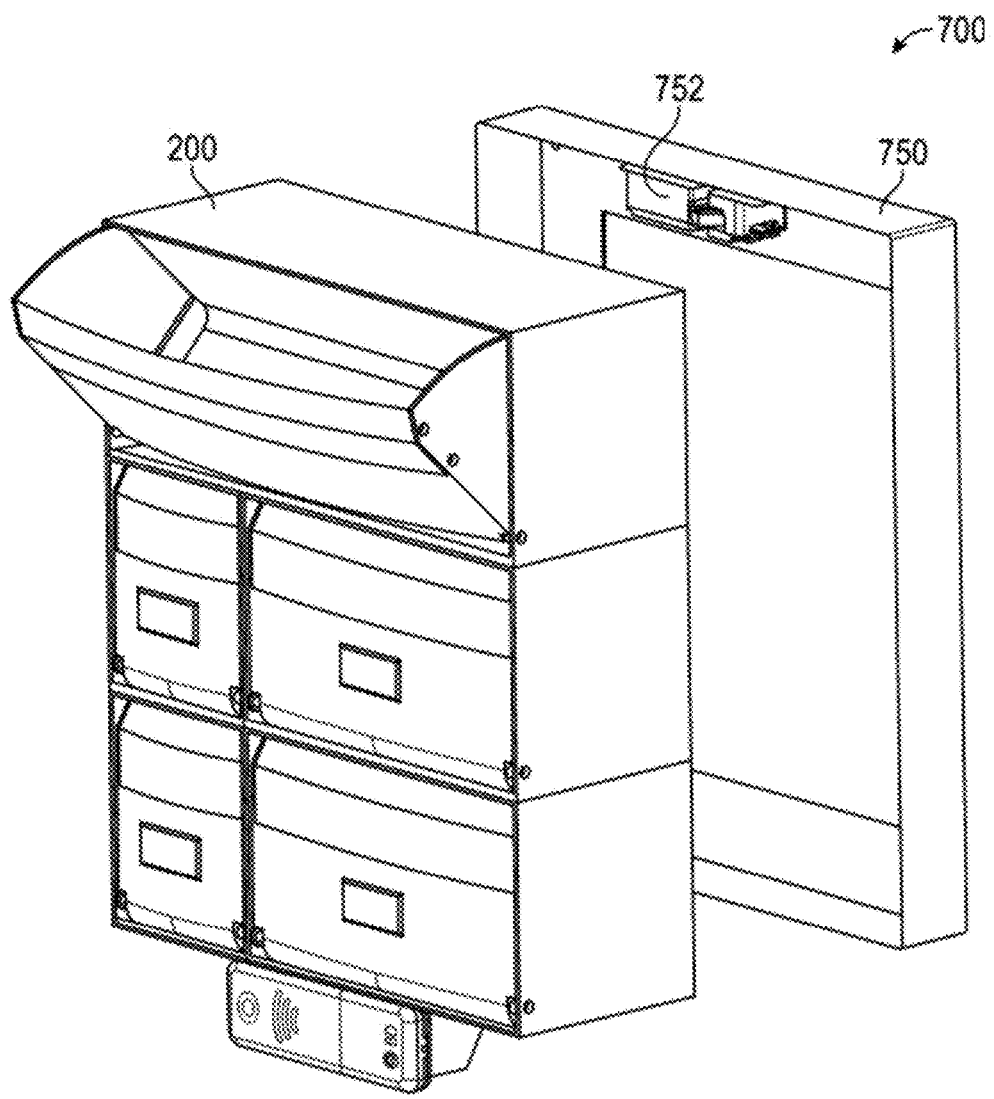
FIG. 16A is a perspective view of a mounting frame for use with the bin array assembly of FIG. 7A, in accordance with various aspects of the present disclosure.

FIG. 16A is a perspective view of a mounting frame 750 for use with the bin array assembly 200 of FIG. 7A, in accordance with various aspects of the present disclosure. In the depicted example, the bin array assembly 200 can be mounted to a wall or other flat surface with a mounting frame 750. The mounting frame 750 can be securely mounted to a wall or other flat surface. The mounting frame 750 can receive the bin array assembly 200 therein. In some embodiments, the bin array assembly 200 can be latched to the mounting frame 750 by a locking or latching mechanism 752. The latching mechanism 752 can be an electromechanical latch. The bin array assembly 200 may be attached and removed from the mounting frame 750 as needed.

Figure 16B:
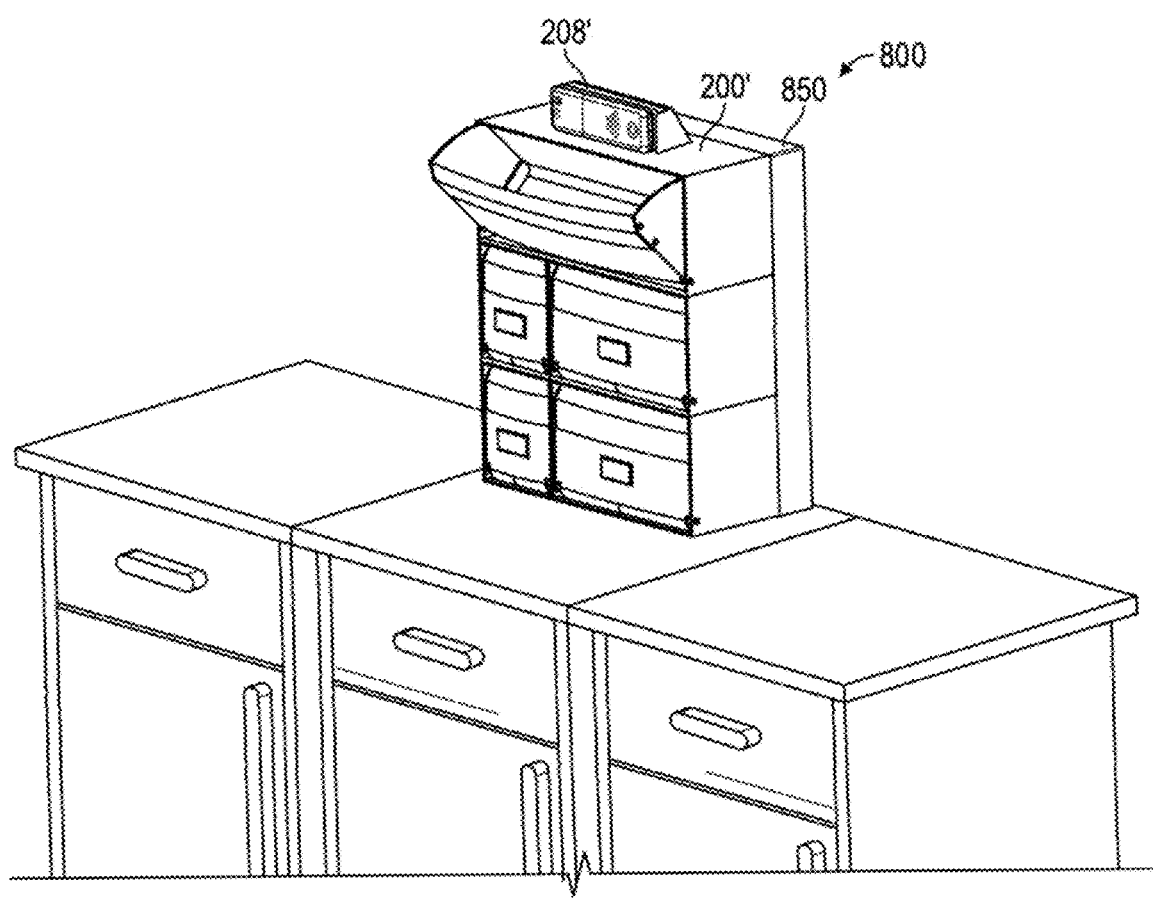
FIG. 16B is a perspective view of a mounting frame for use with the bin array assembly of FIG. 7A, in accordance with various aspects of the present disclosure

FIG. 16B is a perspective view of a mounting frame 850 for use with the bin array assembly of FIG. 7A, in accordance with various aspects of the present disclosure. In the depicted example, a counter top medication system 800 can utilize a bin array assembly 200' that is mounted to a counter top or similar surface with a mounting frame 850. The mounting frame 850 can be securely mounted to a counter top or other fixture. The mounting frame 850 can receive the bin array assembly 200' therein.

As can be appreciated, the smartcard reader 208' can be arranged at the top of the bin array assembly 200' to facilitate countertop mounting.

In healthcare settings, there is a need for space & cost optimized enterprise secured medication storage and dispensing solutions. Some solutions use an automated dispensing cabinet (ADC) to control medications. ADC are expensive and take up a significant space. Existing user space such as drawers, cabinets and carts may be used to store and dispense medications. However, drawbacks include a lack of security, poor traceability of the medications, and a very manual process which utilizes more nurses or care giver resources. The disclosed solution includes a slimline with smart bin array transforms the underutilized or unutilized user wall space into a highly optimized enterprise medication management space.

Systems and methods for highly optimized medication storage and dispensing in healthcare settings are disclosed. The systems and methods may include a wall mounted slimline smart bin array system with configurable wirelessly connected smart bins (e.g., in different sizes), a plurality of user interfaces, a server authorized actuator lock, and may include location tracking, and may enable an enterprise solution for inventory tracking.

The disclosed system may include a processor, memory, input/output device, environmental sensor, tamper detection and wireless interface.

Other features may include one or more of the following: E-ink display, microphone, buzzer and multicolor LED for user interface; identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present the current state of the workflow; drive circuitry for piezo electric buzzer to provide audio feedback to the user; microphone interface circuitry for the user to provide wakeup words and or voice prompts; actuator latch drive circuitry and latch state read back methods; memory interface to store state and statistics of slimline bin status; sensor interface to monitor tamper, environmental condition & content sensing; and crypto and secure element interface to safely store public/ private keys.

The disclosed system architecture may optimize an existing user space with a wall mounted slimline enclosure and configurable smart bins with wireless connectivity. In some implementations, a slimline enclosure and bin may be placed on a countertop.

In some implementations, the disclosed system architecture may include a latch and electronics to drive the latch as part of the bin. In some implementations, both the latch and electronics may be part of slimline enclosure.

In some implementations, the disclosed system architecture may include a bin that tilts open giving user access to medication and in other implementation bin pops open as a drawer.

In some implementations, the disclosed system architecture may automatically determine a plurality of user authorization methods. The user may then select one of the determined authorization methods to unlock the slimline bin.

An authentication method that securely transmits the user identity to the server and gets authorization to unlock the slimline bin is also disclosed. In some implementations, the system may include, and the authentication method may use, contactless smart card and in other implementations it could use barcode, biometric identification, ECG based wearable device or a mobile phone. In some implementations, the authentication method may include remote authentication. For example, if the user loses their badge or smart phone, a super user can provide remote authentication.

In some implementations, the systems and/or methods may utilize a sensor interface to automatically identify the quantity of contents in the slimline bin and tamper detection of slimline bin or enclosure. For example, the method may include monitoring for tamper detection on slimline enclosure attached to wall (e.g., using one or more sensors), and the slimline bin attached to enclosure, in real time using optics or electromagnetic sensing. In some implementations, the system and/or method includes a sensor interface such as load cell, optics with a led & photodiode, acoustics or RF to sense the quantity of content inside the bin.

A method by which an audible sound indicates user actions such as presenting badge to the slimline or when an actuator command is been executed is also disclosed. In some implementations, the system may include, and the method may use, a piezo beeper with different tones to indicate different actions.

According to various implementations, the system may include communication architecture (CA), which may use plurality of PAN protocols such as (802.15.4/BLE) to talk to the remote device. Accordingly, the disclosed system and/or method may use the CA to achieve one or more of the following features: beacon for asset tracking; real time and offline mode support.

In some implementations, the disclosed slimline bin (e.g., using CA) may bypass hospital IT, thereby reducing implementation time (e.g., implementing a drop ship model based on PAN protocol support).

The system and/or method implementing communication architecture (CA) may support an offline mode. When a network connection to the field hub or gateway is lost the disclosed slimline bin(s) may still allow the user to continue with their action, and the system may store and forward the actions when the network is restored.

In some implementations, the slimline bin(s) have the ability to broadcast beacons to a remote host, with the medication information for asset tracking. In some implementations, users can also read the beacons using a mobile device such as a phone or tablet.

In some implementations, the disclosed system and/or methods may include power architecture that utilizes disposable batteries or, in other implementations, the power architecture may implement rechargeable battery or a supercapacitor as an energy source for each bin. In some implementations, the power architecture (PA) may require one high capacity energy source to power the entire slimline bin array. For different implementations of high capacity energy source (PoE, battery, external power supply) and its interface using wired or docking connector see attached slides and docs.

In some implementations, a slimline bin array may be connected to an external power supply, the external power supply may directly power the slimline bin, or may charge the battery on the bin or enclosure. In some implementations, the disclosed system and method may include power architecture that uses wireless power transfer to access the slimline smart bin.

A method for charging the system using a plurality of wireless energy sources is also disclosed. In some implementations, a near field (such as NFC, Qi, Resonant and inductive) or far field (such as WiFi, UHF) wireless power transfer are used as energy source to access the slimline bin.

In some implementations, a multiplexed wireless charging scheme may be used to charge the secure storage solution. In some implementations, only one storage location may be accessed at a given time inside a slimline.

In some implementations, guided lights or mechanical features are used to dock the secured storage space for wireless charging.

A method for conserving power in battery operated devices based on system factors and user preference is disclosed. In some implementations, the method may include placing devices in low power states (ranging from system off state to various levels of sleep state) and waking up the devices periodically (wake up period) to enable radio communications, and checking in with a gateway/hub for updates or to perform transactions.

The low power state and wake up period may be configured by the gateway/hub for devices based on system usage factors and user preferences.

In some implementations, the system may include, and the method may include using, environmental sensors such as occupancy sensors. In some implementations, the system and/or method may use microphone with key word activation, user action by pushing a button or system usage factors such as user presence, office schedule to wake up the device from deep sleep mode.

A method for energy harvesting using plurality of sources to increase slimline smart bin operation life is also disclosed.

In some implementations, electromagnetic induction from lock actuator action or wireless energy from RF sources may be used to harvest energy.

In some implementations, the e-ink of the user interface of the device may display medication name, dosage and expire date. In other implementations, icons such as loading dock or in transit may be displayed to show the current status of associated medication that is been tracked.

In some implementations, the multicolor LED user interface may act as a glanceable status indicator. For example, the LED color, flash pattern and intensity may indicate different status based on user accessing the secure storage location and workflow.

Example 1: During medication loading workflow the led lighting can guide the user to the medication at a glance.

Example 2: If the medication in the slimline bin expired the LED can flash red.

Example 3: During medication audit the system may guide by lighting the LED's so the user can identify the med easily.

Example 4: If the battery level lower than threshold led can flash.

Figure 17A:
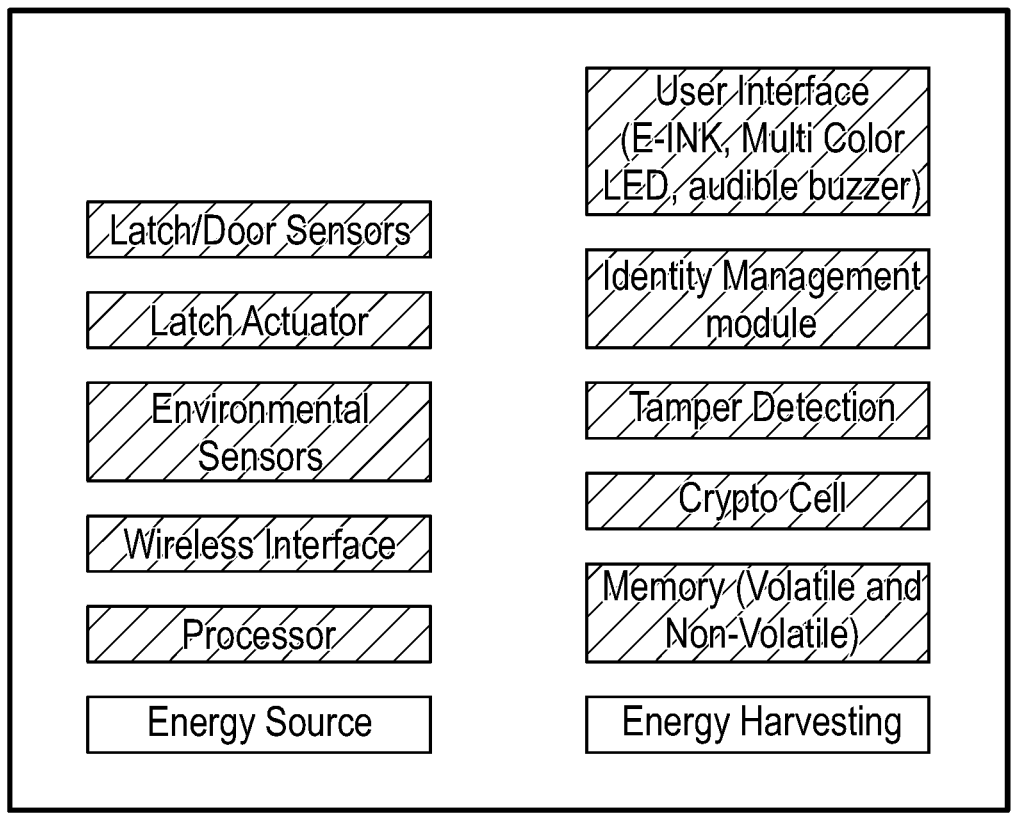
FIGS. 17A, 17B, and 17C depict various implementations of a smart system 100, including a interactive storage device 130 and/or a smart lock, according to some aspects of the subject technology.
Figure 17B:
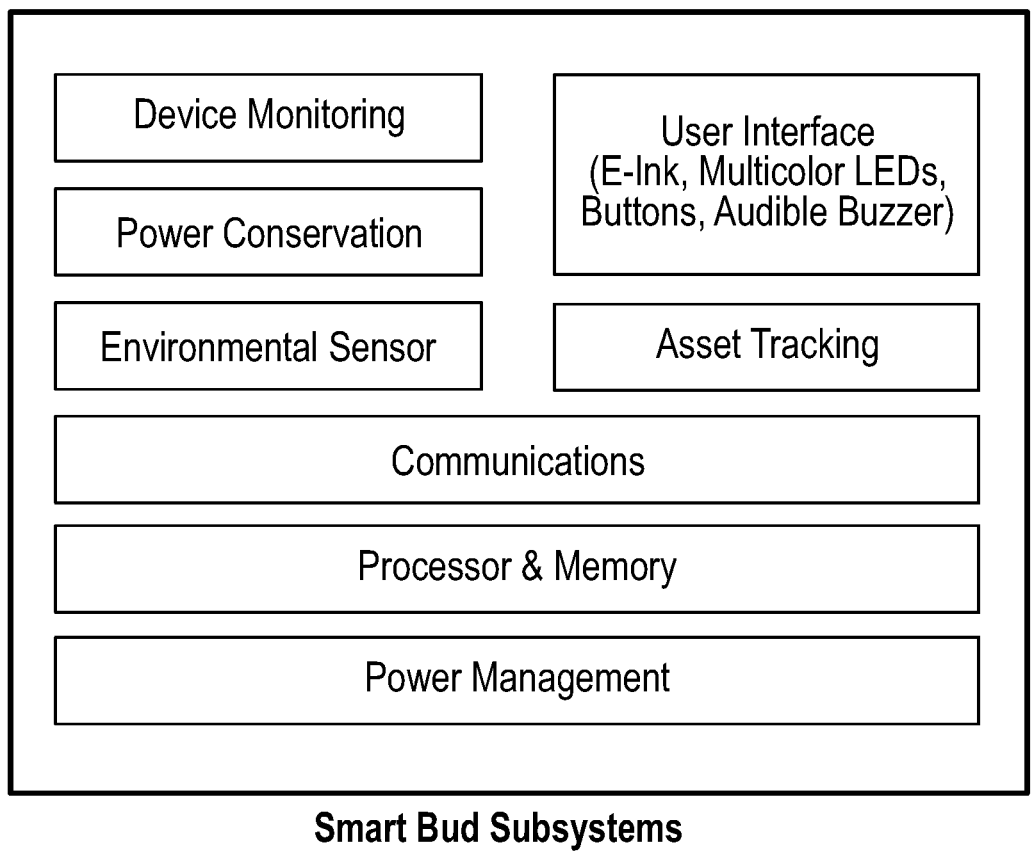
Figure 17C:
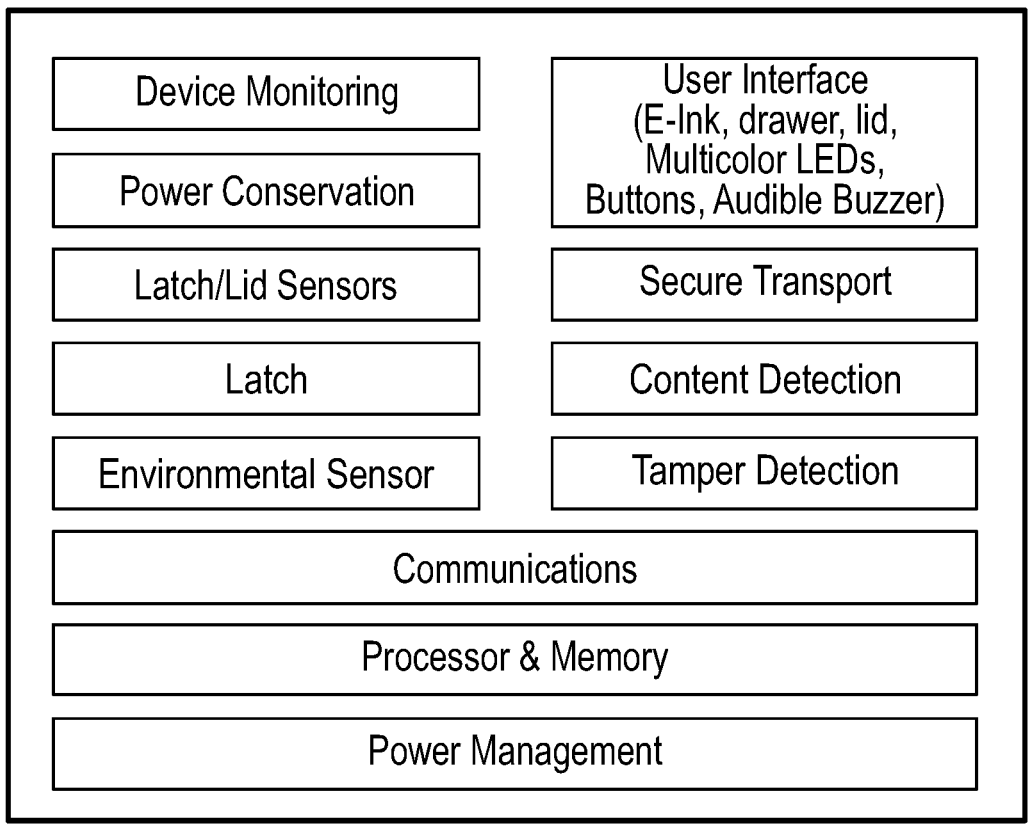

FIGS. 17A, 17B, and 17C depict various implementations of a smart system 100, including a interactive storage device 130 and/or a smart lock, according to some aspects of the subject technology. In these examples, the system includes plurality of user interfaces, a server authorized actuator lock, lock and door sensors, identity authentication module, and other components that enable an enterprise solution for securing medication and guided loading of medication.

The E-ink user interface of the device may, in some implementations, display status of the smart lock system using icons such as battery level, network connectivity, status of the latch and door.

The E-ink user interface of the device may, in some implementations, in some implementations may display alerts such as expired medication, medication below par, tamper detection and etc.

The E-ink user interface of the device may, in some implementations, display information collected from the environmental sensor. Examples of such information collected include temperature of medication, monitor tamper evidence sensor signal, humidity, shock, and vibration over time.

The E-ink user interface of the device may, in some implementations, dynamically display information based on configuration associated with the user as to the contents of the display.

In some implementations, the multicolor LED user interface may act as a glanceable status indicator. The LED color, flash pattern, or intensity may be adjusted by the device (or in response to a control signal from a central control server) to indicate different status. The status may be based on user accessing the secure storage location, workflow, inventory level, or other detectable characteristic of the device or contents thereof.

Example 1: During medication loading workflow the LED lighting can guide the user to the medication at a glance.

Example 2: If the medications being secured by the smart lock has expired the LED can flash red.

Example 3: During medication audit the system may guide by lighting the LED's so the user can identify the med easily.

Example 4: If the battery level lower than threshold LED can flash in low intensity.

Example 5: LED color and flash pattern to indicate authorized user unlocked the latch.

Also provided is a computer implemented method by which a handheld device can scan the LED color, intensity and flash pattern and identify its status during manufacturing or in field. The computer-implemented method may be performed under control of one or more processing devices (e.g., CPUs or computer systems and/or devices).

The method may be implemented, in whole or in part, using an inspection equipment, a mobile application, and an optical reading device to read the multicolor visual indicator and analyze the reading to determine the failure modes and conditions on smart lock. Reading the indicator may include capturing an image of the LED. Reading the indicator may include capturing a series of images of the LED. The series may be captured for a period of time or number of frames identified using a configuration value. The series may be captured based on information encoded by the LEDs. For example, a preamble pattern or color may identify the start or end of a status sequence. When the device reads this pattern for a second time, the device may terminate reading and being the analysis of the captured image(s).

The authentication system may automatically determine a plurality of user authorization methods. The user may select one of the determined authorization methods to unlock the smart lock.

Features are also described for securely transmitting a user identity to a server and transmitting an authorization to unlock the smart lock. The authentication may, in some implementations, include reading data from a contactless smart card. In other implementations, it may use barcode, biometric identification, ECG based wearable device, a mobile phone, or a combination of the authorizations to request unlocking of a smart lock.

The authentication may include remote authentication. For example, users can enter credentials at tablet or PC or use a standalone authentication module to gain access to the smart lock or if the user loses their badge or smart phone a super user can provide remote authentication.

The sensor interface in an environment associated with a smart lock may monitor NIST traceable environmental sensor or tamper detection data in real time (e.g., within a threshold period of time from actual occurrence of the sensed environment condition or tamper event).

The systems or methods may generate an audible sound acknowledging user actions such as presenting badge to the smart lock or when an actuator command is been executed.

For example, in some implementation, a piezo beeper may be configured to emit different tones whereby each tone indicates a different action.

The communication architecture (CA) for the systems and methods, may include one or more of a plurality of personal area network (PAN) protocols such as (802.15.4/BLE) to communicate with the remote device.

The CA may be configured to detect beacon signals for asset tracking, provide environmental sensor and tamper detection monitoring, generate real time and offline mode support, or identify tote contents and track inventory. Because some health care supplies are temperature sensitive, if an environmental sensor determines that the temperature or humidity to which an item was exposed is outside an expected range, the system may dynamically adjust to alert or prevent dispensing of exposed items. Similarly, a sensitive item may have been tampered with. The system may direct storage or prevent distribution of such items until the integrity is confirmed. The confirmation may include an authorized user verifying the item before being eligible for dispensing and use in the healthcare facility.

According to various implementations, the smart lock CA can bypass set up and attachment to hospital IT resources. This can reduce implementation time and make it a drop ship model because of PAN protocol support.

A smart lock device may be configured to act as a companion device for devices placed inside the enclosure to bridge communications. Connected devices placed inside enclosures, such as refrigerators and metal cabinets, may have their radio signals attenuated and have difficulty communicating to hubs located further away. In these cases, another device such as the Smart lock is used as companion device to enable reliable communication to the hub/gateway. Smart lock when acting as a companion device can fill two roles: (i) a slave role communicating to the hub; (ii) a master role communicating to the devices behind the enclosure.

Figure 18:
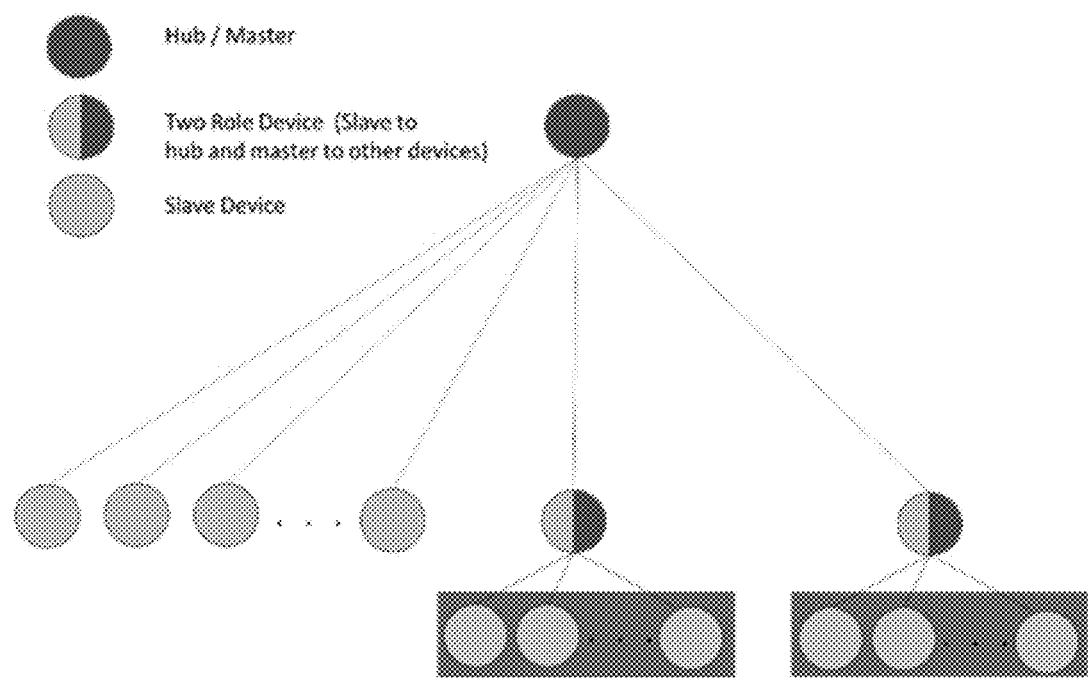
FIG. 18 depicts the disclosed interactive storage devices arranged in a multi-level network hierarchy, according to various aspects of the subject technology.

FIG. 18 depicts the disclosed interactive storage devices 130 arranged in a multi-level network hierarchy, according to various aspects of the subject technology. In the depicted example, interactive storage devices 130 may be configured to communicate back to a hub either directly or through another device.

The power architecture of the smart lock device and/or system may include disposable batteries and in other implementations it may include rechargeable batteries. To improve efficiency of the devices by conserving power in battery operated devices, the power management module may operate based on system factors and user preference. The power management module may be implemented within a specific device to conserve resources of the device in which it is implemented. The power management module may be a central device configured to manage power for a group of devices in data communication therewith.

Devices may be placed in various low power states and may be configured to wake up periodically. The power management module may transmit a control signal to the devices in various low power states to wake up them up periodically (wake up period) and enable radio communications and check in with a gateway/hub for updates or to perform transactions.

The power saving states may be used to adjust device responsiveness versus power savings. The low power states and wake up period may be dynamically configured by the gateway/hub for devices based on system usage factors and user preferences.

Power states may be adjusted based on user presence. For example, if a sensor detects that users are present, the devices may be controlled to operate in more responsive states in anticipation of the system being used. If a sensor detects that users are not present or have left an area including one or more devices, the power management module may adjust devices within the area to operate in less responsive states, to maximize power savings.

User presence can detected in different ways including users logging into the system or by occupancy sensors such as motion, radar, and proximity sensors. Occupancy sensors are envisaged to be powered devices located in the health care service area (e.g., examination room, procedure room) and interface to the gateway/hub.

In some instances, users may provide an office schedule into the system and power states are adjusted based on this schedule (e.g., when an appointment is included for a time period on the schedule). The office schedule may indicate times when clinicians are working in the health care facility. Similar power adjustments may be controlled based on shifts when clinicians are active as indicated by the schedule.

Some instances may include microphones coupled with a speech detection system. The speech detection system may identify a key word to activate one or more device (e.g., adjust power state to an active/ready mode). In some implementations, a user action such as pushing a button or system usage factors such as user presence, may be used to wake up the device from a sleep mode.

In some instances power states may be adjusted by ML algorithms running on the hub/gateway and/or cloud. For example, historic patterns of usage may be analyzed to develop a model of power state activity that may be used to control one or more devices.

Features may also be included for harvesting energy using plurality of sources to increase smart lock operation life. In some instances uses piezo transducers interfaced to buttons or electromagnetic induction from lock actuator or drawer/door open and close action or wireless energy from RF sources to harvest energy.

The latch and door sensors included the system may include sensors to read the status of both the latch and door/drawer at all times. This capability enables workflow execution and also is used to detect tamper detection.

FIGS. 19A, 19B, and 19C depict a remote smart lock reader module configured to unlock a securable container, according to various aspects of the subject technology. FIG. 19C depicts the remote smart lock reader module added to cabinet doors and/or cabinet drawers for controlled security.

In the depicted example, a smart lock reader module may be implemented as a mobile device that contains a PCBA, NFC reader, Multi Colored LEDs, Common Batteries, mounting features, e-ink display, biometric reader, audio buzzer, LED light pipe, barcode, snap-on cover in order to access the batteries.

Figure 20A:
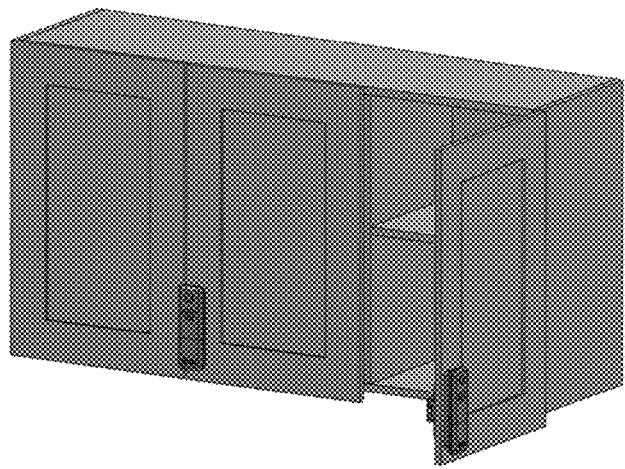
FIGS. 20A, 20B, and 20C depict an electromechanical latch mounted to an interior surface of the door or drawer using a bracket 1602, according to various aspects of the subject technology.
Figure 20B:
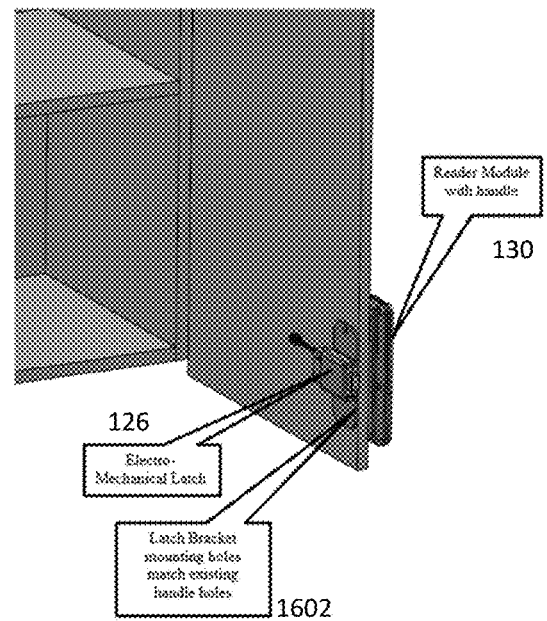
Figure 20C:
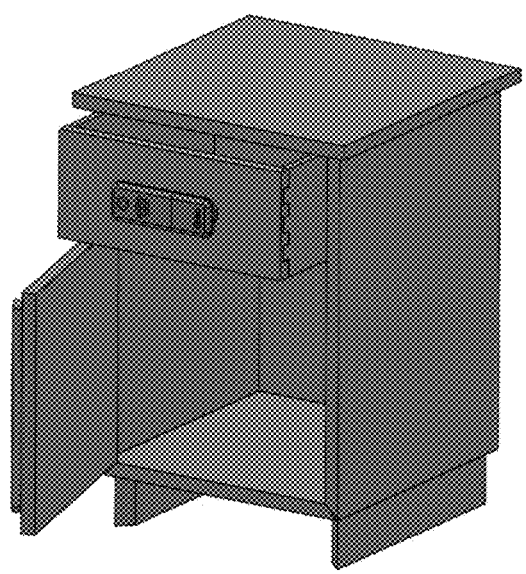

FIGS. 20A, 20B, and 20C depict an electromechanical latch 126 mounted to an interior surface of the door or drawer using a bracket 1602, according to various aspects of the subject technology. The electromechanical latch is operably connected to the smart lock reader module 208', which may electronically control the latch. The shape of the housing allows the user to grip the smart lock and use it has a door or drawer handle.

The screws that mount the bracket pass through the door or drawer and thread into the outer housing. When the batteries expire, the latch remains in the locked position and the batteries are replaced to continue operation. The LEDs indicate location. Audio indicator can alert an open door or drawer. A sensor is used to determine if the door(s) are in the closed or open position. A sensor is used to determine if the latch is locked or unlocked.

The smart lock can communicate wirelessly to other devices. The smart lock units can have overlapping features, interlocks and to prevent diversion and indicate tamper evidence.

Figures 21A, 21B:
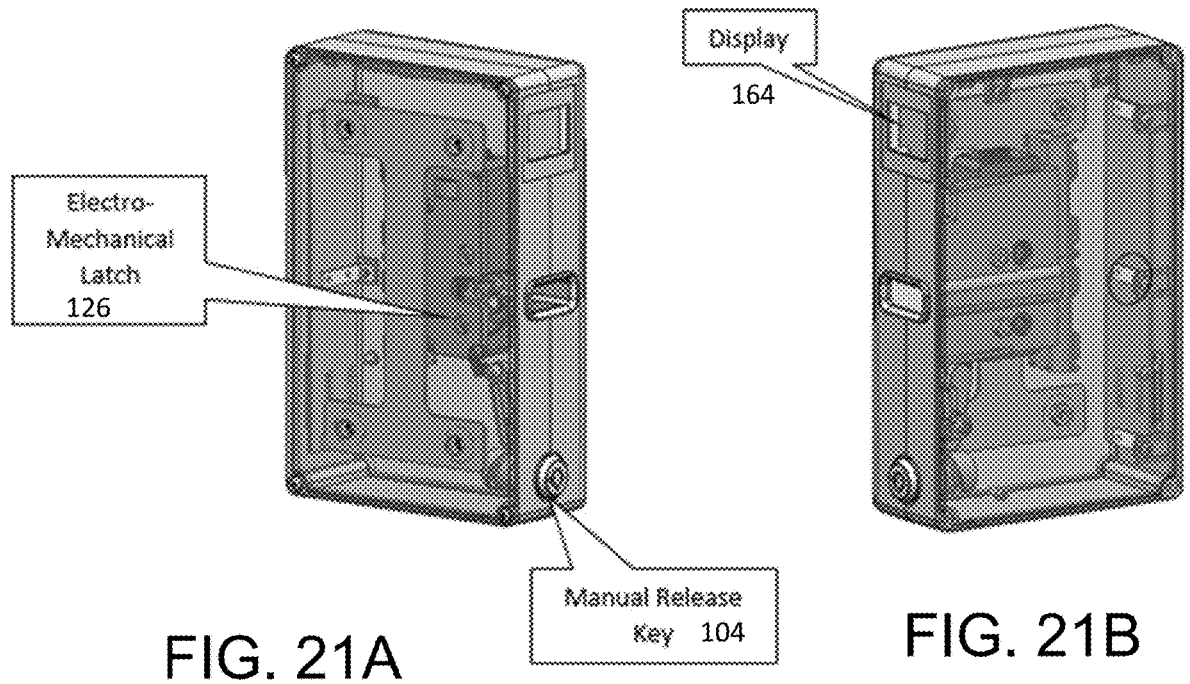
FIGS. 21A and 21B depict a cut-away view of an example IOT (Internet-of-things) smartlock reader module (SRM), according to various aspects of the subject technology.

FIGS. 21A and 21B depict a cut-away view of an example IOT (Internet-of-things) smartlock reader module (SRM), according to various aspects of the subject technology. According to some implementations, the disclosed IOT SRM includes a device that may be attached to a refrigerator. In this regard, the IOT SRM may incorporate an electromechanical lock 126 for secured access to the refrigerator. The IOT SRM may include an (e.g. e-ink) display 164, LED indicator, Temperature readout, and common batteries for ease of replacement. The IOT SRM may be configured to communicate wirelessly with other devices. The IOT SRM may include a manual release key 104 to release lock 126 by mechanical means (e.g., when power has been removed from the lock).

Figure 22:
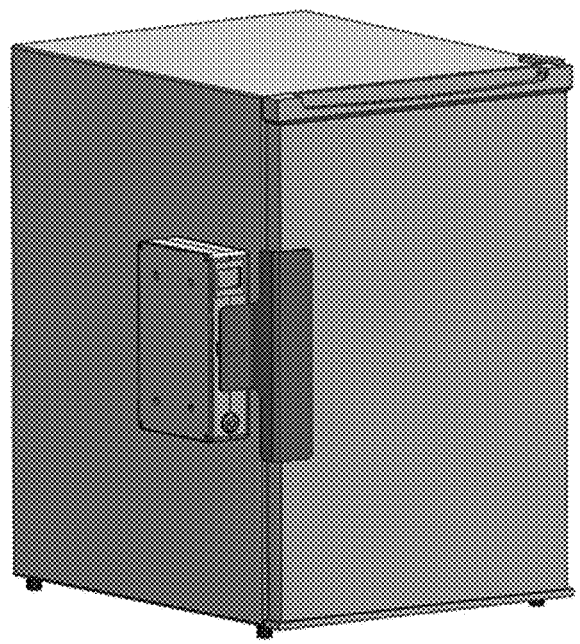
FIG. 22 depicts an example IOT SRM mounted on the exterior surface of a refrigerator, according to various aspects of the subject technology.

FIG. 22 depicts an example IOT SRM mounted on the exterior surface of a refrigerator, according to various aspects of the subject technology. The refrigerator may include an off-the-shelf "dorm" style refrigerator for controlled security. The IOT SRM may include a repeater to aid in the communication of IOT devices within the refrigerator. The IOT SRM may include overlapping features, interlocks and materials to indicate tamper evidence. The IOT SRM may include a key lock for manual release.

Modular Dispensing Bin

Another aspect of the disclosure relates to a smart bin or tote system, device, and/or corresponding methods which provide secure access and transport of items including medications and supplies (the "smart bin"). The disclosed smart bin may be configured for controlled, non-controlled, refrigerated and non-refrigerated items in both acute and non-acute health care settings. The disclosed smart bin may be configurable to allow the different authentication requirements of both regulatory bodies and hospitals.

Figure 23:
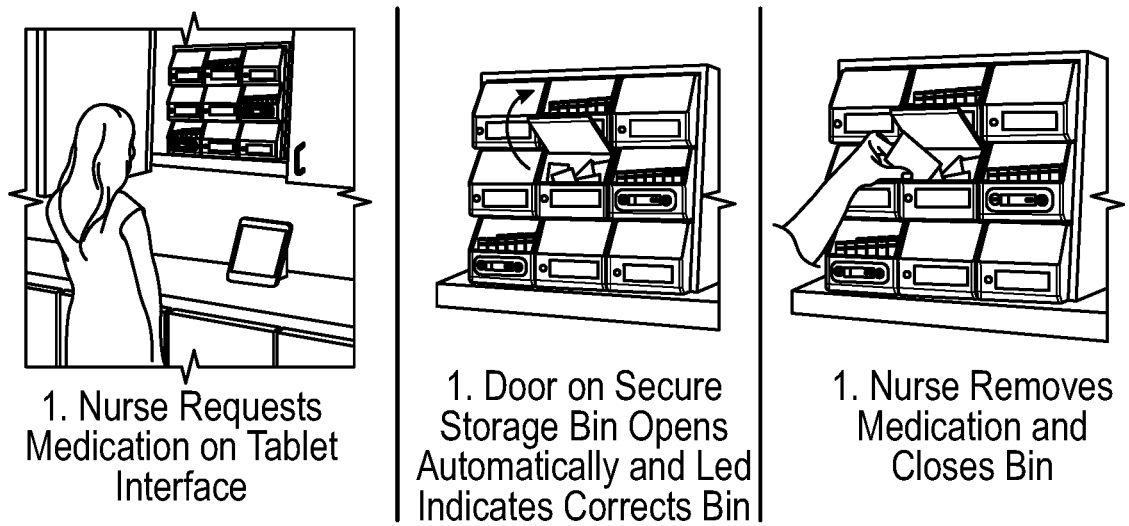
FIG. 23 depicts an example smart bin system for dispensing items, according to various aspects of the subject technology.

FIG. 23 depicts an example smart bin system for dispensing items, according to various aspects of the subject technology. In various implementations, the smart bin system and/or device(s) may be configured as a singular, stackable and secure modular bin, for item storage and retrieval. A smart bin may communicate wirelessly with other devices, and may be configured to record user access.

The smart bin system and/or device(s) may be configured to withstand a refrigerated environment, and may include material and components that may be used at cold temperatures. The smart bin system and/or device(s) may be placed in a refrigerator and may support optional sensors for temperature and humidity. The smart bin system and/or device(s) may be configured with overlapping features and interlocks to prevent diversion. The smart bin system and/or device(s) may be designed to indicate an user's attempt to divert. The smart bin system and/or device(s) may be formed of or include material that may be deformed showing taper evidence. Additionally or in the alternative, the smart bin system and/or device(s) may include a hook configured to break and leave a piece in the latch making it unusable thereby indicating a break-in.

The disclosed smart bin may provided in multiple sizes to accommodate different items and is stackable to optimize storage locations. The disclosed smart bin may be a wireless connected device connected to a gateway and connects to an enterprise level application. According to various implementations, users may authenticate using remote authentication methods (such as a tablet or standalone authentication modules) and a secure and traceable access is provided to the smart bin. The disclosed smart bin may include one or more user interfaces that include multi-color LEDs, E-Ink display, buttons and audible buzzers. In some implementations, smart bin may include a machine learning (ML) inference and data analytics to optimize power consumption on smart bin based on its awareness of usage context. In some implementations, the disclosed system, device, and/or method includes a handheld device or mobile application that can scan multicolor led and identify system status during manufacturing or field.

The disclosed smart bin and related systems and method may include implementation of an enterprise level solution that provides traceability and inventory tracking of item in a multitude of use cases.

Secured storage for controlled medications involve off the shelf keyed or combination lock bins that are placed on countertops or inside cabinets and drawers. Users may use the same key or combination numbers to access medication. However, these solutions are not traceable as to who accessed the medication. Additionally, tracking of inventory in non-acute care settings is performed manually and is not accurate. The smart bin described herein provide secure traceable access to these medications. The smart bin may also provide a display screen to indicate quantity and buttons for users to increment or decrement quantities, and may be connected to an enterprise level medication management software which enables end to end inventory management.

According to some implementations, the disclosed smart bin is configured to be placed inside refrigerators to provide secure access and inventory management to refrigerated medications. In some implementations, the smart bin may be configured as a mobile device which may be used for secure transport of medication. A secure bin may be used on its own or placed inside the previously described smart tote for secure transport. The smart bin may be configured to beacon its unique ID over the wireless interface and is used for location tracking of the bins.

In some implementations, the smart bin is a stationary device located in medication rooms, at a bedside of the patient, or at other care locations. In some implementations, the disclosed smart bin is located inside refrigerators. The disclosed smart bin may be configured to be hardened to withstand refrigerated environments. In some implementations, the disclosed smart bin is a mobile device used for secure transport of items. The disclosed smart bin may include a plurality of user interfaces which enables an enterprise solution for securing one or more items and guide the loading of the item(s).

With further reference to FIGS. 1 and 17A, 17B, and 17C, the disclosed system and/or device may include an E-ink user interface. In some implementations, the user interface may display status of the disclosed smart bin using icons such as battery level, network connectivity, and/or status of the latch and door. In some implementations, the user interface may display alerts such as expired medication, below par, tamper detection etc. In some implementations, the user interface may display information collected from an environmental sensor. For example, the user interface may display information such as temperature of medication, monitor tamper evidence sensor signal, humidity, shock and vibration over time. In some implementations, the user interface may display item name and item quantity. In some implementations, the contents of the display is configurable by the user.

In some implementations, the user interface may include one or more buttons that are used to decrement and increment quantity of the item. In some implementations, the user interface may function as a glanceable status indicator. For example, LED color, flash pattern and intensity may indicate different status based on user accessing the secure storage location and workflow.

Example 1: During medication loading workflow the led lighting may guide the user to the medication at a glance.

Example 2: If the medications being secured by the Smart bin has expired the LED can flash red.

Example 3: During medication audit the system may guide by lighting the LED's so the user can identify the med easily.

Example 4: If the battery level lower than threshold led can flash in low intensity Example 5: Led color and flash pattern to indicate authorized user unlocked the latch.

In some implementations, the disclosed smart bin system may include or embody a handheld device that may scan the led color, intensity and flash pattern, and identify its status during manufacturing or in field. In some implementations, the Smart bin system may include inspection equipment or a mobile application, and/or an optical reading device to read the multicolor visual indicator and to obtain the failure modes and conditions on smart bin.

Access to disclosed smart bin may be authenticated via remote authentication. For example, users can enter credentials at tablet or PC or use a standalone authentication module to gain access to the disclosed smart bin. If a user loses their badge or smart phone the super user may provide remote authentication.

In some implementations, the disclosed smart bin may be configured to produce an audible sound that indicates user actions such as when an actuator command is been executed. In some implementations, the disclosed smart bin includes a piezo beeper is used with different tones to indicate different actions.

In some implementations, the disclosed smart bin may include an environmental sensor interface system. In some implementations the environmental sensor interface system may be capable of monitoring NIST traceable temperature sensors used for cold storage of vaccines. In some implementations the environmental sensor interface system may be capable of monitoring plurality of sensors including: temperature, humidity, vibration, orientation and acceleration of the smart bin.

In some implementations, the disclosed smart bin may include a tamper detection system. The tamper detection system may be configured to detect tamper via the foregoing environmental sensors and/or additional sensors (e.g. optical and electromagnetic sensors) located on the latch, drawer and lid which detect unauthorized access to contents of smart bin.

In some implementations, the disclosed smart bin may include a content detection subsystem. The content detection subsystem may utilize the sensor interface to automatically identify the quantity of contents inside smart bin. In some implementations, the disclosed smart bin may support a sensor interface such as load cell, optics with a led & photodiode, acoustics or RF to sense the quantity of content inside the bin. In some implementations, the disclosed smart bin may support a coarse level of identification used for auto-detection PAR levels.

In some implementations, the disclosed smart bin may include a power subsystem. The power subsystem may be configured to support a distributed architecture where each bin has its own wireless communication interface and power source. In some implementations, the power subsystem may include a central architecture where multiple bins are wired to a single controller. The controller may provide wireless communications and power source for multiple bins. Accordingly, the number of wireless communication interfaces, electronics and power sources may be reduced, which may be desirable in cases where many bins are co-located (i.e. multiple bins stacked inside one cabinet).

The disclosed system, device, and/or method may include a communication architecture (CA). In some implementations, the CA may be configured with a plurality of PAN protocols such as (802.15.4/BLE) to talk to a remote device. A method that utilizes the CA may include one or more of the following features: beacon for asset tracking; real time and offline mode support; environmental sensor and tamper detection monitoring; content identification and inventory tracking. In some implementations, the smart bin (e.g., using CA) may bypass hospital IT, thereby reducing implementation time (e.g., implementing a drop ship model based on PAN protocol support).

According to various implementations, the disclosed smart bin may be configured to act as a companion device for devices placed inside the enclosure to bridge communications. Connected devices placed inside enclosures, such as refrigerators and metal cabinets, may have their radio signals attenuated and have difficulty communicating to hubs located further away. Accordingly, the smart bin may be used as companion device to enable reliable communication to a hub/gateway. The smart bin when acting as a companion device may play two roles: (1) A slave role communicating to the hub; and (2) A master role communicating to the devices behind the enclosure. As discussed previously with regard to FIG. 12, the foregoing creates a multi-level network hierarchy in the network of devices all communicating back to the hub either directly or through another device.

In some implementations, the disclosed smart bin system and/or device may include a power architecture (PA). In some implementations, the PA may be configured to use disposable batteries or, in some implementations, rechargeable batteries.

In some implementations, the disclosed smart bin system, device, and/or corresponding method may be configured for energy harvesting using a plurality of sources to increase smart bin operation life. In some implementations, the smart bin may be configured with piezo transducers interfaced to buttons or electromagnetic induction from lock actuator or drawer/door open and close action or wireless energy from RF sources to harvest energy. In some implementations, the disclosed smart bin system and/or device may include a power management subsystem that conserves power in battery operated devices based on system factors and user preference. In this regard, a method for conserving power may include placing devices in various low power states to wake up periodically (wake up period) and enable radio communications and check in with a gateway/hub for updates or to perform transactions. Power saving states may adjust device responsiveness vs power savings. The low power states and wake up period may be configured by the gateway/hub for devices based on system usage factors and user preferences.

In some implementations, power states may be adjusted based on user presence, if users are present the devices are placed in more responsive states in anticipation of the system being used. If users are not present the devices may be put in less responsive states, to maximize power savings In some implementations, the smart bin may detect user presence. For example, smart bin may detect users logging into the system, by occupancy sensors such as motion, radar, and proximity sensors. Occupancy sensors may be configured to be powered devices located in the med room area and interface to the gateway/hub.

In some implementations, the disclosed system may receive user input of office schedule into, and power states may be adjusted based on this schedule. In some implementations, the disclosed system may use microphones with key word activation to wake up the device from deep sleep mode. In some implementations, power states may be adjusted by ML algorithms running on the hub/gateway and/or cloud.

In some implementations, the disclosed smart bin system and/or device may include a monitoring subsystem. The monitoring subsystem may include or interface with sensors which monitor health of the device including the environmental sensors, and/or additional sensors monitoring the operation of the device such as currents on motors, voltages, temperatures of critical components, etc.

In some implementations, the monitoring subsystem may be configured to transmit collected data to the hub/gateway/cloud for analytics. In some implementations, the disclosed smart bin system and/or device may include a secure transport subsystem. The secure transport subsystem may be configured to facilitate use of the smart bin for secure transport of item.

In some implementations, the smart bin may be used as a standalone transport or may be placed inside a tote (e.g., the disclosed smart tote). In some implementations, the smart bin may be configured to play a beacon role, advertising its unique ID, so it may be identified and located for asset tracking by hubs or mobile devices. Unique ID and configuration information, including contents of the smart bin, may be stored locally on the device in a non-volatile memory. This information may also be made available to an online database (e.g., for retrieval view an online network).

In some implementations, the secure transport smart bin may be configured to be tracked by hubs which are in areas of interest. As the device moves. hubs located in the area may be able to read the beacon and identify the device. For example, hubs may be placed in areas of interest such as shipping and receiving, staging areas, hallways etc. In some implementations, the beacons may be read by mobile devices. In some implementations, the secure transport smart bin may be queried directly by hubs or mobile devices for additional information such as contents of smart bin, destination, battery level, environmental sensors etc. Alternatively, the mobile device and/or hubs may be network connected and may be configured to retrieve information about the smart bin from a network database using the beacons unique ID.

In some implementations, the secure transport smart bin may be configure to implement wireless signal characteristics, which may be used to locate and guide a user to the smart bin modules. This may be desirable where a specific device needs to be located and a user may be guided to the unit they are looking for.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A bin assembly, comprising: a bin housing adapted to receive bins of varying sizes, the bin housing including a vertical mounting structure; a bin body comprising a latching hook and the bin body defining a bin volume, wherein the bin body is movable relative to the bin housing to permit access to the bin volume in an open position and to prevent access to the bin volume in a closed position; a latching mechanism coupled to the bin housing, the latching mechanism comprising a latching member, wherein the latching member engages the latching hook in a locked position to retain the bin body in the closed position and the latching member is spaced apart from the latching hook in a released position; and a controller configured to: receive a wireless control signal; and control movement of the latching member based at least in part on the wireless control signal.

Clause 2. The bin assembly of Clause 1, further comprising a battery operatively coupled to at least one of the latching member and the controller.

Clause 3. The bin assembly of Clause 1, wherein the bin body comprises a window.

Clause 4. The bin assembly of Clause 1, wherein the bin body pivots relative to the bin housing.

Clause 5. The bin assembly of Clause 4, further comprising a biasing member to urge the bin body toward the open position or the closed position.

Clause 6. The bin assembly of Clause 4, wherein the bin body comprises a pivot pin extending into the bin housing.

Clause 7. The bin assembly of Clause 6, wherein the pivot pin extends from a front portion of the bin body.

Clause 8. The bin assembly of Clause 6, wherein the pivot pin extends from a rear portion of the bin body.

Clause 9. The bin assembly of Clause 1, wherein the bin body comprises a handle.

Clause 10. A bin array assembly, comprising: a plurality of bin assemblies, wherein each bin assembly of the plurality of bin assemblies comprises: a bin housing adapted to receive bins of varying sizes, the bin housing including a vertical mounting structure; and a bin body comprising a latching hook and the bin body defining a bin volume, wherein the bin body is movable relative to the bin housing to permit access to the bin volume in an open position and to prevent access to the bin volume in a closed position, wherein each of the bin assemblies of the plurality of bin assemblies is disposed horizontally adjacent or vertically adjacent to a neighboring bin assembly of the plurality of bin assemblies; a latching mechanism configured to engage the latching hook of a respective bin assembly of the plurality of bin assemblies in a locked position to retain the bin body of the respective bin assembly of the plurality of bin assemblies in the closed position and to disengage the latching hook of the respective bin assembly of the plurality of bin assemblies in a released position; and a controller configured to: receive a wireless control signal; and control movement of the latching member based at least in part on the wireless control signal.

Clause 11. The bin array assembly of Clause 10, wherein the latching mechanism is configured to engage or disengage the respective latching hooks of a plurality of horizontally adjacent bin assemblies of the plurality of bin assemblies.

Clause 12. The bin array assembly of Clause 10, wherein the latching mechanism is configured to engage or disengage the respective latching hooks of a plurality of vertically adjacent bin assemblies of the plurality of bin assemblies.

Clause 13. The bin array assembly of Clause 10, wherein the latching mechanism is configured to engage or disengage the respective latching hooks of the plurality of bin assemblies.

Clause 14. The bin array assembly of Clause 10, further comprising a battery operatively coupled to at least one of the latching mechanism and the controller.

Clause 15. The bin array of Clause 10, wherein the plurality of bin assemblies includes bin assemblies of different sizes.

Clause 16. The bin array of Clause 10, further comprising an authentication device operatively coupled to the latching mechanism, wherein the authentication device permits the latching mechanism to move to the released position.

Clause 17. The bin array of Clause 10, further comprising a status indicator operatively coupled to the controller.

Clause 18. The bin array of Clause 10, further comprising a mounting mechanism to releasably secure the plurality of bins to a fixed surface.

Clause 19. A method comprising: providing a bin assembly comprising a bin housing and a bin body movable relative to the bin housing, wherein the bin housing is adapted to receive bins of varying sizes; receiving a wireless control signal; latching the bin body to the bin housing in a locked position to retain the bin body in a closed position via a latching mechanism based at least in part on the wireless control signal; unlatching the bin body from the bin housing in a released position via the latching mechanism based at least in part on the wireless control signal; moving the bin body relative to the bin housing to an open position; and providing access to a bin volume defined within the bin body.

Clause 20. The method of Clause 19, further comprising: authenticating a user via an authentication device; and unlatching the bin body from the bin housing via the latching mechanism in response to authenticating the user via the authentication device.

Clause 21. A system and methods associated to highly optimized medication storage and dispensing solutions in healthcare settings including a wall mounted vertically mounted bin array with configurable wirelessly connected smart bins (different sizes), plurality of user interface, server authorized actuator lock, location tracking, and enables enterprise solution for inventory tracking, a system comprises a processor, memory, input/output device, environmental sensor, tamper detection and wireless interface, an E-ink display, microphone, buzzer and multicolor LED for user interface, an identity authentication module (IAM) interface that enables plurality of user authentication methods such as smart card reader or biometric, a FET based drive circuitry to drive the multicolor LED that supports plurality of colors, intensity and flash pattern to indicate glanceable status of the system, a drive circuitry for E-ink user interface with plurality of views each configured to present the current state of the workflow, a drive circuitry for piezo electric buzzer to provide audio feedback to the user, a microphone interface circuitry for the user to provide wakeup words and or voice prompts, an actuator latch drive circuitry and latch state read back methods, a memory interface to store state and statistics of vertically mounted bin array status, a sensor interface to monitor tamper, environmental condition & content sensing, a crypto and secure element interface to safely store public/private keys.

Clause 22. The system architecture in Clause 21, optimizes the existing user space with a wall mounted vertically mounted bin array enclosure and configurable smart bins with wireless connectivity. In other implementation the vertically mounted bin array enclosure with bin can be placed on countertop.

Clause 23. The system architecture in Clause 21, in one implementation has latch and electronics to drive the latch as part of the bin and in other implementation both the latch and electronics are part of vertically mounted bin array enclosure.

Clause 24. The system architecture in Clause 21, the bin tilts open giving user access to medication and in other implementation bin pops open as a drawer.

Clause 25. The authentication system in Clause 21, automatically determines a plurality of user authorization methods and the user then selects one of the determined authorization methods to unlock the vertically mounted bin array.

Clause 26. A method that securely transmits the user identity to the server and gets authorization to unlock the vertically mounted bin array.

Clause 27. The authentication method in Clause 26, in some implementation use contactless smart card and in other implementations it could use barcode, biometric identification, ECG based wearable device or a mobile phone.

Clause 28. The authentication method in Clause 26, in some implementation could be remote authentication. For example, if the user loses their badge or smart phone the super user can provide remote authentication.

Clause 29. The method that utilizes the sensor interface to automatically identify the quantity of contents in the vertically mounted bin array and tamper detection of vertically mounted bin array or enclosure.

Clause 30. The method in Clause 29, monitors for tamper detection on vertically mounted bin array enclosure attached to wall and the vertically mounted bin array attached to enclosure in real time using optics or electromagnetic sensing.

Clause 31. The method in Clause 29, supports sensor interface such as load cell, optics with a light emitter (e.g., light emitting diode) and photodiode, acoustics or RF to sense the quantity of content inside the bin.

Clause 32. A method by which an audible sound indicates user actions such as presenting badge to the vertically mounted bin array or when an actuator command is been executed.

Clause 33. A method according to Clause 32, in some implementation uses a piezo beeper with different tones to indicate different actions.

Clause 34. The communication architecture (CA) for the system in Clause 1, can use plurality of PAN protocols such as (802.15.4/BLE) to talk to the remote device.

Clause 35. A method that utilizes the CA to achieve a beacon for asset tracking or real time and offline mode support Clause 36. The method in Clause 35, where in the implementation of vertically mounted bin array can bypass hospital IT thereby reduce installation time and make it a drop ship model because of PAN protocol support.

Clause 37. The method in Clause 35, supports offline mode. When network connection to the field hub or gateway is lost the vertically mounted bin array will still allow the user to continue with their action and will store and forward the actions when network is restored.

Clause 38. The method in Clause 35, where in ability of the vertically mounted bin array to broadcast beacons to remote host with the medication information for asset tracking. Optionally, users can also read the beacons using a mobile device such as a phone or tablet.

Clause 39. The power architecture for the system in Clause 21, in some implementation use disposable batteries or a rechargeable battery or a supercapacitor as an energy source for each bin.

Clause 40. The PA for the system in Clause 21, in some implementations may require one high capacity energy source to power the entire vertically mounted bin array array. For different implementations of high capacity energy source (PoE, battery, external power supply) and its interface using wired or docking connector see attached slides and docs.

Clause 41. The PA for the system in Clause 21, in some implementation when a vertically mounted bin array is connected to an external power supply, the external power supply may directly power the vertically mounted bin array, or may charge the battery on the bin or enclosure.

Clause 42. The PA for the system in Clause 21, in some implementation may use wireless power transfer to access the vertically mounted bin array smart bin.

Clause 43. Method for charging the system include plurality of wireless energy source.

Clause 44. A method in Clause 43, where in some instance near field (such as NFC, Qi, Resonant and inductive) or far field (such as WiFi, UHF) wireless power transfer are used as energy source to access the vertically mounted bin array.

Clause 45. A method in Clause 43, where in some instance multiplexed wireless charging scheme is used to charge the secure storage solution as only one storage location can be accessed at a given time inside a vertically mounted bin array.

Clause 46. A method in Clause 43, where in some instances use guided lights or mechanical features to dock the secured storage space for wireless charging.

Clause 47. A method for conserving power in battery operated devices based on system factors and user preference, comprising: placing devices in low power states (ranging from system off state to various levels of sleep state) and waking up periodically (wake up period) to enable radio communications and check in with a gateway/hub for updates or to perform transactions, the low power state and wake up period is configured by the gateway/hub for devices based on system usage factors and user preferences.

Clause 48. The method in Clause 47, in some instances uses environmental sensors such as occupancy sensors and in other instances optionally it could use microphone with key word activation, user action by pushing a button or system usage factors such as user presence, office schedule to wake up the device from deep sleep mode.

Clause 49. A method for energy harvesting using plurality of sources to increase vertically mounted bin array smart bin operation life.

Clause 50. A method in Clause 49, where in some instances uses electromagnetic induction from lock actuator action or wireless energy from RF sources to harvest energy.

Clause 51. The E-ink user interface in Clause 21, in some implementation the e-ink will display medication name, dosage and expire date and in other implementations can display icons such as loading dock or in transit to show the current status of associated medication that is been tracked.

Clause 52. The multicolor LED user interface in Clause 21, in some implementation will act as a glanceable status indicator. The LED color, flash pattern and intensity will indicate different status based on user accessing the secure storage location and workflow, wherein during medication loading workflow the led lighting can guide the user to the medication at a glance, if the medication in the vertically mounted bin array expired the LED can flash red, during medication audit the system will guide by lighting the LED's so the user can identify the med easily, and if the battery level lower than threshold led can flash.

Clause 53. A smart container comprising: a compartment having a plurality of walls and an access component; a memory including a non-volatile data store containing a local cache storing a local inventory of the compartment; an electromechanical latch engaged to a fastening hook of the access component; a communication interface disposed within the smart container; an audiovisual element disposed within the smart container; and a processor disposed within the smart container and configured to: receive, via the communication interface, an authenticated request to access the compartment; in response to receiving the authenticated request, actuate the electromechanical latch to disengage the fastening hook, thereby initiating a mechanical movement of the access component to make the compartment accessible; output, upon actuation of the electromechanical latch, an alert via the audiovisual element to identify the smart container; confirm that the electromechanical latch has re-engaged with the fastening hook, thereby securing the compartment; determine a change in the local inventory after the confirming; and update the local inventory in the non-volatile data store according to the change.

Clause 54. The smart container of Clause 53, wherein the access component comprises a hinged lid, and wherein the mechanical movement comprises a rotation of the hinged lid.

Clause 55. The smart container of Clause 53, wherein the fastening hook is configured to retract into a recess when the fastening hook is disengaged.

Clause 56. The smart container of Clause 53, further comprising a stopper configured to limit the access component to a maximum extended position.

Clause 57. The smart container of Clause 53, wherein the access component comprises a drawer, and wherein the mechanical movement comprises a sliding of the drawer.

Clause 58. The smart container of Clause 53, wherein the mechanical movement is initiated using a force from a spring or a motor.

Clause 59. The smart container of Clause 53, wherein a portion of the fastening hook is configured to dislodge into the electromechanical latch when the fastening hook is forcibly disengaged.

Clause 60. The smart container of Clause 53, wherein the audiovisual element includes a display, and wherein the processor is further configured to output the local inventory, including an item description and a quantity, to the display.

Clause 61. The smart container of Clause 53, wherein the smart container is attachable to a stationary mounting frame with other containers or smart containers to form a stack or an array.

Clause 62. The smart container of Clause 53, further comprising one or more sensors including at least one of a load cell, an optical sensor, an electromagnetic sensor, an acoustic sensor, a temperature sensor, a radio frequency (RF) scanner, a shock sensor, a vibration sensor, a tamper sensor, and a location sensor.

Clause 63. The smart container of claim Clause 62, wherein the processor is configured to determine the change in the local inventory using the one or more sensors.

Clause 64. The smart container of claim Clause 62, wherein the processor is further configured to: record periodic sensor data from the one or more sensors in a condition log within the non-volatile data store; and determine whether an attempt to tamper the smart container occurred based on the condition log.

Clause 65. The smart container of Clause 53, wherein the processor is further configured to send, via the communication device, a stock notification to a remote server when a quantity of the local inventory is below a predetermined threshold level.

Clause 66. The smart container of Clause 53, wherein the smart container is configured to operate in a refrigerated environment.

Clause 67. The smart container of Clause 53, wherein the processor is further configured to: synchronize the local inventory with one or more remote smart containers via the communication interface; and receive, from the one or more remote smart containers via the communication interface, periodic updates for the local cache comprising locations and inventories of the one or more remote smart containers.

Clause 68. The smart container of Clause 53, wherein audiovisual element includes at least one of an e-ink display, a light emitting diode (LED), and a speaker.

Clause 69. The smart container of Clause 53, wherein the processor is further configured to: adjust a power state of the processor based on training a machine learning algorithm on usage data collected from a plurality of smart containers.

Clause 70. The smart container of Clause 53, wherein the processor is configured to receive the authenticated request in response to detecting a proximity to an authenticated user.

Clause 71. The smart container of Clause 53, wherein prior to receiving the authenticated request, the processor is configured to: receive, via the communication interface, a query for an item; determine that the item is stored in the local inventory; and send, via the communication interface, a response to the query including an indication that the item is stored in the local inventory, and a location of the smart container.

Clause 72. A method for automatic inventory management, the method comprising: providing a smart container attachable to a stationary mounting frame, the smart container including a compartment having a plurality of walls and an access component; receiving, via a communication interface, an authenticated request to access the compartment; in response to receiving the authenticated request, actuating an electromechanical latch to disengage a fastening hook, thereby initiating a mechanical movement of an access component to make the compartment accessible; outputting, upon actuation of the electromechanical latch, an alert via an audiovisual element to identify the container; confirming that the electromechanical latch has re-engaged with the fastening hook, thereby securing the compartment; determining a change in a local inventory after the confirming; and updating the local inventory in a non-volatile data store according to the change.

Clause 73. The method of Clause 72, wherein the access component includes at least one of a hinged lid and a drawer, and wherein the mechanical movement includes at least one of a rotation of the hinged lid and a sliding of the drawer.

Clause 74. A non-transitory storage medium comprising instructions that, when read by one or more processors, cause a method comprising: receiving, via a communication interface, an authenticated request to access a compartment of a smart container, the compartment having a plurality of walls and an access component; in response to receiving the authenticated request, actuating an electromechanical latch to disengage a fastening hook, thereby initiating a mechanical movement of an access component to make the compartment accessible; outputting, upon actuation of the electromechanical latch, an alert via an audiovisual element to identify the container; confirming that the electromechanical latch has re-engaged with the fastening hook, thereby securing the compartment; determining a change in a local inventory after the confirming; and updating the local inventory in a non-volatile data store according to the change.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

Features described may include machine learning. Machine learning may include models, equations, artificial neural networks, recurrent neural networks, convolutional neural networks, decision trees, or other machine readable artificial intelligence structure. Examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A smart container comprising:
   a compartment having a plurality of walls and an access component;
   a memory including a non-volatile data store containing a local cache storing a local inventory of the compartment;
   an electromechanical latch engaged to a fastening hook of the access component;
   a communication interface disposed within the smart container;
   an audiovisual element disposed within the smart container; and
   a processor disposed within the smart container and configured to:
      receive, via the communication interface, an authenticated request to access the compartment;
      in response to receiving the authenticated request, actuate the electromechanical latch to disengage the fastening hook, thereby initiating a mechanical movement of the access component to make the compartment accessible;
      output, upon actuation of the electromechanical latch, an alert via the audiovisual element to identify the smart container;
      confirm that the electromechanical latch has re-engaged with the fastening hook, thereby securing the compartment;
      determine a change in the local inventory after the confirming; and
      update the local inventory in the non-volatile data store according to the change.

2. The smart container of claim 1, wherein the access component comprises a hinged lid, and wherein the mechanical movement comprises a rotation of the hinged lid.

3. The smart container of claim 1, wherein the fastening hook is configured to retract into a recess when the fastening hook is disengaged.

4. The smart container of claim 1, further comprising a stopper configured to limit the access component to a maximum extended position.

5. The smart container of claim 1, wherein the access component comprises a drawer, and wherein the mechanical movement comprises a sliding of the drawer.

6. The smart container of claim 1, wherein the mechanical movement is initiated using a force from a spring or a motor.

7. The smart container of claim 1, wherein a portion of the fastening hook is configured to dislodge into the electromechanical latch when the fastening hook is forcibly disengaged.

8. The smart container of claim 1, wherein the audiovisual element includes a display, and wherein the processor is further configured to output the local inventory, including an item description and a quantity, to the display.

9. The smart container of claim 1, wherein the smart container is attachable to a stationary mounting frame with other containers or smart containers to form a stack or an array of different sized containers.

10. The smart container of claim 1, further comprising one or more sensors including at least one of a load cell, an optical sensor, an electromagnetic sensor, an acoustic sensor, a temperature sensor, a radio frequency (RF) scanner, a shock sensor, a vibration sensor, a tamper sensor, and a location sensor.

11. The smart container of claim 10, wherein the processor is configured to determine the change in the local inventory using the one or more sensors within the compartment.

12. The smart container of claim 10, wherein the processor is further configured to:
   record periodic sensor data from the one or more sensors in a condition log within the non-volatile data store; and
   determine whether an attempt to tamper the smart container occurred based on the condition log.

13. The smart container of claim 1, wherein the processor is further configured to send, via the communication device, a stock notification to a remote server when a quantity of the local inventory is below a predetermined threshold level.

14. The smart container of claim 1, wherein the processor is further configured to:
   synchronize the local inventory with one or more remote smart containers via the communication interface; and
   receive, from the one or more remote smart containers via the communication interface, periodic updates for the local cache comprising locations and inventories of the one or more remote smart containers.

15. The smart container of claim 1, wherein the processor is further configured to:
   adjust a power state of the processor based on training a machine learning algorithm on usage data collected from a plurality of smart containers.

16. The smart container of claim 1, wherein the processor is configured to receive the authenticated request in response to detecting a proximity to an authenticated user.

17. The smart container of claim 1, wherein prior to receiving the authenticated request, the processor is configured to:

receive, via the communication interface, a query for an item;

determine that the item is stored in the local inventory; and send, via the communication interface, a response to the query including an indication that the item is stored in the local inventory, and a location of the smart container.

18. A method for automatic inventory management, the method comprising:

providing a smart container attachable to a stationary mounting frame, the smart container including a compartment having a plurality of walls and an access component;

receiving, via a communication interface, an authenticated request to access the compartment;

in response to receiving the authenticated request, actuating an electromechanical latch to disengage a fastening hook, thereby initiating a mechanical movement of an access component to make the compartment accessible;

outputting, upon actuation of the electromechanical latch, an alert via an audiovisual element to identify the container;

confirming that the electromechanical latch has re-engaged with the fastening hook, thereby securing the compartment;

determining a change in a local inventory after the confirming; and updating the local inventory in a non-volatile data store according to the change.

19. A non-transitory storage medium comprising instructions that, when read by one or more processors, cause a method comprising:

receiving, via a communication interface, an authenticated request to access a compartment of a smart container, the compartment having a plurality of walls and an access component;

in response to receiving the authenticated request, actuating an electromechanical latch to disengage a fastening hook, thereby initiating a mechanical movement of an access component to make the compartment accessible;

outputting, upon actuation of the electromechanical latch, an alert via an audiovisual element to identify the container;

confirming that the electromechanical latch has re-engaged with the fastening hook, thereby securing the compartment;

determining a change in a local inventory after the confirming; and updating the local inventory in a non-volatile data store according to the change.

* * * * *